(12) United States Patent
Wichmann et al.

(10) Patent No.: US 12,221,641 B2
(45) Date of Patent: Feb. 11, 2025

(54) STEVIA REBAUDIANA KAURENOIC ACID HYDROXYLASE VARIANTS FOR HIGH EFFICIENCY PRODUCTION OF REBAUDIOSIDES

(71) Applicant: AMYRIS, INC., Emeryville, CA (US)

(72) Inventors: Gale A. Wichmann, Emeryville, CA (US); Wenzong Li, Emeryville, CA (US); Sean Lund, Emeryville, CA (US); Shaina J. Jackson, Emeryville, CA (US); Chantal V. Garcia De Gonzalo, Emeryville, CA (US); Hailley Warbington, Emeryville, CA (US); Yi Xiong, Emeryville, CA (US); Svetlana Alekseyevna Borisova, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 927 days.

(21) Appl. No.: 17/285,888

(22) PCT Filed: Oct. 14, 2019

(86) PCT No.: PCT/US2019/056153
§ 371 (c)(1),
(2) Date: Apr. 15, 2021

(87) PCT Pub. No.: WO2020/081468
PCT Pub. Date: Apr. 23, 2020

(65) Prior Publication Data
US 2021/0371892 A1 Dec. 2, 2021

Related U.S. Application Data

(60) Provisional application No. 62/745,900, filed on Oct. 15, 2018.

(51) Int. Cl.
*C12P 19/56* (2006.01)
*C12N 1/18* (2006.01)
(Continued)

(52) U.S. Cl.
CPC ............. *C12P 19/56* (2013.01); *C12N 1/185* (2021.05); *C12N 9/0042* (2013.01);
(Continued)

(58) Field of Classification Search
None
See application file for complete search history.

(56) References Cited

U.S. PATENT DOCUMENTS 9,631,215 B2 * 4/2017 Houghton-Larsen .... C12N 9/88

FOREIGN PATENT DOCUMENTS

| WO | WO 2016/073740 A1 | 5/2016 |
| WO | WO 2016/120486 A1 | 8/2016 |
| WO | WO 2017/060318 A2 | 4/2017 |

OTHER PUBLICATIONS

International Search Report and Written Opinion of PCT/US2019/056153 dated Apr. 1, 2020; 19 pages.
(Continued)

*Primary Examiner* — David W Berke-Schlessel
(74) *Attorney, Agent, or Firm* — Squire Patton Boggs (US) LLP

(57) ABSTRACT

Provided herein are compositions and methods for improved production of steviol glycosides in a host cell. In some embodiments, the host cell is genetically modified to comprise a heterologous nucleotide sequence encoding a *Stevia rebaudiana* kaurenoic acid hydroxylase. In some embodiments, the host cell further comprises one or more heterologous nucleotide sequence encoding further enzymes of a pathway capable of producing one or more steviol glycosides in the host cell. The compositions and methods
(Continued)

Figure 1:
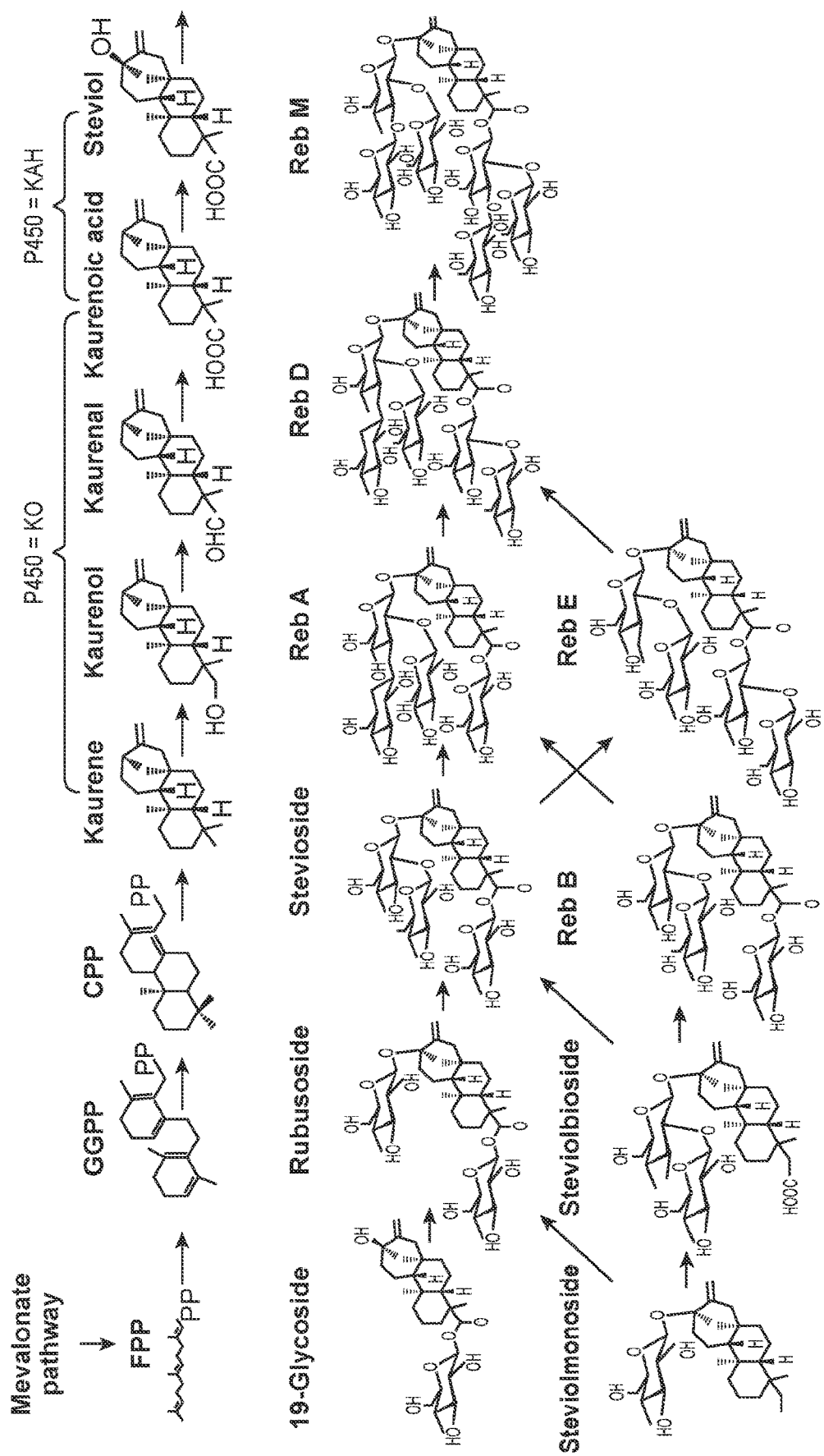

described herein provide an efficient route for the heterologous production of steviol glycosides, including but not limited to, rebaudioside D and rebaudioside M.

3 Claims, 6 Drawing Sheets

Specification includes a Sequence Listing.

(51) Int. Cl.
    *C12N 9/02*     (2006.01)
    *C12N 9/10*     (2006.01)
    *C12N 9/88*     (2006.01)
    *C12N 9/90*     (2006.01)
    *C12R 1/865*     (2006.01)

(52) U.S. Cl.
    CPC .......... *C12N 9/0073* (2013.01); *C12N 9/1051* (2013.01); *C12N 9/88* (2013.01); *C12N 9/90* (2013.01); *C07K 2319/03* (2013.01); *C12R 2001/865* (2021.05); *C12Y 106/02004* (2013.01); *C12Y 114/13079* (2013.01); *C12Y 114/14* (2013.01); *C12Y 204/01017* (2013.01); *C12Y 205/01001* (2013.01); *C12Y 402/03019* (2013.01); *C12Y 505/01012* (2013.01)

(56) References Cited

OTHER PUBLICATIONS

Database UniProt [Online]; Feb. 6, 2013, "SubName: Full=Cytochrome P450 mono-oxygenase {ECO:0000313EHBL:AF064617. 1};" XP002796978, retrieved from EBI accession No. UniProt: K7PPX3, Database accession No. K7PPX3 sequence.

Database UniProt [Online]; Nov. 22, 2017, "SubName: Full=Putative isoflavone 21-hydroxylase {ECO:0000313 I EMBL:0TG27646. 1};" XP002796979, retrieved from EBI accession No. UniProt:A0A251UXQ8 Database accession No. A0A251UXQ8 sequence.

Database UniProt [Online], Jul. 18, 2018, "SubName: Full=Cytochrome P450-1ike protein {ECO:0000313 I EMBL:PWA49542. 1};" XP002796980, retrieved from EBI accession No. UniProt: A0A2U1LKL9, Database accession No. AQA2U1LKL9 sequence.

Database Geneseq [Online], Sep. 22, 2016, "Stevia rebaudiana KAH protein, SEQ:94.", XP002796995, retrieved from EBI accession No. GSP:BDC93693, Database accession No. BDC93693 sequence.

Wang et al., "Pathway mining-based integration of critical enzyme parts for de novo biosynthesis of steviolglycosides sweetener in *Escherichia coli*", Cell Research, vol. 26, No. 2, Feb. 1, 2016, pp. 258-261, XPO02772958, DOI: 10.1038/CR.2015.111.

\* cited by examiner

STEVIA REBAUDIANA KAURENOIC ACID HYDROXYLASE VARIANTS FOR HIGH EFFICIENCY PRODUCTION OF REBAUDIOSIDES

CROSS-REFERENCE TO RELATED APPLICATIONS

This application is a National Stage application of PCT Application PCT/US2019/056153, filed Ser. No. 15/688,555, filed Oct. 14, 2019, which claims the benefit of U.S. Provisional Application No. 62/745,900, filed Oct. 15, 2018, the entire contents of each of which are herein incorporated in their entirety for all purposes.

I. FIELD

The present disclosure relates to certain kaurenoic acid hydroxylases (KAHs), compositions comprising the same, host cells comprising the same, and methods of their use for the production of steviol and/or rebaudiosides including rebaudioside D and rebaudioside M.

II. BACKGROUND

Zero-calorie sweeteners derived from natural sources are desired to limit the ill effects of high-sugar consumption (e.g., diabetes and obesity). Rebaudioside M (RebM), is one of many sweet-tasting compounds produced by the *stevia* plant (*S. rebaudiana Bertoni*). Of all the rebaudiosides, RebM has the highest potency (~200-300× sweeter than sucrose) and is the cleanest tasting. However, RebM is only produced in minor quantities by the *Stevia* plant and is a small fraction of the total steviol glycoside content (<1.0%). Ohta et al., 2010, *J. Appl. Glycosci.*, 57, 199-209 (2010). As such, it is desirable to produce RebM using biotechnological routes allowing production in large quantities and at high purity.

To economically produce a product using biotechnology, each step in the bioconversion from feedstock to product needs to have a high conversion efficiency (ideally >90%). In our engineering of yeast to produce RebM, we identified a limitation in the biosynthetic step early in the pathway to RebM that takes kaurenoic acid to steviol (FIG. 1).

The kaurenoic acid hydroxylase (KAH) enzyme is found in the plant *Stevia rebaudiana* and normally acts to produce the C20 isoprenoid steviol from the plant hormone-precursor kaurenoic acid. Even though *S. rebaudiana* can accumulate up to approximately 15% of leaf dry weight in steviol glycosides, the flux through the KAH enzyme may not be what is required for high volume RebM production in yeast for commercial manufacturing. Conventionally, the wild type KAH enzyme from *Stevia rebaudiana* (Sr.KAH) has been used to convert kaurenoic acid to steviol in yeast engineered to produce RebM.

To produce RebM efficiently and at high purity, improved enzymes capable of producing steviol at high efficiency are needed. The compositions and methods provided herein address this need and provide related advantages as well.

III. SUMMARY

Provided herein are compositions and methods for the improved conversion of kaurenoic acid to steviol. These compositions and methods are based in part on the production of certain kaurenoic acid hydroxylases (KAHs) that are capable of converting kaurenoic acid to steviol with remarkably high efficiency. Even a modest improvement in strain performance (e.g., ten percent) with new KAHs can potentially save over ten million dollars in production cost in the future, assuming that the market demand for RebM is 5000 million tons per year.

Certain KAHs described herein are also capable of producing steviol with little or no residual kaurenoic acid. As such, in certain embodiments, the compositions and methods described herein can reduce the costs of downstream processing to obtain a composition with high yield steviol glycosides such as RebM.

In one aspect, provided herein are genetically modified host cells and methods of their use for the production of industrially useful compounds. In one aspect, provided herein is a genetically modified host cell comprising: a heterologous nucleic acid encoding a *Stevia rebaudiana* kaurenoic acid hydroxylase provided herein. In some embodiments, the genetically modified host cell further comprises one or more enzymatic pathways capable of producing steviol and/or steviol glycosides. In certain embodiments, the genetically modified host cell is capable of converting kaurenoic acid to steviol at an efficiency greater than 50%, 55%, 60%, 65%, 70%, 75%, 80%, 85%, 90%, 95%, 96%, 97%, or 98%.

In another aspect, provided herein are methods for producing a heterologous steviol glycoside, the method comprising: culturing a population of genetically modified host cells provided herein, capable of producing the heterologous steviol glycoside as described herein, in a medium with a carbon source under conditions suitable for making said heterologous steviol glycoside compound; and recovering said steviol glycoside from the medium. In some embodiments, heterologous steviol glycoside is selected from the group consisting of RebD and RebM.

In another aspect, provided herein are methods for producing RebD, the method comprising: culturing a population of genetically modified host cells provided herein, capable of producing RebD as described herein, in a medium with a carbon source under conditions suitable for making said RebD; and recovering said RebD from the medium.

In another aspect, provided herein are methods for producing RebM, the method comprising: culturing a population of genetically modified host cells provided herein, capable of producing RebM as described herein, in a medium with a carbon source under conditions suitable for making said RebM; and recovering said RebM from the medium.

In another aspect, provided herein are methods for producing steviol, the method comprising: contacting kaurenoic acid with a kaurenoic acid hydroxylase described herein, capable of converting kaurenoic acid to steviol, under conditions suitable for forming steviol.

In some embodiments, the host cell is a yeast cell. In some embodiments, the yeast is *Saccharomyces cerevisiae*. In some embodiments, the host cell produces RebD or RebM at high efficiency. In some embodiments, the host cell produces an increased amount of RebD or RebM compared to a yeast cell not comprising the *Stevia rebaudiana* kaurenoic acid hydroxylase polypeptide provided herein.

IV. BRIEF DESCRIPTION OF THE FIGURES

FIG. 1 provides an enzymatic pathway from the native yeast metabolite farnesyl pyrophosphate (FPP) to Rebaudioside M (RebM). Depicted in the figure are geranylgeranyl pyrophosphate (GGPP), copalyl pyrophosphate (CPP), and several rebaudiosides (Reb).

Figure 2:

FIG. 2 provides a schematic diagram of a "landing pad" design used to insert individual KAH enzymes for screening for kaurenoic acid to steviol conversion in yeast.

Figure 3:
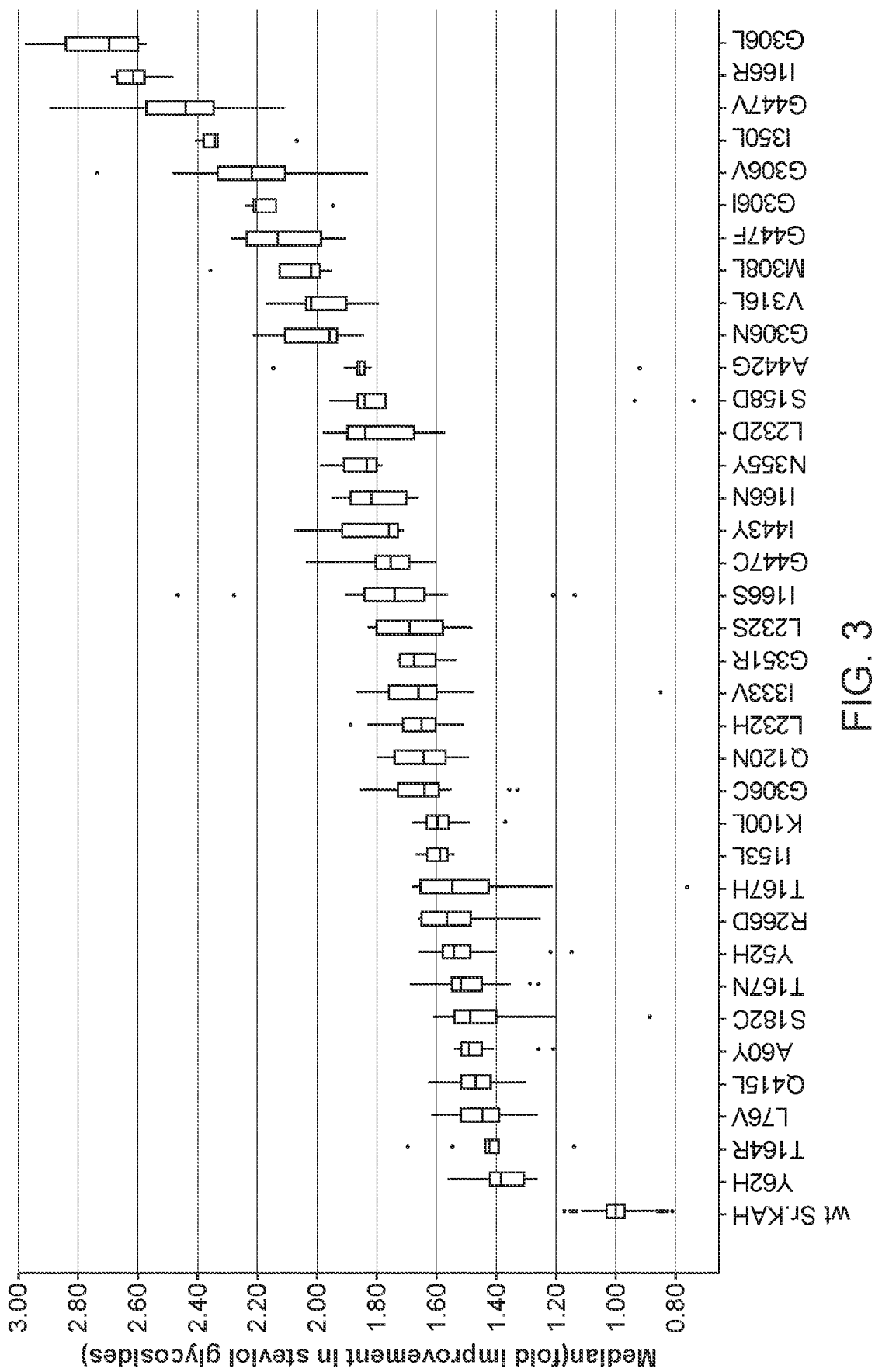

FIG. 3 provides Sr.KAH mutants, each containing a single amino acid change, that have activity at least one standard deviation higher than the wild type Sr.KAH allele. The Y-axis represents the ratio of 19-glycoside (Strain 1) or Reb M (Strain 2) produced by Sr.KAH variant to that of wild type Sr.KAH.

Figure 4:
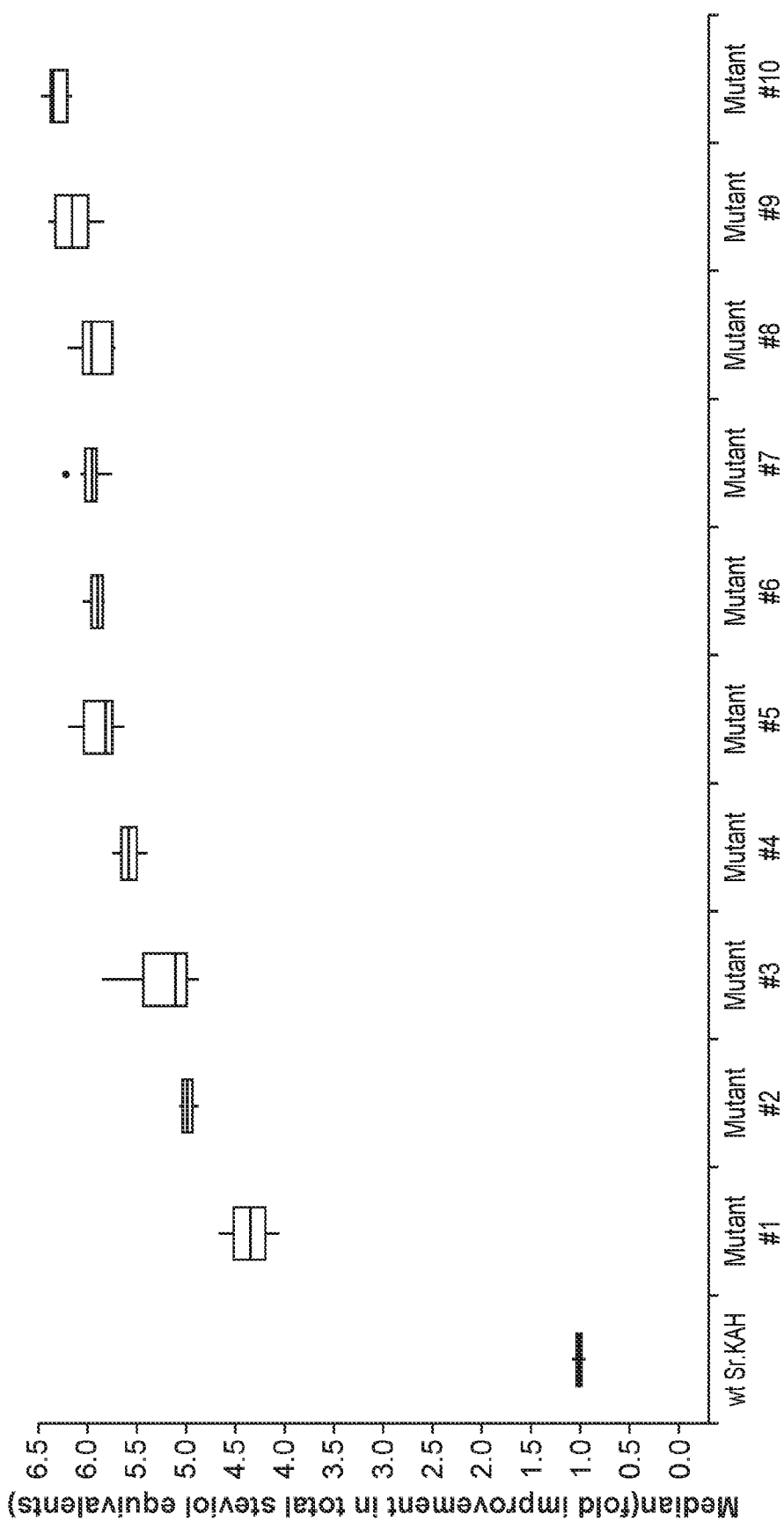

FIG. 4 provides combinations of Sr.KAH protein mutations leading to improvement of in vivo activity from 4.3× to 6.3× in a yeast strain; Sr.KAH activity is measured in the Strain 3 background. The Y-axis is the relative fold increase of mutant Sr. KAH alleles over wild type Sr. KAH; wild type Sr.KAH activity is normalized to one.

Figure 5:
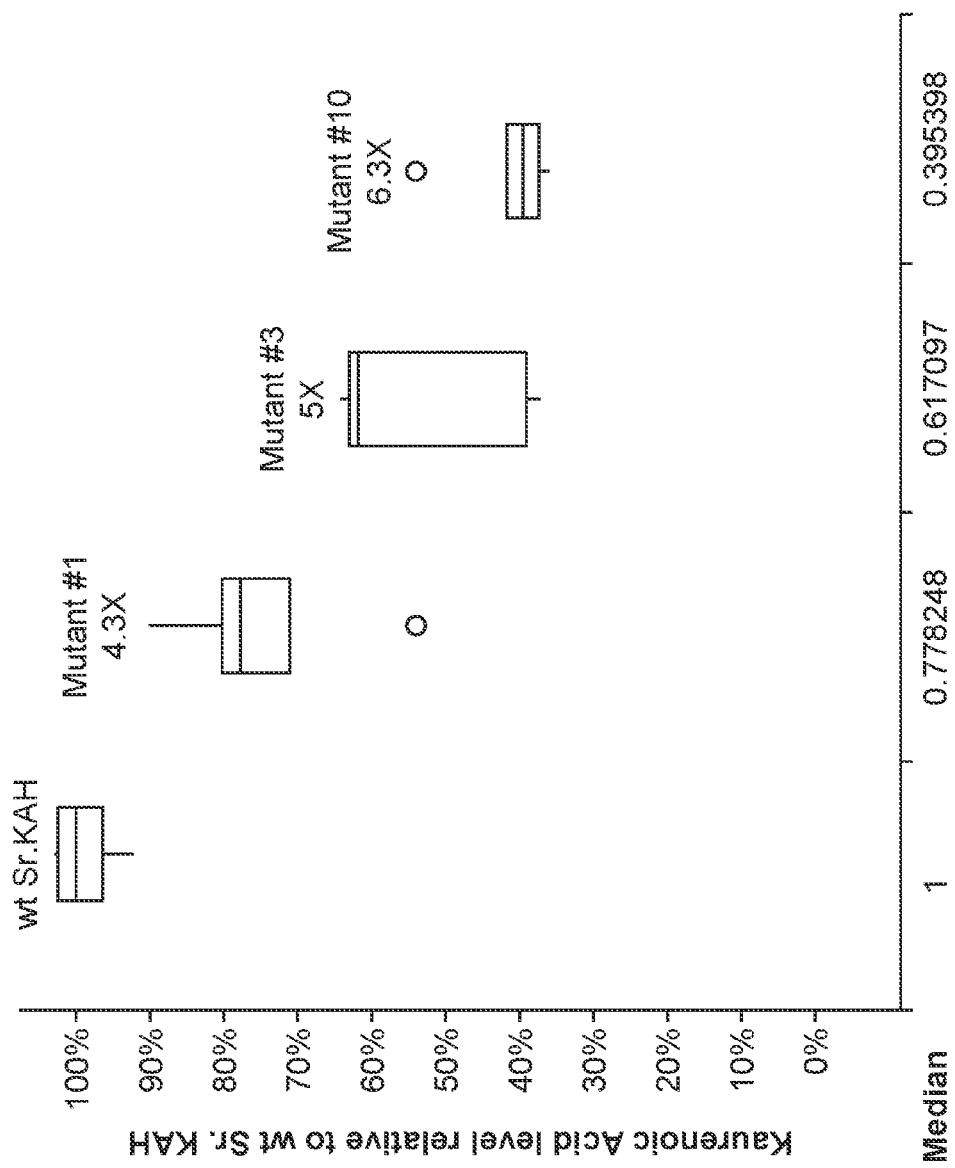

FIG. 5 provides improved KAH mutants leading to a reduction in the substrate kaurenoic acid compared to wild type Sr.KAH demonstrating that Sr.KAH alleles with improved activity are converting more substrate to steviol.

Figure 6:
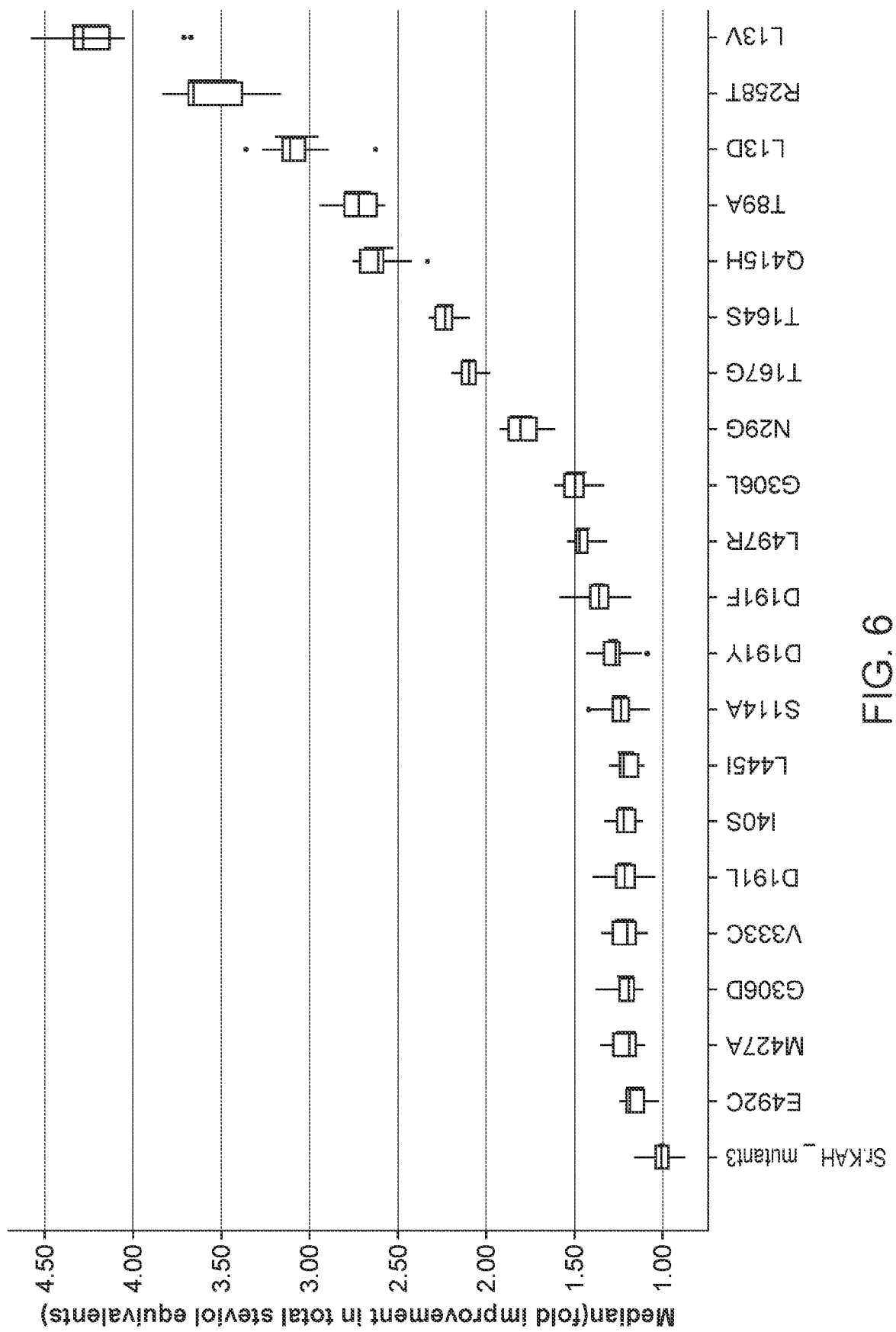

FIG. 6 provides in vivo KAH activity of the degenerate codon library mutants measured in a Tier 1 screen versus the Sr.KAH mutant #3 allele using the titer of total steviol glycosides (μM) as described in Example 7.

V. DETAILED DESCRIPTION OF THE EMBODIMENTS

5.1 Terminology

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

On the other hand, the term "native" or "endogenous" as used herein with reference to molecules, and in particular enzymes and nucleic acids, indicates molecules that are expressed in the organism in which they originated or are found in nature. It is understood that expression of native enzymes or polynucleotides may be modified in recombinant microorganisms.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an enzyme of a steviol pathway, heterologous expression of an enzyme of a steviol glycoside pathway, heterologous expression of a geranylgeranyl diphosphate synthase, heterologous expression of a copalyl diphosphate synthase, heterologous expression of a kaurene synthase, heterologous expression of a kaurene oxidase (e.g., *Pisum sativum* kaurene oxidase), heterologous expression of a steviol synthase (kaurenoic acid hydroxylase), heterologous expression of a cytochrome P450 reductase, heterologous expression of a UGT74G1, heterologous expression of a UGT76G1, heterologous expression of a UGT85C2, heterologous expression of a UGT91D, and heterologous expression of a UGT40087 or its variant.

As used herein, the term "naturally occurring" refers to what is found in nature. For example, a kaurenoic acid hydroxylase that is present in an organism that can be isolated from a source in nature and that has not been intentionally modified by a human in the laboratory is naturally occurring kaurenoic acid hydroxylase. Conversely, as used herein, the term "non-naturally occurring" refers to what is not found in nature but is created by human intervention.

The term "medium" refers to a culture medium and/or fermentation medium.

The term "fermentation composition" refers to a composition which comprises genetically modified host cells and products or metabolites produced by the genetically modified host cells. An example of a fermentation composition is a whole cell broth, which can be the entire contents of a vessel (e.g., a flask, plate, or fermentor), including cells, aqueous phase, and compounds produced from the genetically modified host cells.

As used herein, the term "production" generally refers to an amount of steviol or steviol glycoside produced by a genetically modified host cell provided herein. In some embodiments, production is expressed as a yield of steviol or steviol glycoside by the host cell. In other embodiments, production is expressed as the productivity of the host cell in producing the steviol or steviol glycoside.

As used herein, the term "productivity" refers to production of a steviol or steviol glycoside by a host cell, expressed as the amount of steviol or steviol glycoside produced (by weight) per amount of fermentation broth in which the host cell is cultured (by volume) over time (per hour).

As used herein, the term "yield" refers to production of a steviol or steviol glycoside by a host cell, expressed as the amount of steviol or steviol glycoside produced per amount of carbon source consumed by the host cell, by weight.

As used herein, the term "an undetectable level" of a compound (e.g., RebM, steviol glycosides, or other compounds) means a level of a compound that is too low to be measured and/or analyzed by a standard technique for measuring the compound. For instance, the term includes the level of a compound that is not detectable by the analytical methods known in the art.

The term "kaurene" refers to the compound kaurene, including any stereoisomer of kaurene. In particular embodiments, the term refers to the enantiomer known in the art as ent-kaurene. In particular embodiments, the term refers to the compound according to the following structure:

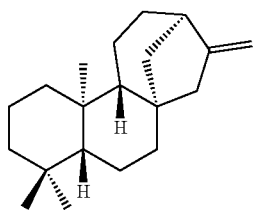

The term "kaurenol" refers to the compound kaurenol, including any stereoisomer of kaurenol. In particular embodiments, the term refers to the enantiomer known in the art as ent-kaurenol. In particular embodiments, the term refers to the compound according to the following structure.

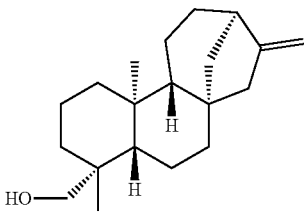

The term "kaurenal" refers to the compound kaurenal, including any stereoisomer of kaurenal. In particular embodiments, the term refers to the enantiomer known in the art as ent-kaurenal. In particular embodiments, the term refers to the compound according to the following structure.

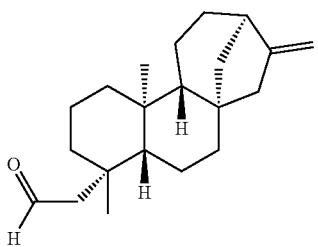

The term "kaurenoic acid" refers to the compound kaurenoic acid, including any stereoisomer of kaurenoic acid. In particular embodiments, the term refers to the enantiomer known in the art as ent-kaurenoic acid. In particular embodiments, the term refers to the compound according to the following structure.

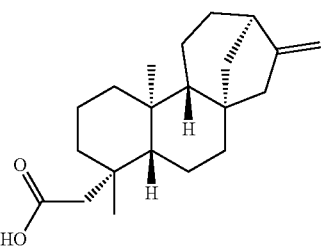

The term "steviol" refers to the compound steviol, including any stereoisomer of steviol. In particular embodiments, the term refers to the compound according to the following structure.

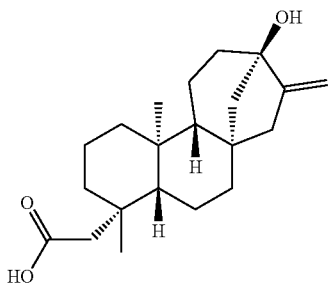

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside N, rebaudioside O, synthetic steviol glycosides, e.g. enzymatically glucosylated steviol glycosides and combinations thereof.

As used herein, the term "variant" refers to a polypeptide differing from a specifically recited "reference" polypeptide (e.g., a wild-type sequence) by amino acid insertions, deletions, mutations, and/or substitutions, but retains an activity that is substantially similar to the reference polypeptide. In some embodiments, the variant is created by recombinant DNA techniques or by mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

As used herein, the term "sequence identity" or "percent identity," in the context or two or more nucleic acid or protein sequences, refers to two or more sequences or subsequences that are the same or have a specified percentage of amino acid residues or nucleotides that are the same. For example, the sequence can have a percent identity of at least 60%, at least 65%, at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer programs and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.*, 22: 4673-4680), ALIGN (Myers et al., (1988) *CABIOS*, 4: 11-17), FASTA (Pearson et al., (1988) *PNAS*, 85:2444-2448; Pearson (1990), *Methods Enzymol.*, 183: 63-98) and gapped BLAST (Altschul et al., (1997) *Nucleic Acids Res.*, 25: 3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=-3, Expectation value=10.0, Word size=11, Max matches in a query range=0). For polypeptide sequence alignment and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0). Alternatively, the following program and parameters can be used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix. In the embodiments described herein, the sequence identity is calculated using BLASTN or BLASTP programs using their default parameters. In the embodiments described herein, the sequence alignment of two or more sequences are performed using Clustal W using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: input).

5.2 Kaurenoic Acid Hydroxylase Polypeptides, Nucleic Acids, and Host Cells

In one aspect, provided herein are modified kaurenoic acid hydroxylase polypeptides which include modification(s) of one or more amino acid residues compared to a wild-type kaurenoic acid hydroxylase polypeptide. In certain embodiments the wild-type kaurenoic acid hydroxylase is *Stevia rebaudiana* kaurenoic acid hydroxylase, i.e. Sr.KAH. In certain embodiments, the wild-type kaurenoic acid hydroxylase polypeptide has the amino acid sequence provided in SEQ ID NO:1. In certain embodiments, the actual residue numbers can be determined by standard alignment techniques relative to SEQ ID NO:1, including those described herein. In particular embodiments, provided herein are the nucleic acids encoding the polypeptides. In particular embodiments, the polypeptides retain activity as a kaurenoic acid hydroxylase to convert kaurenoic acid to steviol. In preferred embodiments, the modified kaurenoic acid hydroxylase polypeptides have improved activity, for instance, compared to Sr.KAH.

Also provided herein are host cells comprising one or more of the kaurenoic acid hydroxylase polypeptides or nucleic acids provided herein. In certain embodiments, the host cells can produce steviol from kaurenoic acid as a starting material. In particular embodiments, the host cells can produce steviol from a carbon source in a culture medium. In particular embodiments, the host cells can produce steviol from a carbon source in a culture medium and can further produce RebA or RebD from the steviol. In particular embodiments, the host cells can further produce rebaudioside M (RebM) from the RebD.

In certain embodiments, provided herein is a kaurenoic acid hydroxylase polypeptide comprising one, two, three, four, five, six, seven, eight, nine, ten, or eleven of the following mutations: I166R, I153L, S158D, G306L, L232D, I333V, I350L, V316L, G447V, M308L. In certain embodiments, the residue numbers of the polypeptide are according to SEQ ID NO:1. In certain embodiments, provided herein is a polypeptide homologous to SEQ ID NO:1 and comprising one, two, three, four, five, six, seven, eight, nine, ten, or eleven of the following mutations: I166R, I153L, S158D, G306L, L232D, I333V, I350L, V316L, G447V, M308L. In any of the previous embodiments, the polypeptide comprises a heterologous amino terminal domain.

In certain embodiments, provided herein a polypeptide homologous to SEQ ID NO:1, residues numbers are provided with respect to SEQ ID NO:1 where actual residue numbers can be determined by standard alignment techniques relative to SEQ ID NO:1, including those described herein.

In certain embodiments, provided herein is a kaurenoic acid hydroxylase polypeptide comprising the following mutations: I166R and I333V. In certain embodiments, the residue numbers are according to SEQ ID NO:1.

In certain embodiments, provided herein is a kaurenoic acid hydroxylase polypeptide comprising the following mutations: I166R, I350L, and G447V. In certain embodiments, the residue numbers are according to SEQ ID NO:1.

In certain embodiments, provided herein is a kaurenoic acid hydroxylase polypeptide comprising the following mutations: I153L, S158D, I166R, L232D, I333V, and I350L. In certain embodiments, the residue numbers are according to SEQ ID NO:1.

In any of the previous embodiments, provided herein the kaurenoic acid hydroxylase polypeptide further comprises one or more mutations selected from E492C, M427A, G306D, V333C, D191L, I40S, L445I, S114A, D191Y, D191F, L497R, G306L, N29G, T167G, T164S, Q415H, T89A, L13D, R258T, and L13V. In certain embodiments, the residue numbers are according to SEQ ID NO:1.

In any of the previous embodiments, provided herein the kaurenoic acid hydroxylase polypeptide further comprises one or more mutations selected from L13D, R258F, and L13V. In certain embodiments, the residue numbers are according to SEQ ID NO:1.

In certain embodiments, provided herein is a kaurenoic acid hydroxylase polypeptide comprising the following mutations: S158D, G306L, and I350L. In certain embodiments, the residue numbers are according to SEQ ID NO:1.

In certain embodiments, provided herein is a kaurenoic acid hydroxylase polypeptide comprising the following mutations: G306L, V316L, I350L, and G447V. In certain embodiments, the residue numbers are according to SEQ ID NO:1.

In certain embodiments, provided herein is a kaurenoic acid hydroxylase polypeptide comprising the following mutations: G306L, V316L, I333V, and I350L. In certain embodiments, the residue numbers are according to SEQ ID NO:1.

In certain embodiments, provided herein is a kaurenoic acid hydroxylase polypeptide comprising the following mutations: S158D, I166R, L232D, G306L, and I333V. In certain embodiments, the residue numbers are according to SEQ ID NO:1.

In certain embodiments, provided herein is a kaurenoic acid hydroxylase polypeptide comprising the following mutations: L232D, G306L, V316L, I333V, and I350L. In certain embodiments, the residue numbers are according to SEQ ID NO:1.

In certain embodiments, provided herein is a kaurenoic acid hydroxylase polypeptide comprising the following mutations: I166R, L232D, and I350L. In certain embodiments, the residue numbers are according to SEQ ID NO:1.

In certain embodiments, provided herein is a kaurenoic acid hydroxylase polypeptide comprising the following mutations: S158D, I166R, G306L, M308L, V316L, and I350L. In certain embodiments, the residue numbers are according to SEQ ID NO:1.

In certain embodiments, provided herein is a kaurenoic acid hydroxylase polypeptide comprising at least one of the following mutations: Y62H, T164R, L76V, Q415L, A60Y, S182C, T167N, Y52H, R266D, T167H, I153L, K100L, G306C, Q120N, L232H, I333V, G351R, L232S, I166S, W447C, I443Y, I166N, N355Y, L232D, S158D, A442G, G306N, V316L, M308L, G447F, G306I, G306V, I350L, G447V, I166R, and G306L. In certain embodiments, the residue numbers are according to SEQ ID NO:1.

In certain embodiments, provided herein is a kaurenoic acid hydroxylase polypeptide of any of the previous embodiments, further comprising at least one of the following mutations: E492C, M427A, G306D, V333C, D191L, I40S, L445I, S114A, D191Y, D191F, L497R, G306L, N29G, T167G, T164S, Q415H, T89A, L13D, R258T, and L13V. In certain embodiments, the residue numbers are according to SEQ ID NO:1.

In certain embodiments, provided herein is a chimeric kaurenoic acid hydroxylase polypeptide comprising a catalytic domain of a *Stevia rebaudiana* kaurenoic acid hydroxylase, and an N-terminal transmembrane domain of an endoplasmic reticulum (ER) bound protein, wherein the N-terminal transmembrane domain is covalently linked to the catalytic domain. In still further embodiments, the chimeric kaurenoic acid hydrolase polypeptide further comprises at least one of the following mutations: Y62H, T164R, L76V, Q415L, A60Y, S182C, T167N, Y52H, R266D, T167H, I153L, K100L, G306C, Q120N, L232H, I333V, G351R, L232S, I166S, W447C, I443Y, I166N, N355Y, L232D, S158D, A442G, G306N, V316L, M308L, G447F, G306I, G306V, I350L, G447V, I166R, and G306L. In certain embodiments, the residue numbers are according to SEQ ID NO:1.

In certain embodiments, provided herein is a chimeric kaurenoic acid hydroxylase polypeptide comprising a catalytic domain of a *Stevia rebaudiana* kaurenoic acid hydroxylase, and an N-terminal transmembrane domain of ATR2, wherein the N-terminal transmembrane domain is covalently linked to the catalytic domain.

In certain embodiments, provided herein is a chimeric kaurenoic acid hydroxylase polypeptide comprising a catalytic domain of a *Stevia rebaudiana* kaurenoic acid hydroxylase wherein the catalytic domain comprises amino acids 23 through 500 of the *Stevia rebaudiana* kaurenoic acid hydroxylase, and an N-terminal transmembrane domain of ATR2, wherein the N-terminal domain comprises amino acids 1 through 72, and wherein the N-terminal transmembrane domain is covalently linked to the catalytic domain. In certain embodiments, the N-terminal domain of the chimeric kaurenoic acid hydroxylase comprises amino acids 1 through 72 of SEQ ID No. 22. In certain embodiments, the catalytic domain comprises amino acids 23 through 500 of SEQ ID No. 1.

In certain embodiments, provided herein the catalytic domain comprises amino acids 5 through 500 of the *Stevia rebaudiana* kaurenoic acid hydroxylase.

In certain embodiments, provided herein the catalytic domain comprises amino acids 23 through 500 of the *Stevia rebaudiana* kaurenoic acid hydroxylase.

In certain embodiments, provided herein the catalytic domain comprises amino acids 47 through 500 of the *Stevia rebaudiana* kaurenoic acid hydroxylase.

In certain embodiments, the N-terminal domain of the chimeric kaurenoic acid hydroxylase polypeptide comprises amino acids 1 through 72 of the *Arabidopsis thaliana* ATR2 protein. In certain embodiments, the N-terminal domain comprises amino acids 1 through 72 of SEQ ID NO. 22.

In certain embodiments, the N-terminal domain of the chimeric kaurenoic acid hydroxylase polypeptide comprises amino acids 1 through 50 of the *Arabidopsis thaliana* ATR2 protein. In certain embodiments, the N-terminal domain comprises amino acids 1 through 50 of SEQ ID NO. 22.

In any of the previous embodiment, the chimeric kaurenoic acid hydroxylase polypeptide further comprises at least one mutation at kaurenoic acid hydroxylase positions E492C, M427A, G306D, V333C, D191L, I40S, L445I, S114A, D191Y, D191F, L497R, G306L, N29G, T167G, T164S, Q415H, T89A, L13D, R258T, and L13V, according to SEQ ID NO. 1.

In certain embodiments, provided herein is a kaurenoic acid hydroxylase polypeptide comprising a heterologous amino terminal domain. In certain embodiments, the kaurenoic acid hydroxylase polypeptide comprising a heterologous amino terminal domain is also known as a chimeric kaurenoic acid hydroxylase polypeptide.

In certain embodiments, provided herein is a substituted amino terminal segment of a kaurenoic acid hydroxylase polypeptide that is substituted with a heterologous amino terminal domain. In some embodiments, provided herein the substituted amino terminal segment (the segment removed) comprises 4, 22, or 46 amino acids from the N-terminus of a full length kaurenoic acid hydroxylase polypeptide according to the residue positions of SEQ ID NO: 1. In some embodiments, provided herein the substituted amino terminal segment comprises a deletion of amino acids 1 through 4 from the N-terminus of the kaurenoic acid hydroxylase polypeptide, according to the residue positions of SEQ ID NO: 1. In some embodiments, provided herein the substituted amino terminal segment comprises a deletion of amino acids 1 through 5 from the N-terminus of the kaurenoic acid hydroxylase polypeptide, according to the residue positions of SEQ ID NO: 1. In some embodiments, provided herein the substituted amino terminal segment comprises a deletion of amino acids 1 through 10 from the N-terminus of the kaurenoic acid hydroxylase polypeptide, according to the residue positions of SEQ ID NO: 1. In some embodiments, provided herein the substituted amino terminal segment comprises a deletion of amino acids 1 through 15 from the N-terminus of the kaurenoic acid hydroxylase polypeptide, according to the residue positions of SEQ ID NO: 1. In some embodiments, provided herein the substituted amino terminal segment comprises a deletion of amino acids 1 through 20 from the N-terminus of the kaurenoic acid hydroxylase polypeptide, according to the residue positions of SEQ ID NO: 1. In some embodiments, provided herein the substituted amino terminal segment comprises a deletion of amino acids 1 through 22 from the N-terminus of the kaurenoic acid hydroxylase polypeptide, according to the residue positions of SEQ ID NO: 1. In some embodiments, provided herein the substituted amino terminal segment comprises a deletion of amino acids 1 through 25 from the N-terminus of the kaurenoic acid hydroxylase polypeptide, according to the residue positions of SEQ ID NO: 1. In some embodiments, provided herein the substituted amino terminal segment comprises a deletion of amino acids 1 through 30 from the N-terminus of the kaurenoic acid hydroxylase polypeptide, according to the residue positions of SEQ ID NO: 1. In some embodiments, provided herein the substituted amino terminal segment comprises a deletion of amino acids 1 through 35 from the N-terminus of the kaurenoic acid hydroxylase polypeptide, according to the residue positions of SEQ ID NO: 1. In some embodiments, provided herein the substituted amino terminal segment comprises a deletion of amino acids 1 through 40 from the N-terminus of the kaurenoic acid hydroxylase polypeptide, according to the residue positions of SEQ ID NO: 1. In some embodiments, provided herein the substituted amino terminal segment comprises a deletion of amino acids 1 through 45 from the N-terminus of the kaurenoic acid hydroxylase polypeptide, according to the residue positions of SEQ ID NO: 1. In some embodiments, provided herein the substituted amino terminal segment comprises a deletion of amino acids 1 through 46 from the N-terminus of the kaurenoic acid hydroxylase polypeptide, according to the residue positions of SEQ ID NO: 1.

In some embodiments, provided herein the substituted heterologous amino terminal domain (the segment added) is from a heterologous protein. In some embodiments, provided herein the substituted heterologous amino terminal domain is an N-terminal transmembrane domain of an endoplasmic reticulum (ER) bound protein. In some embodiments, provided herein the substituted heterologous amino terminal domain is from ATR2 (*Arabidopsis thaliana* cytochrome P450 reductase), Aa.CPR (*Artemisia annua*), Sr.KO (*Stevia rebaudiana* kaurene oxidase), ERG11 (*Saccharomyces cerevisiae* membrane protein), ALG11 (*Saccharomyces cerevisiae* membrane protein), SEC66 (*Saccharomyces cerevisiae* membrane protein), NUS1 (*Saccharomyces cerevisiae* membrane protein), RCR1 (*Saccharomyces cerevisiae* membrane protein), or UBP1 (*Saccharomyces cerevisiae* membrane protein).

In certain embodiments, the heterologous amino terminal segment is selected from the amino terminal of any of SEQ ID NOs: 33-40. In some embodiments, provided herein the substituted heterologous amino terminal domain comprises amino acids 1 through 10 of the heterologous protein. In some embodiments, provided herein the substituted heterologous amino terminal domain comprises amino acids 1 through 20 of the heterologous protein. In some embodiments, provided herein the substituted heterologous amino terminal domain comprises amino acids 1 through 23 of the heterologous protein. In some embodiments, provided herein the substituted heterologous amino terminal domain comprises amino acids 1 through 25 of the heterologous protein. In some embodiments, provided herein the substituted heterologous amino terminal domain comprises amino acids 1 through 30 of the heterologous protein. In some embodiments, provided herein the substituted heterologous amino terminal domain comprises amino acids 1 through 35 of the heterologous protein. In some embodiments, provided herein the substituted heterologous amino terminal domain comprises amino acids 1 through 40 of the heterologous protein. In some embodiments, provided herein the substituted heterologous amino terminal domain comprises amino acids 1 through 45 of the heterologous protein. In some embodiments, provided herein the substituted heterologous amino terminal domain comprises amino acids 1 through 50 of the heterologous protein. In some embodiments, provided herein the substituted heterologous amino terminal domain comprises amino acids 1 through 51 of the heterologous protein. In some embodiments, provided herein the substituted heterologous amino terminal domain comprises amino acids 1 through 52 of the heterologous protein. In some embodiments, provided herein the substituted heterologous amino terminal domain comprises amino acids 1 through 55 of the heterologous protein. In some embodiments, provided herein the substituted heterologous amino terminal domain comprises amino acids 1 through 60 of the heterologous protein. In some embodiments, provided herein the substituted heterologous amino terminal domain comprises amino acids 1 through 62 of the heterologous protein. In some embodiments, provided herein the substituted heterologous amino terminal domain comprises amino acids 1 through 65 of the heterologous protein. In some embodiments, provided herein the substituted heterologous amino terminal domain comprises amino acids 1 through 66 of the heterologous protein. In some embodiments, provided herein the substituted heterologous amino terminal domain comprises amino acids 1 through 70 of the heterologous protein. In some embodiments, provided herein the substituted heterologous amino terminal domain comprises amino acids 1 through 72 of the heterologous protein. In some embodiments, provided herein the substituted heterologous amino terminal domain comprises amino acids 1 through 75 of the heterologous protein. In some embodiments, provided herein the substituted heterologous amino terminal domain comprises amino acids 1 through 80 of the heterologous protein. In some embodiments, provided herein the substituted heterologous amino terminal domain comprises amino acids 1 through 85 of the heterologous protein. In some embodiments, provided herein the substituted heterologous amino terminal domain comprises amino acids 1 through 90 of the heterologous protein. In some embodiments, provided herein the substituted heterologous amino terminal domain comprises amino acids 1 through 95 of the heterologous protein. In some embodiments, provided herein the substituted heterologous amino terminal domain comprises amino acids 1 through 100 of the heterologous protein. In some embodiments, provided herein the substituted heterologous amino terminal domain comprises amino acids 1 through 105 of the heterologous protein. In some embodiments, provided herein the substituted heterologous amino terminal domain comprises amino acids 1 through 110 of the heterologous protein. In some embodiments, provided herein the substituted heterologous amino terminal domain comprises amino acids 1 through 115 of the heterologous protein. In some embodiments, provided herein the substituted heterologous amino terminal domain comprises amino acids 1 through 119 of the heterologous protein.

In certain embodiments, provided herein is a kaurenoic acid hydroxylase polypeptide comprising a heterologous amino terminal segment. In certain embodiments, an amino terminal segment of a kaurenoic acid hydroxylase polypeptide is substituted with a heterologous amino terminal domain. In some embodiments, the substituted amino terminal segment (the segment removed) has from 4-42 amino acids. In some embodiments, the substituted amino terminal segment has 4, 22, 38, or 42 amino acids. In some embodiments, the heterologous amino terminal segment (the segment added, replacing the removed segment) is from ATR2 (*Arabidopsis thaliana* cytochrome P450 reductase), CYP816 (a cytochrome P450 from Santalum album), or Sr.KO (*Stevia rebaudiana* kaurene oxidase). In certain embodiments, the heterologous amino terminal segment is selected from the amino terminal segment of any of SEQ ID NOs: 2-6. In certain embodiments, 22 amino terminal amino acids are substituted with the amino terminal segment of SEQ ID NO:2. In certain embodiments, four amino terminal amino acids are substituted with the amino terminal segment of SEQ ID NO:3. In certain embodiments, 42 amino terminal amino acids are substituted with the amino terminal segment of SEQ ID NO:4. In certain embodiments, four amino terminal amino acids are substituted with the amino terminal segment of SEQ ID NO:5. In certain embodiments, 38 amino terminal amino acids are substituted with the amino terminal segment of SEQ ID NO:6. In certain embodiments, any substitution of this paragraph is combined with any one of more of the mutations described above.

In certain embodiments, the kaurenoic acid hydroxylase polypeptide according to the above embodiments produces at least 1.5-fold, at least 2.0-fold, at least 2.5-fold, at least 3.0-fold, at least 3.5-fold, at least 4.0-fold, at least 4.5-fold, at least 5.0-fold, at least 5.5-fold, or at least 6.0-fold more steviol and steviol glycosides compared to wild-type *Stevia rebaudiana* kaurenoic acid hydroxylase polypeptide according to SEQ ID NO:1.

In certain embodiments, the modified *Stevia rebaudiana* kaurenoic acid hydroxylase polypeptide is capable of converting kaurenoic acid to steviol at high efficiency. In certain embodiments, the modified *Stevia rebaudiana* kaurenoic acid hydroxylase polypeptide is capable of converting kaurenoic acid to steviol at an efficiency of greater than 30%. In certain embodiments, the modified *Stevia rebaudiana* kaurenoic acid hydroxylase polypeptide is capable of converting kaurenoic acid to steviol at an efficiency of greater than 35%. In certain embodiments, the modified *Stevia rebaudiana* kaurenoic acid hydroxylase polypeptide is capable of converting kaurenoic acid to steviol at an efficiency of greater than 40%. In certain embodiments, the modified *Stevia rebaudiana* kaurenoic acid hydroxylase polypeptide is capable of converting kaurenoic acid to steviol at an efficiency of greater than 50%. In certain embodiments, the modified *Stevia rebaudiana* kaurenoic acid hydroxylase polypeptide is capable of converting kaurenoic acid to steviol at an efficiency of greater than 60%. In certain embodiments, the modified *Stevia rebaudiana* kaurenoic acid hydroxylase polypeptide is capable of converting kaurenoic acid to steviol at an efficiency of greater than 70%. In certain embodiments, the modified *Stevia rebaudiana* kaurenoic acid hydroxylase polypeptide is capable of converting kaurenoic acid to steviol at an efficiency of greater than 80%. In certain embodiments, the modified *Stevia rebaudiana* kaurenoic acid hydroxylase polypeptide is capable of converting kaurenoic acid to steviol at an efficiency of greater than 90%. In certain embodiments, the modified *Stevia rebaudiana* kaurenoic acid hydroxylase polypeptide is capable of converting kaurenoic acid to steviol at an efficiency of greater than 95%. In certain embodiments, the modified *Stevia rebaudiana* kaurenoic acid hydroxylase polypeptide is capable of converting kaurenoic acid to steviol at an efficiency of greater than 60%, 65%, 70%, 75%, 80%, 85%, 90%, or 95%.

In certain embodiments, the host cell is capable of converting kaurenoic acid to steviol at an efficiency of greater than 30%. In certain embodiments, the host cell is capable of converting kaurenoic acid to steviol an efficiency of greater than 35%. In certain embodiments, the host cell is capable of converting kaurenoic acid to steviol at an efficiency of greater than 40%. In certain embodiments, the host cell is capable of converting kaurenoic acid to steviol at an efficiency of greater than 45%. In certain embodiments, the host cell is capable of converting kaurenoic acid to steviol at an efficiency of greater than 50%. In certain embodiments, the host cell is capable of converting kaurenoic acid to steviol at an efficiency of greater than 55%. In certain embodiments, the host cell is capable of converting kaurenoic acid to steviol at an efficiency of about 58%. In certain embodiments, the host cell is capable of converting kaurenoic acid to steviol at an efficiency of greater than 60%, 65%, 70%, 75%, 80%, 85%, 90%, or 95%.

Efficiency of conversion can be measured by any technique apparent to those of skill in the art. In certain embodiments, efficiency of conversion can be measured by contacting kaurenoic acid with an enzyme or host cell under suitable conditions for forming steviol. Efficiency can be measured by comparing the molar amount of steviol produced compared to the total amount of kaurenoic acid in the resulting composition. Efficiency can also be measured by comparing the total amount of steviol and downstream products of steviol to the total amount of kaurenoic acid, steviol, and downstream products of steviol in the resulting composition.

In certain embodiments, provided herein are host cells comprising a kaurenoic acid hydroxylase polypeptide comprising an amino acid sequence described herein and capable of converting kaurenoic acid to steviol. In certain embodiments, provided herein are host cells comprising a kaurenoic acid hydroxylase polypeptide comprising an amino acid sequence described herein and capable of oxidation of the 13 position of kaurenoic acid. In certain embodiments, provided herein are host cells comprising a kaurenoic acid hydroxylase polypeptide capable of converting kaurenoic acid to steviol at an efficiency greater than 30%, 35%, 40%, 45%, 50%, 55%, 60%, 65%, 70%, 75%, 80%, 85%, 90%, 95%, 96%, or 97%, and wherein the kaurenoic acid hydroxylase polypeptide comprises an amino acid sequence having at least 95% sequence identity to the amino acid sequence of SEQ ID NO:1.

In embodiments described herein, any suitable method can be used to determine corresponding amino acid positions or corresponding loop locations of two polypeptides. In certain embodiments, the sequences of a kaurenoic acid hydroxylase polypeptide and the reference sequence SEQ ID NO:1 can be aligned using Clustal(W or Omega) using its default parameters. In other embodiment, the sequences of a kaurenoic acid hydroxylase polypeptide and the reference sequence SEQ ID NO:1 can be aligned using structural alignments such as SWISS-MODEL, which is a protein structure homology-modelling server, accessible via the ExPASy web server, or from the program DeepView (Swiss Pdb-Viewer).

While the *Stevia rebaudiana* kaurenoic acid hydroxylase polypeptide or any variant *Stevia rebaudiana* kaurenoic acid hydroxylase polypeptide of the host cells accepts kaurenoic acid as a substrate, the source of kaurenoic acid can be any source deemed suitable to those of skill. In certain embodiments, the *Stevia rebaudiana* kaurenoic acid hydroxylase polypeptide or any variant *Stevia rebaudiana* kaurenoic acid hydroxylase polypeptide can be contacted with kaurenoic acid. In certain embodiments, the *Stevia rebaudiana* kaurenoic acid hydroxylase polypeptide or any variant of *Stevia rebaudiana* kaurenoic acid hydroxylase polypeptide can be contacted with a composition comprising kaurenoic acid. In certain embodiments, the composition is derived or sourced from natural products isolated from *Stevia rebaudiana* leaves. In certain embodiments, the composition is microbially derived or sourced. In certain embodiments, the host cell can be contacted with a composition comprising one or more carbon sources.

In certain embodiments, any *Stevia rebaudiana* kaurenoic acid hydroxylase polypeptide suitable for catalyzing a desired reaction can be screened with any suitable method known in the art. For example, a suitable variant *Stevia rebaudiana* kaurenoic acid hydroxylase polypeptide can be assayed in vivo by expressing a heterologous nucleic acid encoding a variant *Stevia rebaudiana* kaurenoic acid hydroxylase polypeptide and screening cells that produce functional *Stevia rebaudiana* kaurenoic acid hydroxylase polypeptide capable of catalyzing oxidation at a desired location of a substrate (e.g., C-13 position of kaurenoic acid). Exemplary screening methods are described in the Examples below. In another example, a suitable variant *Stevia rebaudiana* kaurenoic acid hydroxylase polypeptide can be screened in vitro by contacting a variant *Stevia rebaudiana* kaurenoic acid hydroxylase polypeptide with a substrate such as kaurenoic acid. In this example, assaying the presence of steviol or a steviol glycoside such as RebD can be used as a test to determine whether a *Stevia rebaudiana* kaurenoic acid hydroxylase polypeptide is a suitable enzyme. The reaction can be analyzed by LC-MS or other known methods in the art. See, e.g. WO 2013/022989.

In certain embodiments, a variant *Stevia rebaudiana* kaurenoic acid hydroxylase polypeptide is considered suitable in converting kaurenoic acid to steviol if it is capable of converting kaurenoic acid to steviol at an efficiency of greater than 30%, 40%, 50%, 60%, 70%, 80%, 90%, 95%, 96%, or 97% in vivo.

In advantageous embodiments, the host cell can comprise one or more enzymatic pathways capable of making kaurenoic acid, said pathways taken individually or together. As described herein, the host cells comprise a *Stevia rebaudiana* kaurenoic acid hydroxylase provided herein, capable of converting kaurenoic acid to steviol. In certain embodiments, the host cell further comprises one or more enzymes capable of converting farnesyl diphosphate to geranylgeranyl diphosphate. In certain embodiments, the host cell further comprises one or more enzymes capable of converting geranylgeranyl diphosphate to copalyl diphosphate. In certain embodiments, the host cell further comprises one or more enzymes capable of converting copalyl diphosphate to kaurene. In certain embodiments, the host cell further comprises one or more enzymes capable of converting kaurene to kaurenoic acid. In certain embodiments, the host cell further comprises one or more enzymes capable of converting steviol to one or more steviol glycosides. In certain embodiments, the host cell further comprises one, two, three, four, or more enzymes together capable of converting steviol to RebA. In certain embodiments, the host cell further comprises one or more enzymes capable of converting RebA to RebD. In certain embodiments, the host cell further comprises one or more enzymes capable of converting RebD to RebM. Useful enzymes and nucleic acids encoding the enzymes are known to those of skill. Particularly useful enzymes and nucleic acids are described in the sections below and further described, for example, in US 2014/0329281 A1, US 2014/0357588 A1, US 2015/0159188, WO 2016/038095 A2, and US 2016/0198748 A1.

In further embodiments, the host cells further comprise one or more enzymes capable of making geranylgeranyl diphosphate from a carbon source. These include enzymes of the DXP pathway and enzymes of the MEV pathway. Useful enzymes and nucleic acids encoding the enzymes are known to those of skill in the art. Exemplary enzymes of each pathway are described below and further described, for example, in US 2016/0177341 A1.

In some embodiments, the host cells comprise one or more or all of the isoprenoid pathway enzymes selected from the group consisting of: (a) an enzyme that condenses two molecules of acetyl-coenzyme A to form acetoacetyl-CoA (e.g., an acetyl-coA thiolase); (b) an enzyme that condenses acetoacetyl-CoA with another molecule of acetyl-CoA to form 3-hydroxy-3-methylglutaryl-CoA (HMG-CoA) (e.g., an HMG-CoA synthase); (c) an enzyme that converts HMG-CoA into mevalonate (e.g., an HMG-CoA reductase); (d) an enzyme that converts mevalonate into mevalonate 5-phosphate (e.g., a mevalonate kinase); (e) an enzyme that converts mevalonate 5-phosphate into mevalonate 5-pyrophosphate (e.g., a phosphomevalonate kinase); (f) an enzyme that converts mevalonate 5-pyrophosphate into isopentenyl diphosphate (IPP) (e.g., a mevalonate pyrophosphate decarboxylase); (g) an enzyme that converts IPP into dimethylallyl pyrophosphate (DMAPP) (e.g., an IPP isomerase); (h) a polyprenyl synthase that can condense IPP and/or DMAPP molecules to form polyprenyl compounds containing more than five carbons; (i) an enzyme that condenses IPP with DMAPP to form geranyl pyrophosphate (GPP) (e.g., a GPP synthase); (j) an enzyme that condenses two molecules of IPP with one molecule of DMAPP (e.g., an FPP synthase); (k) an enzyme that condenses IPP with GPP to form farnesyl pyrophosphate (FPP) (e.g., an FPP synthase); (l) an enzyme that condenses IPP and DMAPP to form geranylgeranyl pyrophosphate (GGPP); and (m) an enzyme that condenses IPP and FPP to form GGPP.

In certain embodiments, the additional enzymes are native. In advantageous embodiments, the additional enzymes are heterologous. In certain embodiments, two or more enzymes can be combined in one polypeptide.

5.3 Cell Strains

Host cells useful compositions and methods provided herein include archae, prokaryotic, or eukaryotic cells.

Suitable prokaryotic hosts include, but are not limited to, any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma*,

*Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans,* or *Hansenula polymorpha* (now known as *Pichia angusta*). In some embodiments, the host microbe is a strain of the genus *Candida,* such as *Candida lipolytica, Candida guilliermondii, Candida krusei, Candida pseudotropicalis,* or *Candida utilis.*

In a particular embodiment, the host microbe is *Saccharomyces cerevisiae.* In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

5.4 The Steviol and Steviol Glycoside Biosynthesis Pathways

In some embodiments, a steviol biosynthesis pathway and/or a steviol glycoside biosynthesis pathway is activated in the genetically modified host cells provided herein by engineering the cells to express polynucleotides and/or polypeptides encoding one or more enzymes of the pathway. FIG. 1 illustrates an exemplary steviol biosynthesis pathway.

Thus, in some embodiments, the genetically modified host cells provided herein comprise a heterologous polynucleotide encoding a polypeptide having geranylgeranyl diphosphate synthase (GGPPS) activity. In some embodiments, the genetically modified host cells provided herein comprise a heterologous polynucleotide encoding a polypeptide having copalyl diphosphate synthase or ent-copalyl pyrophosphate synthase (CDPS; also referred to as ent-copalyl pyrophosphate synthase or CPS) activity. In some embodiments, the genetically modified host cells provided herein comprise a heterologous polynucleotide encoding a polypeptide having kaurene synthase (KS; also referred to as ent-kaurene synthase) activity. In particular embodiments, the genetically modified host cells provided herein comprise a heterologous polynucleotide encoding a polypeptide having kaurene oxidase activity (KO; also referred to as ent-kaurene 19-oxidase) as described herein. In particular embodiments, the genetically modified host cells provided herein comprise a heterologous polynucleotide encoding a polypeptide having kaurenoic acid hydroxylase polypeptide activity (KAH; also referred to as steviol synthase) according to the embodiments provided herein. In some embodiments, the genetically modified host cells provided herein comprise a heterologous polynucleotide encoding a polypeptide having cytochrome P450 reductase (CPR) activity.

In some embodiments, the genetically modified host cells provided herein comprise a heterologous polynucleotide encoding a polypeptide having UGT74G1 activity. In some embodiments, the genetically modified host cells provided herein comprise a heterologous polynucleotide encoding a polypeptide having UGT76G1 activity. In some embodiments, the genetically modified host cells provided herein comprise a heterologous polynucleotide encoding a polypeptide having UGT85C2 activity. In some embodiments, the genetically modified host cells provided herein comprise a heterologous polynucleotide encoding a polypeptide having UGT91D activity. In some embodiments, the genetically modified host cells provided herein comprise a heterologous polynucleotide encoding a polypeptide having UGTAD activity. As described below, UGTAD refers to a uridine diphosphate-dependent glycosyl transferase capable of transferring a glucose moiety to the C-2' position of the 19-O-glucose of RebA to produce RebD.

In certain embodiments, the host cell comprises a variant enzyme. In certain embodiments, the variant can comprise up to 15, 10, 9, 8, 7, 6, 5, 4, 3, 2, or 1 amino acid substitutions relative to the relevant polypeptide. In certain embodiments, the variant can comprise up to 15, 10, 9, 8, 7, 6, 5, 4, 3, 2, or 1 conservative amino acid substitutions relative to the reference polypeptide. In certain embodiments, any of the nucleic acids described herein can be optimized for the host cell, for instance codon optimized.

Exemplary nucleic acids and enzymes of a steviol biosynthesis pathway and/or a steviol glycoside biosynthesis pathway are described below.

5.4.1 Geranylgeranyl Diphosphate Synthase (GGPPS)

Geranylgeranyl diphosphate synthases (EC 2.5.1.29) catalyze the conversion of farnesyl pyrophosphate into geranylgeranyl diphosphate. Illustrative examples of enzymes include those of *Stevia rebaudiana* (accession no. ABD92926), *Gibberella fujikuroi* (accession no. CAA75568), *Mus musculus* (accession no. AAH69913), *Thalassiosira pseudonana* (accession no. XP_002288339), *Streptomyces clavuligerus* (accession no. ZP_05004570), *Sulfulobus acidocaldarius* (accession no. BAA43200), *Synechococcus* sp. (accession no. ABC98596), *Arabidopsis thaliana* (accession no. NP_195399), *Blakeslea trispora* (accession no. AFC92798.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these GGPPS nucleic acids. In certain embodiments, provided herein are cells and methods using a nucleic acid that encodes a polypeptide having at least 80%, 85%, 90%, 95% sequence identity to at least one of these GGPPS enzymes.

5.4.2 Copalyl diphosphate synthase (CDPS)

Copalyl diphosphate synthases (EC 5.5.1.13) catalyze the conversion of geranylgeranyl diphosphate into copalyl diphosphate. Illustrative examples of enzymes include those of *Stevia rebaudiana* (accession no. AAB87091), *Streptomyces clavuligerus* (accession no. EDY51667), *Bradyrhizobium japonicum* (accession no. AAC28895.1), *Zea mays* (accession no. AY562490), *Arabidopsis thaliana* (accession no. NM_116512), *Oryza sativa* (accession no. Q5MQ85.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS nucleic acids. In certain embodiments, provided herein are cells and methods using a nucleic acid that encodes a polypeptide having at least 80%, 95%, 90%, or 95% sequence identity to at least one of these CDPS enzymes.

5.4.3 Kaurene Synthase (KS)

Kaurene synthases (EC 4.2.3.19) catalyze the conversion of copalyl diphosphate into kaurene and diphosphate. Illustrative examples of enzymes include those of *Bradyrhizobium japonicum* (accession no. AAC28895.1), *Phaeosphaeria* sp. (accession no. 013284), *Arabidopsis thaliana* (accession no. Q9SAK2), *Picea glauca* (accession no. ADB55711.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these KS nucleic acids. In certain embodiments, provided herein are cells and methods using a nucleic acid that encodes a polypeptide having at least 80%, 85%, 85%, 90%, or 95% sequence identity to at least one of these KS enzymes.

5.4.4 Bifunctional Copalyl Diphosphate Synthase (CDPS) and Kaurene Synthase (KS)

CDPS-KS bifunctional enzymes (EC 5.5.1.13 and EC 4.2.3.19) also can be used. Illustrative examples of enzymes include those of *Phomopsis amygdali* (accession no. BAG30962), *Physcomitrella patens* (accession no. BAF61135), *Gibberella fujikuroi* (accession no. Q9UVY5.1), and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS-KS nucleic acids. In certain embodiments, provided herein are cells and methods using a nucleic acid that encodes a polypeptide having at least 80%, 85%, 90%, or 95% sequence identity to at least one of these CDPS-KS enzymes.

5.4.5 Ent-Kaurene Oxidase (KO)

Ent-kaurene oxidases (EC 1.14.13.78; also referred to as kaurene oxidases herein) catalyze the conversion of kaurene into kaurenoic acid. Illustrative examples of enzymes include those of *Oryza sativa* (accession no. Q5Z5R4), *Gibberella fujikuroi* (accession no. 094142), *Arabidopsis thaliana* (accession no. Q93ZB2), *Stevia rebaudiana* (accession no. AAQ63464.1), *Pisum sativum* (Uniprot no. Q6XAF4) and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these KO nucleic acids. In certain embodiments, provided herein are cells and methods using a nucleic acid that encodes a polypeptide having at least 80%, 85%, 90%, or 95% sequence identity to at least one of these KO enzymes.

5.4.6 Steviol Synthase (KAH)

Modified steviol synthases, or kaurenoic acid hydroxylases (KAH), (EC 1.14.13.79) are provided herein. Nucleic acids encoding these enzymes are useful in the cells and methods provided herein.

5.4.7 Cytochrome P450 Reductase (CPR)

Cytochrome P450 reductases (EC 1.6.2.4) are necessary for the activity of KO and/or KAH above. Illustrative examples of enzymes include those of *Stevia rebaudiana* (accession no. ABB88839)*Arabidopsis thaliana* (accession no. NP_194183), *Gibberella fujikuroi* (accession no. CAE09055), *Artemisia annua* (accession no. ABC47946.1) and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CPR nucleic acids. In certain embodiments, provided herein are cells and methods using a nucleic acid that encodes a polypeptide having at least 80%, 85%, 90%, or 95% sequence identity to at least one of these CPR enzymes.

5.4.8 UDP Glycosyltransferase 74G1 (UGT74G1)

A UGT74G1 is capable of functioning as a uridine 5'-diphospho glucosyl: steviol 19-COOH transferase and as a uridine 5'-diphospho glucosyl: steviol-13-O-glucoside 19-COOH transferase. As shown in FIG. 1, a UGT74G1 is capable of converting steviol to 19-glycoside. A UGT74G1 is also capable of converting steviolmonoside to rubusoside. A UGT74G1 may be also capable of converting steviolbioside to stevioside. Illustrative examples of enzymes include those of *Stevia rebaudiana* (e.g., those of Richman et al., 2005, *Plant J.* 41: 56-67 and US 2014/0329281 and WO 2016/038095 A2 and accession no. AAR06920.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT74G1 nucleic acids. In certain embodiments, provided herein are cells and methods using a nucleic acid that encodes a polypeptide having at least 80%, 85%, 90%, or 95% sequence identity to at least one of these UGT74G1 enzymes. 5.4.9 UDP glycosyltransferase 76G1 (UGT76G1)

A UGT76G1 is capable of transferring a glucose moiety to the C-3' of the C-13-O-glucose of the acceptor molecule, a steviol 1,2 glycoside. Thus, a UGT76G1 is capable of functioning as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. UGT76G1 is capable of converting steviolbioside to RebB. A UGT76G1 is also capable of converting stevioside to RebA. A UGT76G1 is also capable of converting RebD to RebM. Illustrative examples of enzymes include those of *Stevia rebaudiana* (e.g., those of Richman et al., 2005, *Plant J.* 41: 56-67 and US 2014/0329281 A1 and WO 2016/038095 A2 and accession no. AAR06912.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT76G1 nucleic acids. In certain embodiments, provided herein are cells and methods using a nucleic acid that encodes a polypeptide having at least 80%, 85%, 90%, or 95% sequence identity to at least one of these UGT76G1 enzymes.

5.4.10 UDP Glycosyltransferase 85C2 (UGT85C2)

A UGT85C2 is capable of functioning as a uridine 5'-diphospho glucosyl:steviol 13-OH transferase, and a uridine 5'-diphospho glucosyl: steviol-19-O-glucoside 13-OH transferase. A UGT85C2 is capable of converting steviol to steviolmonoside, and is also capable of converting 19-glycoside to rubusoside. Illustrative examples of enzymes include those of Stevia rebaudiana (e.g., those of Richman et al., 2005, Plant J. 41: 56-67 and US 2014/0329281 A1 and WO 2016/038095 A2 and accession no. AAR06916.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT85C2 nucleic acids. In certain embodiments, provided herein are cells and methods using a nucleic acid that encodes a polypeptide having at least 80%, 85%, 90%, or 95% sequence identity to at least one of these UGT85C2 enzymes.

5.4.11 UDP-Glycosyltransferase 91D (UGT91D)

A UGT91D is capable of functioning as a uridine 5'-diphosphoglucosyl:steviol-13-0-glucoside transferase, transferring a glucose moiety to the C-2' of the 13-O-glucose of the acceptor molecule, steviol-13-O-glucoside (steviolmonoside) to produce steviobioside. A UGT91D is also capable of functioning as a uridine 5'-diphosphoglucosyl: rubusoside transferase, transferring a glucose moiety to the C-2' of the 13-O-glucose of the acceptor molecule, rubusoside, to provide stevioside. A UGT91D is also referred to as UGT91D2, UGT91D2e, or UGT91D-like3. Illustrative examples of UGT91D enzymes include those of Stevia rebaudiana (e.g., those of UGT sequence with accession no. ACE87855.1, US 2014/0329281 A1, WO 2016/038095 A2, and SEQ ID NO:7). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT91D nucleic acids. In certain embodiments, provided herein are cells and methods using a nucleic acid that encodes a polypeptide having at least 80%, 85%, 90%, or 95% sequence identity to at least one of these UGT91D enzymes.

5.4.12 Uridine Diphosphate-Dependent Glycosyl Transferase Capable of Converting RebA to RebD (UGTAD)

A uridine diphosphate-dependent glycosyl transferase ($UGT_{AD}$) is capable of transferring a glucose moiety to the C-2' position of the 19-O-glucose of RebA to produce RebD. A $UGT_{AD}$ is also capable of transferring a glucose moiety to the C-2' position of the 19-O-glucose of stevioside to produce RebE. Useful examples of UGTs include Os_UGT_91C1 from Oryza sativa (also referred to as EUGT11 in Houghton-Larsen et al., WO 2013/022989 A2; XP_015629141.1) and Sl_UGT_101249881 from Solanum lycopersicum (also referred to as UGTSL2 in Markosyan et al., WO2014/193888 A1; XP_004250485.1). Further useful UGTs include UGT40087 (XP_004982059.1; as described in WO 2018/031955), sr.UGT_9252778, Bd UGT10840 (XP_003560669.1), Hv_UGT_V1 (BAJ94055.1), Bd UGT10850 (XP_010230871.1), and Ob_UGT91B1_like (XP_006650455.1). Any UGT or UGT variant can be used in the compositions and methods described herein. Nucleic acids encoding these enzymes are useful in the cells and methods provided herein. In certain embodiments, provided herein are cells and methods using a nucleic acid having at least 80%, 85%, 90%, or 95% sequence identity to at least one of the UGTs. In certain embodiments, provided herein are cells and methods using a nucleic acid that encodes a polypeptide having at least 80%, 85%, 90%, or 95% sequence identity to at least one of these UGTs. In certain embodiments, provided herein are a nucleic acid that encodes a UGT variant described herein.

5.5 MEV Pathway FPP and/or GGPP Production

In some embodiments, a genetically modified host cell provided herein comprises one or more heterologous enzymes of the MEV pathway, useful for the formation of FPP and/or GGPP. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate. In some embodiments, the one or more enzymes of the MEV pathway comprise an enzyme that converts isopentenyl pyrophosphate to dimethylallyl diphosphate.

In some embodiments, the one or more enzymes of the MEV pathway are selected from the group consisting of acetyl-CoA thiolase, acetoacetyl-CoA synthetase, HMG-CoA synthase, HMG-CoA reductase, mevalonate kinase, phosphomevalonate kinase, mevalonate pyrophosphate decarboxylase, and isopentyl diphosphate:dimethylallyl diphosphate isomerase (IDI or IPP isomerase). In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate. In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway. In some embodiments, the host cell comprises one or more heterologous nucleotide sequences encoding seven enzymes of the MEV pathway. In some embodiments, the host cell comprises a plurality of heterologous nucleic acids encoding all of the enzymes of the MEV pathway.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprises a heterologous nucleic acid encoding an enzyme that can modify IPP or a polyprenyl to form an isoprenoid compound such as FPP.

5.5.1 Conversion of Acetyl-CoA to Acetoacetyl-CoA

In some embodiments, the genetically modified host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include but are not limited to: (NC_000913 REGION: 2324131.2325315; *Escherichia coli*), (D49362; *Paracoccus denarificans*), and (L20428; *Saccharomyces cerevisiae*).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In host cells comprising acetyl-CoA thiolase and a heterologous ADA and/or phosphotransacetylase (PTA), the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Similarly, the activity of PTA is reversible, and thus, a large acetyl-CoA pool may drive PTA towards the reverse reaction of converting acetyl-CoA to acetyl phosphate. Therefore, in some embodiments, in order to provide a strong pull on acetyl-CoA to drive the forward reaction of ADA and PTA, the MEV pathway of the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci USA* 107(25):11265-70 (2010). Representative AACS nucleotide sequences of *Streptomyces* sp. strain CL190 include accession number AB540131.1. Representative AACS protein sequences of *Streptomyces* sp. strain CL190 include accession numbers D7URVO, BAJ10048. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988 (AB212624; BAE78983); Actinoplanes sp. A40644 (AB113568; BAD07381); *Streptomyces* sp. C (NZ_ACEW010000640; ZP_05511702); *Nocardiopsis dassonvillei* DSM 43111 (NZ_ABUI01000023; ZP_04335288); *Mycobacterium ulcerans* Agy99 (NC_008611; YP_907152); *Mycobacterium marinum* M (NC_010612; YP_001851502); *Streptomyces* sp. Mg1 (NZ_DS570501; ZP_05002626); *Streptomyces* sp. AA4 (NZ_ACEV01000037; ZP_05478992); *S. roseosporus* NRRL 15998 (NZ_ABYB01000295; ZP_04696763); *Streptomyces* sp. ACTE (NZ_ADFD01000030; ZP_06275834); *S. viridochromogenes* DSM 40736 (NZ ACEZ01000031; ZP_05529691); *Frankia* sp. CcI3 (NC_007777; YP_480101); *Nocardia brasiliensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

5.5.2 Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., an HMG-CoA synthase. Illustrative examples of nucleotide sequences encoding such an enzyme include but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

5.5.3 Conversion of HMG-CoA to Mevalonate

In some embodiments, the host cell comprises a heterologous nucleotide sequence encoding an enzyme that can convert HMG-CoA into mevalonate, e.g., an HMG-CoA reductase. In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMG-CoA reductases are provided below.

Co-Factor Specificities for Select Class II HMG-CoA Reductases

| Source | Coenzyme specificity | $K_m^{NADPH}$ (µM) | $K_m^{NADH}$ (µM) |
|---|---|---|---|
| P. mevalonii | NADH | | 80 |
| A. fulgidus | NAD(P)H | 500 | 160 |
| S. aureus | NAD(P)H | 70 | 100 |
| E. faecalis | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii, A. fulgidus* or *S. aureus*. In particular embodiments, the HMG-CoA reductase is capable of only utilizing NADH as a cofactor, e.g., HMG-CoA reductase from *P. mevalonii, S. pomeroyi* or *D. acidovorans*.

In some embodiments, the NADH-using HMG-CoA reductase is from *Pseudomonas* mevalonii. The sequence of the wild-type mvaA gene of *Pseudomonas* mevalonii, which encodes HMG-CoA reductase (EC 1.1.1.88), has been previously described. See Beach and Rodwell, *J. Bacteriol.* 171:2994-3001 (1989). Representative mvaA nucleotide sequences of *Pseudomonas* mevalonii include accession number M24015. Representative HMG-CoA reductase protein sequences of *Pseudomonas* mevalonii include accession numbers AAA25837, P13702, MVAA PSEMV.

In some embodiments, the NADH-using HMG-CoA reductase is from *Silicibacter pomeroyi*. Representative HMG-CoA reductase nucleotide sequences of *Silicibacter pomeroyi* include accession number NC_006569.1. Representative HMG-CoA reductase protein sequences of *Silicibacter pomeroyi* include accession number YP_164994.

In some embodiments, the NADH-using HMG-CoA reductase is from *Delftia acidovorans*. A representative HMG-CoA reductase nucleotide sequences of *Delftia acidovorans* includes NC_010002 REGION: complement (319980 . . . 321269). Representative HMG-CoA reductase protein sequences of *Delftia acidovorans* include accession number YP_001561318.

In some embodiments, the NADH-using HMG-CoA reductases is from *Solanum tuberosum* (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$ ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteriol.* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171: 2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGR and an NADPH-using HMG-CoA reductase.

Illustrative examples of nucleotide sequences encoding an NADPH-using HMG-CoA reductase include, but are not limited to: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

5.5.4 Conversion of Mevalonate to Mevalonate-5-Phosphate

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

5.5.5 Conversion of Mevalonate-5-Phosphate to Mevalonate-5-Pyrophosphate

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

5.5.6 Conversion of Mevalonate-5-Pyrophosphate to IPP

In some embodiments, the host cell comprises a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

5.5.7 Conversion of IPP to DMAPP

In some embodiments, the host cell further comprises a heterologous nucleotide sequence encoding an enzyme that can convert IPP generated via the MEV pathway into dimethylallyl pyrophosphate (DMAPP), e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

5.5.8 Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Menthaxpiperita*), (AF182827; *Menthaxpiperita*), (MPI249453; *Menthaxpiperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar *Copenhageni* str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisiae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa* Temecula1).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ AAJM01000380, Locus ZP_00743052; *Bacillus thuringiensis* serovar *israelensis*, ATCC 35646 sq1563), (CRGGPPS; *Catharanthus roseus*), (NZ AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides* f *lusitanicus*), (AB016044; *Mus musculus*), (AABX01000298, Locus NCU01427; *Neurospora crassa*), (NCU20940; *Neurospora crassa*), (NZ AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

While examples of the enzymes of the mevalonate pathway are described above, in certain embodiments, enzymes of the DXP pathway can be used as an alternative or additional pathway to produce DMAPP and IPP in the host cells, compositions and methods described herein. Enzymes and nucleic acids encoding the enzymes of the DXP pathway are well-known and characterized in the art, e.g., WO 2012/135591 A2.

5.6 Methods of Producing Steviol Glycosides

In another aspect, provided herein is a method for the production of a steviol glycoside, the method comprising the steps of: (a) culturing a population of any of the genetically modified host cells described herein that are capable of producing a steviol glycoside in a medium with a carbon source under conditions suitable for making the steviol glycoside compound; and (b) recovering said steviol glycoside compound from the medium.

In some embodiments, the genetically modified host cell produces an increased amount of the steviol glycoside compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, and/or productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of a steviol glycoside that is greater than about 1 gram per liter of fermentation medium. In some embodiments, the host cell produces an elevated level of a steviol glycoside that is greater than about 5 grams per liter of fermentation medium. In some embodiments, the host cell produces an elevated level of a steviol glycoside that is greater than about 10 grams per liter of fermentation medium. In some embodiments, the steviol glycoside is produced in an amount from about 10 to about 50 grams, from about 10 to about 15 grams, more than about 15 grams, more than about 20 grams, more than about 25 grams, or more than about 30 grams per liter of cell culture.

In some embodiments, the host cell produces an elevated level of a steviol glycoside that is greater than about 50 milligrams per gram of dry cell weight. In some such embodiments, the steviol glycoside is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by a parent cell, on a per unit volume of cell culture basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit volume of cell culture per unit time basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight per unit time basis.

In most embodiments, the production of the elevated level of steviol glycoside by the host cell is inducible by the presence of an inducing compound. Such a host cell can be manipulated with ease in the absence of the inducing compound. The inducing compound is then added to induce the production of the elevated level of steviol glycoside by the host cell. In other embodiments, production of the elevated level of steviol glycoside by the host cell is inducible by changing culture conditions, such as, for example, the growth temperature, media constituents, and the like.

5.7 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing steviol glycosides provided herein may be performed in a suitable culture medium (e.g., with or without pantothenate supplementation) in a suitable container, including but not limited to a cell culture plate, a microtiter plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing an steviol glycoside can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium is sufficient to promote cell growth, but is not so high as to repress growth of the microorganism used. Typically, cultures are run with a carbon source, such as glucose, being added at levels to achieve the desired level of growth and biomass. In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

In some embodiments, the culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or steviol glycoside production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of steviol glycoside. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. The carbon source concentration is typically maintained below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

5.8 Fermentation Compositions

In another aspect, provided herein are fermentation compositions comprising a genetically modified host cell described herein and steviol glycosides produced from genetically modified host cell. The fermentation compositions may further comprise a medium. In certain embodiments, the fermentation compositions comprise a genetically modified host cell, and further comprise RebA, RebD, and RebM. In certain embodiments, the fermentation compositions provided herein comprise RebM as a major component of the steviol glycosides produced from the genetically modified host cell. In certain embodiments, the fermentation compositions comprise RebA, RebD, and RebM at a ratio of at least 1:7:50. In certain embodiments, the fermentation compositions comprise RebA, RebD, and RebM at a ratio of at least 1:7:50 to 1:100:1000. In certain embodiments, the fermentation compositions comprise a ratio of at least 1:7:50 to 1:200:2000. In certain embodiments, the ratio of RebA, RebD, and RebM are based on the total content of steviol glycosides that are associated with the genetically modified host cell and the medium. In certain embodiments, the ratio of RebA, RebD, and RebM are based on the total content of steviol glycosides in the medium. In certain embodiments, the ratio of RebA, RebD, and RebM are based on the total content of steviol glycosides that are associated with the genetically modified host cell.

In certain embodiments, the fermentation compositions provided herein contain RebM2 at an undetectable level. In certain embodiments, the fermentation compositions provided herein contain non-naturally occurring steviol glycosides at an undetectable level.

5.9 Recovery of Steviol Glycosides

Once the steviol glycoside is produced by the host cell, it may be recovered or isolated for subsequent use using any suitable separation and purification methods known in the art. In some embodiments, a clarified aqueous phase comprising the steviol glycoside is separated from the fermentation by centrifugation. In other embodiments, a clarified aqueous phase comprising the steviol glycoside is separated from the fermentation by adding a demulsifier into the fermentation reaction. Illustrative examples of demulsifiers include flocculants and coagulants.

The steviol glycoside produced in these cells may be present in the culture supernatant and/or associated with the host cells. In embodiments where some of the steviol glycoside is associated with the host cell, the recovery of the steviol glycoside may comprise a method of improving the release of the steviol glycosides from the cells. In some embodiments, this could take the form of washing the cells with hot water or buffer treatment, with or without a surfactant, and with or without added buffers or salts. In some embodiments, the temperature is any temperature deemed suitable for releasing the steviol glycosides. In some embodiments, the temperature is in a range from 40 to 95° C.; or from 60 to 90° C.; or from 75 to 85° C. In some embodiments, the temperature is 40, 45, 50, 55, 65, 70, 75, 80, 85, 90, or 95° C. In some embodiments physical or chemical cell disruption is used to enhance the release of steviol glycosides from the host cell. Alternatively and/or subsequently, the steviol glycoside in the culture medium can be recovered using an isolation unit operations including, but not limited to solvent extraction, membrane clarification, membrane concentration, adsorption, chromatography, evaporation, chemical derivatization, crystallization, and drying.

5.10 Methods of Making Genetically Modified Cells

Also provided herein are methods for producing a host cell that is genetically engineered to comprise one or more of the modifications described above, e.g., one or more nucleic heterologous nucleic acids encoding *Stevia rebaudiana* kaurenoic acid hydroxylase, and/or biosynthetic pathway enzymes, e.g., for a steviol glycoside compound. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell. In other embodiments, the nucleic acid is a linear piece of double stranded DNA that can integrate via homology the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc; CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The amount of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, KAN$^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the KAN$^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however, it will be recognized that absolute identity to such genes is not necessary. For example, changes in a particular gene or polynucleotide comprising a sequence encoding a polypeptide or enzyme can be performed and screened for activity. Typically, such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp (www.idtdna.com/CodonOptfrom) from Integrated DNA Technologies.

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum, Kluyveromyces* spp., including *K. thermotolerans, K. lactis,* and *K. marxianus, Pichia* spp., *Hansenula* spp., including *H. polymorpha, Candida* spp., *Trichosporon* spp., *Yamadazyma* spp., including *Y.* spp. *Torulaspora pretoriensis, Issatchenkia orientalis, Schizosaccharomyces* spp., including *S. pombe, Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous UDP glycosyltransferases, KAH, or any biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology,* 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above-mentioned databases in accordance with the teachings herein.

VI. EXAMPLES

Example 1: Yeast Culturing Conditions

Each DNA construct was integrated into *Saccharomyces cerevisiae* (CEN.PK113-7D) using standard molecular biology techniques in an optimized lithium acetate transformation. Briefly, cells were grown overnight in yeast extract peptone dextrose (YPD) media at 30° C. with shaking (200 rpm), diluted to an OD600 of 0.1 in 100 mL YPD, and grown to an OD600 of 0.6-0.8. For each transformation, 5 mL of culture were harvested by centrifugation, washed in 5 mL of sterile water, spun down again, resuspended in 1 mL of 100 mM lithium acetate, and transferred to a microcentrifuge tube. Cells were spun down (13,000× g) for 30 s, the supernatant was removed, and the cells were resuspended in a transformation mix consisting of 240 μl 50% PEG, 36 μl 1 M lithium acetate, 10 μl boiled salmon sperm DNA, and 74 μl of donor DNA. For transformations that require expression of the endonuclease F-Cph1, the donor DNA included a plasmid carrying the F-Cph1 gene expressed under the yeast TDH3 promoter. F-Cph1 endonuclease expressed in such a manner cuts a specific recognition site engineered in a host strain to facilitate integration of the target gene of interest. Following a heat shock at 42° C. for 40 min, cells were recovered overnight in YPD media before plating on selective media. DNA integration was confirmed by colony PCR with primers specific to the integrations.

Example 2: Generation of a Base Strain Capable of High Flux to Farnesylpyrophosphate (FPP) and the Isoprenoid Farnesene A farnesene production strain was created from a wild type *Saccharomyces cerevisiae* strain (CEN.PK113-7D) by expressing the genes of the mevalonate pathway under the control of native GAL promoters. This strain comprised the following chromosomally integrated mevalonate pathway genes from *S. cerevisiae*: acetyl-CoA thiolase, HMG-CoA synthase, HMG-CoA reductase, mevalonate kinase, phosphomevalonate kinase, mevalonate pyrophosphate decarboxylase, and IPP:DMAPP isomerase. In addition, the strain contained multiple copies of farnesene synthase from *Artemisia annua*, also under the control of either native GAL1 or GAL10 promoters. All heterologous genes described herein were codon optimized using publicly available or other suitable algorithms. The strain also contained a deletion of the GAL80 gene, and the ERG9 gene encoding squalene synthase is downregulated by replacing the native promoter with the promoter of the yeast gene MET3. Examples of methods of creating *S. cerevisiae* strains with high flux to isoprenoids are described in the U.S. Pat. Nos. 8,415,136 and 8,236,512 which are incorporated herein in their entireties.

Example 3: Construction of a Series of Strains for Rapid Screening for Novel Kaurenoic Acid Hydroxylase P450 Enzymes FIG. 1 shows an exemplary biosynthetic pathway from FPP to Reb M with the kaurenoic acid intermediate. The farnesene base strain described above was further engineered to have high flux to the C20 isoprenoid kaurene by integrating six copies of a geranyl¬geranyl¬pyro¬phosphate synthase (GGPPS) into the genome, one copy of a copalyl¬diphosphate synthase, and four copies of a kaurene synthase. Subsequently, all copies of farnesene synthase were removed from the strain and the strain was confirmed to produce ent-kaurene and no farnesene.

Kaurenoic acid hydroxylase (KAH) is a cytochrome P450 enzyme that catalyzes the oxidation of kaurenoic acid to produce steviol (see FIG. 1) which is necessary to produce Reb M. To screen novel P450 enzymes for KAH activity in vivo in *S. cerevisiae*, several strains were made that contained all the genes necessary to produce Reb M, except they lacked any copy of a KAH gene. Table 1 lists all Reb M pathway genes and promoters used. The strains containing all genes described in Table 1 primarily produce kaurenoic acid, the substrate for KAH.

TABLE 1

Genes, promoters, and amino acid sequences of the enzymes used to convert FPP to Reb M.

| Enzyme | SEQ ID | Promoter |
| --- | --- | --- |
| Bt.GGPPS | SEQ ID NO: 7 | PGAL1 |
| Ent-Os.CDPS | SEQ ID NO: 8* | PGAL1 |
| Ent-Pg.KS | SEQ ID NO: 9 | PGAL1 |
| Sr.KO | SEQ ID NO: 6 | PGAL1 |
| At.CPR | SEQ ID NO: 11 | PGAL3 |
| UGT85C2 | SEQ ID NO: 12 | PGAL10 |
| UGT74G1 | SEQ ID NO: 13 | PGAL1 |
| UGT91D_like3 | SEQ ID NO: 14 | PGAL1 |
| UGT76G1 | SEQ ID NO: 15 | PGAL10 |
| UGT40087 | SEQ ID NO: 16 | PGAL1 |

*First 65 amino acids replaced with a single methionine.

To measure the activity of KAH variants in vivo in *S. cerevisiae*, initially a first screening strain was constructed that contains all the genes necessary to produce the monoglycosylated steviol metabolite 19-glycoside (Table 1 and FIG. 1), except that it lacks any copy of a KAH gene. Instead, it contains a landing pad to allow for the rapid insertion of KAH variants (FIG. 2). The landing pad consists of 500 bp of locus-targeting DNA sequences on either end of the construct to the genomic region upstream and downstream of the yeast locus of choice (Upstream locus and Downstream locus), thereby deleting the locus when the landing pad is integrated into the yeast chromosome. Internally, the landing pad contains a promoter (Promoter) which can be GAL1, GAL3 or any other promoter of yeast GAL regulon and a yeast terminator of choice (Terminator) flanking an endonuclease recognition site (F-CphI). DNA variants of Sr.KAH (SEQ ID NO: 1) were used to transform the strain along with a plasmid expressing endonuclease F-Cph1, which cuts the recognition sequence, creating a double strand break at the landing pad, and facilitating homologous recombination of the Sr. KAH DNA variants at the site.

A second screening strain was derived from the first screening strain that lacks a functional KAH gene by introducing additional genes to ultimately contain all the genes necessary to produce Reb M (Table 1 and FIG. 1). As with the first screening strain, the second screening strain lacks any copy of a KAH gene and contains a cleavable landing pad (FIG. 2) instead.

A third screening strain was generated that has the same engineering as the second screening strain except the Sr.KO was replaced with Ps.KO (SEQ ID NO: 10). The Ps.KO enzyme is described in PCT/US2018/046359 (PISUM SATIVUM KAURENE OXIDASE FOR HIGH EFFICIENCY PRODUCTION OF REBAUDIOSIDES filed Aug. 10, 2018) and is significantly more active in converting kaurene to kaurenoic acid (FIG. 1). The third screening strain therefore has a higher carbon flux to kaurenoic acid, the substrate of the KAH P450. The second and third screening strains are referred to as Reb M producing yeast that lack a functional KAH gene.

Example 4: Yeast Culturing Conditions

Yeast colonies verified to contain the expected KAH gene were picked into 96-well microtiter plates containing Bird Seed Media (BSM, originally described by van Hoek et al.,

*Biotechnology and Bioengineering* 68(5), 2000, pp. 517-523) with 20 g/L sucrose, 37.5 g/L ammonium sulfate, and from 1 to 5 g/L lysine. Cells were cultured at 30° C. in a high capacity microtiter plate incubator shaking at 1000 rpm and 80% humidity for 3 days until the cultures reached carbon exhaustion. The growth-saturated cultures were subcultured into fresh plates containing BSM with 40 g/L sucrose, 150 g/L ammonium sulfate, and 1 g/L lysine by taking 14.4 μL from the saturated cultures and diluting into 360 μL of fresh media. Cells in the production media were cultured at 30° C. in a high capacity microtiter plate shaker at 1000 rpm and 80% humidity for additional 3 days prior to extraction and analysis.

Example 5: Yeast Sample Preparation Conditions for Analysis of Pathway Intermediates from Farnesol to Rebaudioside M To extract all steviol glycosides made by cells (see FIG. 1), upon culturing completion, the whole cell broth was diluted with 628 μL of 100% ethanol, sealed with a foil seal, and shaken at 1250 rpm for 30 s. 314 μL of water was added to each well directly to dilute the extraction. The plate was briefly centrifuged to pellet solids. 198 μL of 50:50 ethanol:water containing 0.48 mg/L rebaudioside N (used as an internal standard) was transferred to a new 250 μL assay plate and 2 μL of the culture/ethanol mixture was added to the assay plate. A foil seal was applied to the plate for analysis.

To extract pathway intermediates from farnesol to steviol (see FIG. 1) made by cells, upon culturing completion, the whole cell broth was diluted with 100 μl of 100% methanol, and 500 μL of 100% ethyl acetate, sealed with a foil seal, and shaken at 1000 rpm for 30 min to extract the analytes of interest into the ethyl acetate. The mixture was centrifuged to pellet any solids. 150 μL of the ethyl acetate layer is added to a new 1.1 mL assay plate and 150 μL of fresh ethyl acetate layer added to the assay plate followed by GC-FID analysis.

Example 6: Analytical Methods

Samples for steviol glycosides measurements were analyzed by mass spectrometer (Agilent 6470-QQQ) with a RapidFire 365 system autosampler with C8 cartridge.

TABLE 2

| RapidFire 365 system configuration. | |
|---|---|
| Pump 1, Line A: 2 mM ammonium formate in water | 100% A, 1.5 mL/min |
| Pump 2, Line A: 35% acetonitrile in water | 100% A, 1.5 mL/min |
| Pump 3, Line A: 80% acetonitrile in water | 100% A, 0.8 mL/min |
| State 1: Aspirate | 600 ms |
| State 2: Load/Wash | 3000 ms |
| State 3: Extra wash | 1500 ms |
| State 4: Elute | 5000 ms |
| State 5: Reequilibrate | 1000 ms |

TABLE 3

| 6470-QQQ MS method configurations. | |
|---|---|
| Ion Source | AJS ESI |
| Time Filtering peak width | 0.02 min |
| Stop Time | No limit/as pump |
| Scan Type | MRM |
| Diverter Valve | To MS |
| Delta EMV | (+)0/(−)300 |
| Ion Mode (polarity) | Negative |
| Gas Temp | 250° C. |
| Gas Flow | 11 L/min |
| Nebulizer | 30 psi |
| Sheath Gas Temp | 350° C. |
| Sheath Gas Flow | 11 L/min |
| Negative Capillary V | 2500 V |

The peak areas from a chromatogram from a mass spectrometer were used to generate the calibration curve using authentic standards. The molar ratios of relevant compounds were determined by quantifying the amount in moles of each compound through external calibration using an authentic standard, and then taking the appropriate ratios.

Samples upstream of steviol glycosides (i.e. farnesol through steviol, FIG. 1) were analyzed by gas chromatography with flame ionization detection (GC-FID, Agilent 7890A) using an Agilent DB-17MS (20 m×0.18 mm×0.18 μm, P/N 121-4722) in split mode with a split ratio of 50. The following temperature and flow gradients were used:

TABLE 4

| Temperature gradient. | |
|---|---|
| Initial Temp, (° C.) | 140 |
| Initial Hold, (min) | 0.0 |
| Rate 1, (° C./min) | 15 |
| Temp 1, (° C.) | 175 |
| Hold Time 1, (min) | 0.0 |
| Rate 2, (° C./min) | 100 |
| Temp 2, (° C.) | 320 |
| Hold Time 2, (min) | 2.0 |
| Runtime (min) | 6.21 |

TABLE 5

| Flow gradient. | |
|---|---|
| Carrier gas | Hydrogen |
| Pressure, psi | 47.2 |
| Flow, mL/min at t = 0 min | 3.0 |
| Velocity, cm/s | 85.05 |
| Mode | Ramped flow |
| Flow 1, (mL/min) | 3.0 |
| Hold Time 1, (min) | 5.5 |
| Rate 2, (mL/min/min) | 10.0 |
| Flow 2 (mL/min) | 5.0 |
| Hold Time 2, (min) | 0.0 |

Each analyte was identified by retention time, determined from an authentic standard. The peak areas from a chromatogram are used to generate the calibration curve. The molar ratio of kaurene, kaurenol, kaurenal, kaurenoic acid, and steviol were determined by quantifying the amount in moles of each compound through external calibration using an authentic standard, and then taking the appropriate ratios.

Example 7: Evolution of *Stevia rebaudiana* Kaurenoic Acid Hydroxylase Via Site Directed Saturation Mutagenesis In this example, activity data is provided for a P450 enzyme (kaurenoic acid hydroxylase from the plant *Stevia rebaudiana*, Sr.KAH) and specific mutations that improve Sr.KAH activity expressed in *S. cerevisiae* in vivo to produce steviol glycosides and Reb M.

KAH is a cytochrome P450 enzyme that catalyzes the oxidation of kaurenoic acid to steviol (FIG. 1) which is necessary for the formation of Reb M. Each amino acid residue in Sr.KAH was mutated to 12 different amino acids (R, N, D, C, G, H, I, L, F, S, Y, and V) that are coded by the degenerate codon NDT where N stands for any (nucleotide adenine, thymine, guanine and cytosine); D stands for adenine, guanine and thymine; and T stands for thymine. The NDT library of Sr.KAH gene variants was constructed via PCR using primers containing an NDT degenerate codon at the desired position. Each PCR product contains a mixture of gene variants so that 12 possible different amino acids are encoded at a specific position corresponding to a single protein residue. In each PCR product, the pool of Sr.KAH gene variants are flanked on both ends by 40 bp of sequences homologous to the promoter (at 5' of the gene) and the terminator (at 3' of the gene) regions of the landing pad incorporated at the specific locus of *S. cerevisiae* host strain (see FIG. 2).

To measure the activity of KAH variants generated in the first round of site saturation mutagenesis in *S. cerevisiae* in vivo, the mutated Sr.KAH variants were used to transform either a 19-glycoside producing yeast or a Reb M producing yeast that lacked functional KAH genes. Wild type Sr.KAH was used as a control. The in vivo KAH activity was measured in an initial Tier 1 screen as the titer of either 19-glycoside or Reb M, respectively. In the Tier 1 screen, twenty-four isolates were screened per mutated codon position giving a 2× coverage at N=1.

For screening in the 19-glycoside producing yeast, the effect of each mutation was calculated by normalizing the amount of 19-glycoside produced in a strain containing an Sr.KAH mutant allele to the amount of 19-glycoside produced by a strain containing the wild type Sr.KAH allele. For screening in Reb M producing yeast, all the steviol glycosides produced by a strain were extracted and measured via mass spectrometry. The sum of all the steviol glycosides was calculated (in μM); this measurement is called the "steviol equivalent." The effect of a mutation was calculated by normalizing the steviol equivalent of a strain containing a Sr.KAH mutant allele to the steviol equivalent of a strain containing the wild type Sr.KAH allele.

Upon finding mutations in Tier 1 that appear to increase activity of the Sr.KAH enzyme in vivo, a Tier 2 screen was performed with higher replication (N=12) of strains containing a specific mutant of interest to confirm the improvement, using the same calculations as above. The resulting Sr.KAH mutants, each containing a single amino acid change, that have activity at least one standard deviation higher than the wild type Sr.KAH allele is reported in FIG. 3 and Table 6 as the fold increase in steviol equivalents over the wild type parent Sr.KAH allele. For example, if a mutant strain has 2-fold (2×) higher activity, then it produced double the amount (or 100% more) of measured steviol glycosides (steviol equivalents) over a strain with wild type Sr.KAH. The best mutant from the site directed saturation mutagenesis NDT library (G306L) provides a 2.7-fold improvement of in vivo KAH activity compared to wild type Sr.KAH.

TABLE 6

Improved alleles of Sr.KAH: the associated amino acid changes and fold improvement over wild type Sr.KAH activity.

| Sr.KAH sequence variations compared to wild type | Fold improvement over wt Sr.KAH | Percent improvement over wt Sr.KAH |
| --- | --- | --- |
| wild type Sr.KAH | 1.00 | 0 |
| Y62H | 1.39 | 39 |
| T164R | 1.43 | 43 |
| L76V | 1.45 | 45 |
| Q415L | 1.47 | 47 |
| A60Y | 1.49 | 49 |
| S182C | 1.52 | 52 |
| T167N | 1.52 | 52 |
| Y52H | 1.54 | 54 |
| R266D | 1.57 | 57 |
| T167H | 1.58 | 58 |
| I153L | 1.59 | 59 |
| K100L | 1.60 | 60 |
| G306C | 1.64 | 64 |
| Q120N | 1.65 | 65 |
| L232H | 1.65 | 65 |
| I333V | 1.66 | 66 |
| G351R | 1.68 | 68 |
| L232S | 1.69 | 69 |
| I166S | 1.74 | 74 |
| W447C | 1.75 | 75 |
| I443Y | 1.76 | 76 |
| I166N | 1.82 | 82 |
| N355Y | 1.83 | 83 |
| L232D | 1.84 | 84 |
| S158D | 1.86 | 86 |
| A442G | 1.86 | 86 |
| G306N | 1.96 | 96 |
| V316L | 2.02 | 102 |
| M308L | 2.03 | 103 |
| G447F | 2.14 | 114 |
| G306I | 2.21 | 121 |
| G306V | 2.22 | 122 |
| I350L | 2.35 | 135 |
| G447V | 2.44 | 144 |
| I166R | 2.62 | 162 |
| G306L | 2.70 | 170 |

Example 8: Combinatorial Library of Single Mutations to Improve Sr.KAH Activity

Two sets of 12 mutations were selected from the unique NDT library hits to build full factorial combination libraries. Each set contained nine of the same mutations and three unique mutations per set. The first combinatorial library contained mutations K100L, Q120N, I153L, S158D, I166R, L232D, G306L, V316L, I333V, I350L, A442G, G447V, and the second library contained mutations S158D, I166R, L232D, G306L, M308L, V316L, I333V, I350L, N355Y, A442G, I443Y, G447V. The libraries were designed to create all possible combinations among the 12 mutations to find the combination that leads to the highest activity of Sr.KAH in vivo. The genes were assembled from a mixture of custom built gBlocks (Integrated DNA Technologies, Inc.) with overlapping homology on the ends of each piece so that the pieces overlapped in sequence; assembling all the pieces together reconstituted a full length KAH allele. The terminal 5' and 3' pieces also had homology to the promoter and terminator of the landing pad sequence in Reb M producing yeast that lack a functional KAH gene. The pieces were transformed into yeast and relied on endogenous homologous recombination to assemble the pieces together.

The Tier 1 combinatorial library DNA was screened in the Reb M producing yeast at a 2× coverage. The top 10 KAH alleles from the combination library screen were PCRamplified and the DNA was used to transform a Reb M producing yeast as a Tier 2 confirmation at N=4 replication. The simplest, improved KAH combinatorial variant contained two mutations at I166R and I333V and was 4.3-fold improved in comparison to wild type Sr.KAH. The top combinatorial KAH mutants improved total steviol production 5-fold and 6.3-fold over wild type Sr.KAH (FIG. 4 and Table 7). The best combination of amino acid substitutions (6.3× improvement over wild type Sr. KAH in the Reb M producing yeast) comprised the mutations S158D, I166R, G306L, M308L, V316L, and I350L.

Improved KAH mutants show a reduction in the substrate kaurenoic acid compared to wild type Sr.KAH (FIG. 5), again demonstrating that Sr.KAH alleles with improved activity are converting more substrate to steviol, thereby increasing Reb M production in yeast in vivo. In FIG. 5, the amount of kaurenoic acid is normalized to that in the strain containing wild type Sr.KAH (100%). The reduction in kaurenoic acid levels in the yeast containing improved Sr.KAH alleles is shown as a percent of the kaurenoic acid levels in wild type Sr.KAH. The Sr.KAH allele with the most improved activity has kaurenoic acid levels that are 40% of the amount of kaurenoic acid that is observed in strains with wild type Sr.KAH.

is unlikely to be closely associated with the catalytic domain, and the N-terminal domain is not required for function. However, interactions between the P450 catalytic domain and the ER membrane are important for protein activity. For example, interactions with the ER membrane could promote the transfer of hydrophobic substrates from the membrane to the catalytic site and could also orient the protein to facilitate interaction with a cytochrome P450 reductase (CPR), which is necessary for activity.

While not intending to be bound by any theory of operation, we discovered that swapping the ER-associated N-terminus of a P450 protein with other N-terminal transmembrane domains could lead to an improvement in heterologously expressed plant P450 activity in *S. cerevisiae*. Swapping N-terminal transmembrane domains should not disturb the ER-targeting, nor should it change the specificity of the catalytic domain, but it might help with ER localization of the heterologous protein and/or it might alter the protein conformation to improve the interactions of the catalytic domain with the ER membrane. This latter effect could lead to improved interactions with ER-bound substrates or the ER-bound CPRs.

This example provides activity data for the wild type kaurenoic acid hydroxylase from the plant *Stevia rebaudi-*

TABLE 7

Improved alleles of Sr.KAH, fold improvement over wild type Sr.KAH activity, and the associated amino acid changes.

| Sr.KAH alleles | Fold improvement over wt Sr.KAH | Percent improvement over wt Sr.KAH | List of sequence variations compared to wild type | | | | |
|---|---|---|---|---|---|---|---|
| wild type Sr.KAH | 1.00 | 0 | | | | | |
| mutant #1 | 4.34 | 334 | I166R | I333V | | | |
| mutant #2 | 4.98 | 398 | I166R | I350L | G447V | | |
| mutant #3 | 5.11 | 411 | I153L | S158D | I166R | L232D | I333V | I350L |
| mutant #4 | 5.58 | 458 | S158D | G306L | I350L | | |
| mutant #5 | 5.8 | 480 | G306L | V316L | I350L | G447V | |
| mutant #6 | 5.88 | 488 | G306L | V316L | I333V | I350L | |
| mutant #7 | 5.95 | 495 | S158D | I166R | L232D | G306L | I333V |
| mutant #8 | 5.96 | 496 | L232D | G306L | V316L | I333V | I350L |
| mutant #9 | 6.16 | 516 | I166R | L232D | G306L | I350L | |
| mutant #10 | 6.36 | 536 | S158D | I166R | G306L | M308L | V316L | I350L |

Example 9: N-Terminal Domain Swaps to Improve In Vivo Activity of Wild Type Sr.KAH This example provides modified kaurenoic acid hydroxylase polypeptides with substituted N-terminal domains that show improved activity.

Kaurenoic acid hydroxylase is a cytochrome P450 enzyme. Most eukaryotic P450s are membrane-bound proteins, and the high-level domain structure of membrane-associated cytochrome P450 enzymes is highly conserved. Plant cytochrome P450 enzymes are incorporated into the endoplasmic reticulum (ER) with a long N-terminal polypeptide chain of roughly 30-50 amino acids that mediates membrane targeting. The catalytic domain of the P450 enzymes face the cytoplasmic side of the endoplasmic reticulum. The region of the N-terminus that is inserted into the ER membrane stops at the end of a hydrophobic stretch of roughly 20 amino acid residues and precedes the catalytic domain. A short region that generally contains positively charged residues links the catalytic domain to a conserved proline rich motif in the N-terminus of the structurally conserved P450 fold. The N-terminal ER-targeting domain

*ana* (Sr.KAH) in which the native N-terminal transmembrane domain was swapped with the N-terminal transmembrane domain of other ER-bound proteins, including, but not limited to, other cytochrome P450 enzymes and cytochrome P450 reductases (CPRs).

To make the chimeric proteins, wild type Sr. KAH and the candidate ER-bound proteins were truncated at various positions, such as (1) the proline rich region, (2) the transmembrane domain site predicted from a TMHMM server (available at www.cbs.dtu.dk/services/TMHMM/), (3) the positively charged residues embedded approximately around amino acid number 30-50 of the N-terminus, or (4) based on sequence alignment. The N-terminal region from the candidate proteins was then added to the truncated Sr.KAH protein containing the catalytic domain.

To screen for activity, the genes of the chimeric proteins were used to transform a Reb M producing yeast that lack a functional KAH gene described above; wild type Sr.KAH (SEQ ID NO:1, which corresponds to sequence identification no. 164 in EP 3009508) was used as the control.

Two separate methods were used to calculate KAH P450 function. The first was to take the ratio of total Reb M made in the cell with a chimera protein over the total Reb M made in the cell with wild type Sr.KAH. The second method to calculate P450 function was to sum in µM all the steviol glycosides made in the cell with a chimera protein over the total steviol glycosides in µM made in the cell with wild type Sr.KAH. This latter measure of "steviol equivalents" is more accurate, since it calculates all the steviol made in the cell, even if some intermediates remain and do not get converted all the way to Reb M.

Each chimera was ranked by its total steviol equivalents ratio to the wild type Sr.KAH. The N-terminal domains from plant CPR ATR2 and plant *Stevia rebaudiana* kaurene oxidase (Sr.KO) showed equal or improved activity relative to wild type Sr.KAH (Table 8).

TABLE 8

Improved alleles of wild type Sr.KAH derivatives resulting from N-terminal domain swaps, fold improvement over wild type Sr.KAH activity, and the associated amino acid changes.

| Polypeptide | Length of N-terminal deletion (aa) of Sr.KAH | Length of new N-terminus added | Source of new N-terminus | Reb M ratio chimera/wt Sr.KAH | Total steviol glycosides ratio chimera/wt Sr.KAH |
| --- | --- | --- | --- | --- | --- |
| wild type Sr.KAH (SEQ ID NO: 1; control) | 0 | 0 | NA | 1.00 | 1.00 |
| ATR2(1a:72a): Sr.KAH(23a:500a) SEQ ID NO: 2 | 22 | 72 | ATR2 | 1.28 | 1.35 |
| ATR2(1a:50a): Sr.KAH(5a:500a) SEQ ID NO: 3 | 4 | 50 | ATR2 | 1.16 | 1.29 |
| Sr.KO(1a:23a): Sr.KAH(5a:500a) SEQ ID NO: 5 | 4 | 23 | Sr.KO | 1.16 | 1.01 |

Example 10: N-Terminal Domain Swaps to Improve In Vivo Activity of the Best Evolved Variant of Sr.KAH, Mutant #10

The amino acid mutations found in most improved combinatorial Sr.KAH variant in Example 8, mutant #10, were combined with the three N-terminal domain swaps in Example 9, Table 8 that increased total steviol equivalents. Chimeras were made exactly as described in Example 9, only instead of using wild type Sr.KAH DNA sequence, the DNA sequence of mutant #10 from Example 8 was used. All the mutations in Sr.KAH mutant #10 were retained in the resulting N-terminal domain-swapped chimeras. The new chimeric genes, containing the evolved amino acid mutations, were transformed into Reb M producing yeast. The evolved Sr.KAH mutant #10 was used as the experimental control. The effect of the N-terminal domain swaps on activity of Sr.KAH mutant #10 was calculated exactly as was described in Example 9. Fusion of N-terminus sequence from two genes, the CPRs from *Artemisia annua* (Aa.CPR) and *Arabidopsis thaliana* (ATR2), to the N-terminally truncated Sr.KAH mutant #10 resulted in improvements as high as 60% in KAH enzymatic activity (Table 9).

TABLE 9

Alleles of evolved Sr.KAH mutant #10 resulting from N-terminal domain swaps, fold improvement over Sr.KAH mutant #10 activity, and the associated amino acid changes.

| Polypeptide | Length of N-terminal deletion (aa) of Sr.KAH mutant #10 | Length of new N-terminus added | Source of new N-terminus | Reb M ratio chimera/ Sr.KAH mutant #10 | Total steviol glycosides ratio chimera/ Sr.KAH mutant #10 |
| --- | --- | --- | --- | --- | --- |
| Sr.KAH mutant #10 (control) | 0 | 0 | NA | 1.00 | 1.00 |
| Aa.CPR(1a:66a): Sr.KAH_mutant#10(23a:500a) SEQ ID NO: 21 | 22 | 66 | Aa.CPR | 1.53 | 1.58 |
| ATR2(1a:72a): Sr.KAH_mutant#10(23a:500a) SEQ ID NO: 2 | 22 | 72 | ATR2 | 1.60 | 1.63 |

Example 11: N-Terminal Domain Swaps to Improve In Vivo Activity of Evolved Variant of Sr.KAH, Mutant #3

To test whether beneficial N-terminal domain swaps identified in Examples 9 and 10 can be utilized to improve the activity of other Sr.KAH variants, beneficial amino acid mutations from another improved variant, Sr.KAH mutant #3 (Example 8), were combined with two best N-terminal domain swaps identified in Example 10. The resulting chimeric genes were used to transform Reb M producing yeast that lack a functional KAH gene and titers of Reb M and total steviol glycosides were analyzed (Table 10). Fusion of N-terminus sequence from two genes, the CPRs from *Artemisia annua* (Aa.CPR) and *Arabidopsis thaliana* (ATR2), to the 22 amino acid N-terminally truncated Sr.KAH mutant #3 resulted in improvements of approximately 25% in this strain background.

TABLE 10

Alleles of evolved Sr.KAH mutant #3 resulting from N-terminal domain swaps, fold improvement over Sr.KAH mutant #3 activity, and the associated amino acid changes.

| Polypeptide | Length of N-terminal deletion (aa) of Sr.KAH mutant #3 | Length of new N-terminus added | Source of new N-terminus | Reb M ratio chimera/ Sr.KAH mutant #3 | Total steviol glycosides ratio chimera/ Sr.KAH mutant #3 |
|---|---|---|---|---|---|
| Sr.KAH mutant #3 (control) | 0 | 0 | NA | 1.00 | 1.00 |
| Aa.CPR(1a:66a): Sr.KAH_mutant#3(23a:500a) SEQ ID NO: 24 | 22 | 66 | Aa.CPR | 1.24 | 1.26 |
| ATR2(1a:72a): Sr.KAH_mutant#3(23a:500a) SEQ ID NO: 25 | 22 | 72 | ATR2 | 1.27 | 1.28 |

Example 12: N-Terminal Domain Swaps with Native Yeast ER Proteins to Improve In Vivo Activity of Evolved Variant of Sr.KAH, Mutant #10

One of the topology characters shared by the two beneficial transmembrane domains derived from Aa.CPR and ATR2 in Examples 10 and 11 is an approximately 50 amino acid long sequence predicted to be inside the endoplasmic reticulum (ER) lumen preceding the first transmembrane helix. There are 15 proteins in *S. cerevisiae* documented in the Membranome data base (available at membranome.org/) having a single-helix transmembrane domain at their N-terminus. Scanning these 15 protein sequences using the TMHMM server (available at www.cbs.dtu.dk/services/TMHMM/) revealed several such N-terminal sequences resembling the pattern shared by transmembrane domains from Aa.CPR and ATR2. These include ERG11(1a:80a), ERG11(1a:51a), ALG11(1a:45a), SEC66(1a:50a), NUS1 (1a:119a), RCR1(1a:62a), and UBP1(1a:52a).

The fusions of these N-terminal, native yeast sequences N-terminally truncated Sr.KAH mutant #10 were created. The chimeric gene sequences were inserted into Reb M producing yeast that lack a functional KAH gene and titers of Reb M and total steviol glycosides were analyzed as described in Example 8.

Among the seven chimeric genes tested, two chimeras containing SEC66(1a:50a) and UBP1(1a:52a) were improved in comparison to Sr.KAH mutant #10 by approximately 20%. Three N-terminal sequences, ERG11(1a:80a), NUS1(1a:119a), and RCR1(1a:62a), apparently disrupted the function of KAH, whereas two, ALG11(1a:45a) and ERG11(1a:51a), had no significant effect on activity (Table 11).

TABLE 11

Alleles of evolved Sr.KAH mutant #10 resulting from native yeast N-terminal domain swaps, fold improvement over Sr.KAH mutant #10 activity, and the associated amino acid changes.

| Polypeptide | Length N-terminal deletion (aa) of Sr.KAH mutant #10 | Length of new N-terminus added | Source of new N-terminus | Reb M ratio chimera/ Sr.KAH mutant #10 | Total steviol glycosides ratio chimera/ Sr.KAH mutant #10 |
|---|---|---|---|---|---|
| Sr.KAH mutant #10 (control) | 0 | 0 | NA | 1.00 | 1.00 |
| ALG11(1a:45a): Sr.KAH_mutant#10(23a:1503a) SEQ ID NO: 26 | 22 | 45 | ALG11 | 1.06 | 1.08 |
| ERG11(1a:51a): Sr.KAH_mutant#10(23a:500a) SEQ ID NO: 27 | 22 | 51 | ERG11 | 1.05 | 1.07 |
| ERG11(1a:80a): Sr.KAH_mutant#10(47a:500a) SEQ ID NO: 28 | 46 | 80 | ERG11 | 0.25 | 0.23 |

TABLE 11-continued Alleles of evolved Sr.KAH mutant #10 resulting from native yeast N-terminal domain swaps, fold improvement over Sr.KAH mutant #10 activity, and the associated amino acid changes.

| Polypeptide | Length N-terminal deletion (aa) of Sr.KAH mutant #10 | Length of new N-terminus added | Source of new N-terminus | Reb M ratio chimera/ Sr.KAH mutant #10 | Total steviol glycosides ratio chimera/ Sr.KAH mutant #10 |
|---|---|---|---|---|---|
| NUS1(1a:119a): Sr.KAH_mutant#10(23a:500a) SEQ ID NO: 29 | 22 | 119 | NUS1 | 0.41 | 0.38 |
| RCR1(1a:62a): Sr.KAH_mutant#10(23a:500a) SEQ ID NO: 30 | 22 | 62 | RCR1 | 0.04 | 0.04 |
| SEC66(1a:50a): Sr.KAH_mutant#10(23a:500a) SEQ ID NO: 31 | 22 | 50 | SEC66 | 1.16 | 1.19 |
| UBP1(1a:52a): Sr.KAH_mutant#10(23a:500a) SEQ ID NO: 32 | 22 | 52 | UBP1 | 1.18 | 1.20 |

Importantly, the results of Examples 9, 10, 11, and 12 demonstrate that swapping the N-terminal, ER-associated protein domain of cytochrome P450 enzymes improves cytochrome P450 enzyme activity when expressing the P450 enzyme in a heterologous host.

Example 13: Further Improvement of Sr.KAH Mutant #3 Via Site Directed Saturation Mutagenesis To further improve the activity of Sr.KAH mutant #3 (Example 8) another round of site directed saturation mutagenesis was applied and mutant variants with even higher activity in converting kaurenoic acid to steviol (FIG. 1) were isolated. Each of 175 selected positions (E2, A3, S4, Y5, L6, Y7, I8, I10, L11, L12, L13, L14, A15, S16, Y17, L18, F19, T20, T21, Q22, L23, R24, R25, K26, S27, A28, N29, L30, F35, S37, I38, I40, I41, H43, L46, L47, K49, Y52, T54, K57, I58, A60, Y62, L66, Q67, L68, L70, G71, Y72, R74, L76, S80, P81, S82, E85, C87, T89, N91, V93, I94, F95, N97, K100, L102, K105, I106, V107, T110, S114, S116, D119, Q120, N123, V127, S129, I130, I132, V135, H136, N139, D143, R145, N149, R150, L151, L153, R157, D158, S160, S161, T164, L165, R166, T167, V168, L172, L174, I177, S182, D191, R192, S215, G218, I223, L227, V229, K230, D232, K235, I237, G249, R258, G259, A260, K261, V262, G263, K264, G265, R266, G295, G306, M308, V316, V333, N336, I339, I344, G345, L350, G351, N355, S373, A374, S379, N382, I383, G386, L389, V391, H397, T408, Q415, G416, L417, G419, T420, R421, D422, G423, F424, K425, L426, M427, S431, G432, R433, G440, A442, I443, L445, G447, M448, V453, V462, L473, V484, P489, S491, E492, T494, N495, L496, L497, and S498) in the Sr.KAH mutant #3 sequence was mutated to 15 different amino acids (A, C, D, F, G, H, I, L, N, P, R, S—encoded by two codons—, T, V, and Y) that are encoded by the degenerate codon NNT where N stands for any nucleotide adenine, thymine, guanine and cytosine and T stands for thymine. The NNT library of Sr.KAH gene variants was constructed via PCR using primers containing an NNT degenerate codon at the desired position as described in Example 7 and used to transform Reb M producing yeast that lack a functional KAH gene for integration at the landing pad for expression of KAH.

The in vivo KAH activity of the NNT library mutants was measured in a Tier 1 screen versus the Sr.KAH mutant #3 allele using the titer of total steviol glycosides (μM) as described in Example 7. Thirty-nine isolates were screened per mutated position in the protein sequence giving approximately a 2.5× coverage at N=1 for each unique variant. Upon finding mutations in Sr. KAH mutant #3 that appear to increase activity of the enzyme in vivo, a Tier 2 screen was performed with higher replication (N=10) of strains containing a specific mutant of interest to confirm the improvement, using the same calculations as described in Example 7. The resulting activity of an NNT-derived mutant Sr.KAH allele is reported in fold increase over Sr.KAH mutant #3 in FIG. 6 and Table 12.

TABLE 12

Improved alleles of Sr.KAH mutant #3: the associated amino acid changes and fold improvement over Sr.KAH mutant #3 activity.

| Sr.KAH sequence variations compared to Sr.KAH mutant #3 | Fold improvement over Sr.KAH mutant #3 | Percent improvement over Sr.KAH mutant #3 |
|---|---|---|
| Sr.KAH mutant #3 | 1.00 | 0 |
| E492C | 1.17 | 17 |
| M427A | 1.18 | 18 |
| G306D | 1.19 | 19 |
| V333C | 1.19 | 19 |
| D191L | 1.21 | 21 |
| I40S | 1.21 | 21 |
| L445I | 1.21 | 21 |
| S114A | 1.23 | 23 |
| D191Y | 1.26 | 26 |
| D191F | 1.35 | 35 |
| L497R | 1.46 | 46 |
| G306L | 1.48 | 48 |
| N29G | 1.8 | 80 |
| T167G | 2.09 | 109 |
| T164S | 2.23 | 123 |
| Q415H | 2.6 | 160 |
| T89A | 2.71 | 171 |
| L13D | 3.11 | 211 |
| R258T | 3.65 | 265 |
| L13V | 4.28 | 328 |

Twenty mutations were identified that lead to improvements in activity, ranging from 17% to 4-fold over Sr.KAH mutant #3. The best mutant from this site directed saturation mutagenesis NNT library (L13V) provides 4.3-fold improvement of in vivo KAH activity comparing to Sr.KAH mutant #3 (which is already improved 5-fold over wild type Sr.KAH, Example 8). Interestingly, this conservative mutation (both leucine and valine have small hydrophobic side chains) is at the N-terminus of the protein where alterations via domain swap had significant effects on protein activity (Examples 9-12). Another beneficial mutation, N29G also belongs in the N-terminal domain of Sr.KAH. It is also interesting that the composition of mutations that improve the activity of wild type Sr.KAH (Example 7) is very different from those improving the activity of Sr.KAH mutant #3 (this Example). Mutant #3 differs by six amino acids from wild type Sr.KAH, with G306L being the only mutation beneficial for both enzyme variants: top hit for wild type and 9th best for mutant #3 of Sr.KAH.

All publications, patents and patent applications cited in this specification are herein incorporated by reference as if each individual publication or patent application were specifically and individually indicated to be incorporated by reference. Although the claims have been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A kaurenoic acid hydroxylase polypeptide with residue numbers according to SEQ ID NO: 1, comprising:
one, two, three, four, five, six, seven, eight, nine, or ten, of the following mutations: I166R, I153L, S158D, G306L, L232D, I333V, I350L, V316L, G447V, and M308L,
wherein the kaurenoic acid hydroxylase polypeptide is capable of increased conversion of kaurenoic acid to steviol compared to a kaurenoic acid hydroxylase polypeptide of SEQ ID NO:1.

2. The kaurenoic acid hydroxylase polypeptide of claim 1 comprising the following mutations:
(a) I166R and I333V,
(b) I166R, I350L, and G447V,
(c) I153L, S158D, I166R, L232D, I333V, and I350L,
(d) S158D, G306L, and I350L,
(e) G306L, V316L, I350L, and G447V,
(f) G306L, V316L, I333V, and I350,
(g) S158D, I166R, L232D, G306L, and I333V,
(h) L232D, G306L, V316L, I333V, and I350,
(i) I166R, L232D, G306L, and I350L, or
(j) S158D, I166R, G306L, M308L, V316L, and I350L.

3. The kaurenoic acid hydroxylase polypeptide of claim 1, further comprising at least one mutation at kaurenoic acid hydroxylase positions E492C, M427A, G306D, V333C, D191L, I40S, L445I, S114A, D191Y, D191F, L497R, G306L, N29G, T167G, T164S, Q415H, T89A, L13D, R258T, and L13V, wherein the residue numbers are according to SEQ ID NO: 1.

* * * * *

SEQUENCE LISTING

```
<160> NUMBER OF SEQ ID NOS: 40

<210> SEQ ID NO 1
<211> LENGTH: 500
<212> TYPE: PRT
<213> ORGANISM: Stevia rebaudiana
<220> FEATURE:
<221> NAME/KEY: misc_feature
<222> LOCATION: (1)..(500)
<223> OTHER INFORMATION: wild type Stevia rebaudiana kaurenoic acid
      hydroxylase

<400> SEQUENCE: 1

Met Glu Ala Ser Tyr Leu Tyr Ile Ser Ile Leu Leu Leu Leu Ala Ser
1               5                   10                  15

Tyr Leu Phe Thr Thr Gln Leu Arg Arg Lys Ser Ala Asn Leu Pro Pro
                20                  25                  30

Thr Val Phe Pro Ser Ile Pro Ile Ile Gly His Leu Tyr Leu Leu Lys
            35                  40                  45

Lys Pro Leu Tyr Arg Thr Leu Ala Lys Ile Ala Ala Lys Tyr Gly Pro
        50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
                165                 170                 175

Ile Met Arg Met Ile Ser Gly Lys Arg Tyr Phe Asp Ser Gly Asp Arg
            180                 185                 190

Glu Leu Glu Glu Gly Lys Arg Phe Arg Glu Ile Leu Asp Glu Thr
        195                 200                 205

Leu Leu Leu Ala Gly Ala Ser Asn Val Gly Asp Tyr Leu Pro Ile Leu
    210                 215                 220

Asn Trp Leu Gly Val Lys Ser Leu Glu Lys Lys Ile Ala Leu Gln
225                 230                 235                 240

Lys Lys Arg Asp Asp Phe Phe Gln Gly Leu Ile Glu Gln Val Arg Lys
                245                 250                 255
```

```
Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
    290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
    370                 375                 380

Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
            420                 425                 430

Arg Arg Gly Cys Pro Gly Glu Gly Leu Ala Ile Arg Leu Leu Gly Met
        435                 440                 445

Thr Leu Gly Ser Val Ile Gln Cys Phe Asp Trp Glu Arg Val Gly Asp
    450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
            500

<210> SEQ ID NO 2
<211> LENGTH: 550
<212> TYPE: PRT
<213> ORGANISM: Artificial Sequence
<220> FEATURE:
<223> OTHER INFORMATION: Synthetic: ATR2(1a:72a):Sr.KAH(23a:500a)

<400> SEQUENCE: 2

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
                20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
        50                  55                  60

Gly Cys Ile Val Met Leu Val Trp Leu Arg Arg Lys Ser Ala Asn Leu
65                  70                  75                  80

Pro Pro Thr Val Phe Pro Ser Ile Pro Ile Ile Gly His Leu Tyr Leu
                85                  90                  95

Leu Lys Lys Pro Leu Tyr Arg Thr Leu Ala Lys Ile Ala Ala Lys Tyr
            100                 105                 110
```

```
Gly Pro Ile Leu Gln Leu Gln Leu Gly Tyr Arg Arg Val Leu Val Ile
        115                 120                 125

Ser Ser Pro Ser Ala Ala Glu Glu Cys Phe Thr Asn Asn Asp Val Ile
130                 135                 140

Phe Ala Asn Arg Pro Lys Thr Leu Phe Gly Lys Ile Val Gly Gly Thr
145                 150                 155                 160

Ser Leu Gly Ser Leu Ser Tyr Gly Asp Gln Trp Arg Asn Leu Arg Arg
                165                 170                 175

Val Ala Ser Ile Glu Ile Leu Ser Val His Arg Leu Asn Glu Phe His
                180                 185                 190

Asp Ile Arg Val Asp Glu Asn Arg Leu Leu Ile Arg Lys Leu Arg Ser
        195                 200                 205

Ser Ser Ser Pro Val Thr Leu Ile Thr Val Phe Tyr Ala Leu Thr Leu
210                 215                 220

Asn Val Ile Met Arg Met Ile Ser Gly Lys Arg Tyr Phe Asp Ser Gly
225                 230                 235                 240

Asp Arg Glu Leu Glu Glu Gly Lys Arg Phe Arg Glu Ile Leu Asp
        245                 250                 255

Glu Thr Leu Leu Leu Ala Gly Ala Ser Asn Val Gly Asp Tyr Leu Pro
                260                 265                 270

Ile Leu Asn Trp Leu Gly Val Lys Ser Leu Glu Lys Lys Leu Ile Ala
        275                 280                 285

Leu Gln Lys Lys Arg Asp Asp Phe Phe Gln Gly Leu Ile Glu Gln Val
        290                 295                 300

Arg Lys Ser Arg Gly Ala Lys Val Gly Lys Gly Arg Lys Thr Met Ile
305                 310                 315                 320

Glu Leu Leu Leu Ser Leu Gln Glu Ser Glu Pro Glu Tyr Tyr Thr Asp
                325                 330                 335

Ala Met Ile Arg Ser Phe Val Leu Gly Leu Leu Ala Ala Gly Ser Asp
                340                 345                 350

Thr Ser Ala Gly Thr Met Glu Trp Ala Met Ser Leu Leu Val Asn His
            355                 360                 365

Pro His Val Leu Lys Lys Ala Gln Ala Glu Ile Asp Arg Val Ile Gly
        370                 375                 380

Asn Asn Arg Leu Ile Asp Glu Ser Asp Ile Gly Asn Ile Pro Tyr Ile
385                 390                 395                 400

Gly Cys Ile Ile Asn Glu Thr Leu Arg Leu Tyr Pro Ala Gly Pro Leu
                405                 410                 415

Leu Phe Pro His Glu Ser Ser Ala Asp Cys Val Ile Ser Gly Tyr Asn
                420                 425                 430

Ile Pro Arg Gly Thr Met Leu Ile Val Asn Gln Trp Ala Ile His His
        435                 440                 445

Asp Pro Lys Val Trp Asp Asp Pro Glu Thr Phe Lys Pro Glu Arg Phe
450                 455                 460

Gln Gly Leu Glu Gly Thr Arg Asp Gly Phe Lys Leu Met Pro Phe Gly
465                 470                 475                 480

Ser Gly Arg Arg Gly Cys Pro Gly Glu Gly Leu Ala Ile Arg Leu Leu
                485                 490                 495

Gly Met Thr Leu Gly Ser Val Ile Gln Cys Phe Asp Trp Glu Arg Val
                500                 505                 510

Gly Asp Glu Met Val Asp Met Thr Glu Gly Leu Gly Val Thr Leu Pro
                515                 520                 525
```

```
Lys Ala Val Pro Leu Val Ala Lys Cys Lys Pro Arg Ser Glu Met Thr
            530                 535                 540
Asn Leu Leu Ser Glu Leu
545                 550

<210> SEQ ID NO 3
<211> LENGTH: 546
<212> TYPE: PRT
<213> ORGANISM: Artificial Sequence
<220> FEATURE:
<223> OTHER INFORMATION: Synthetic: ATR2(1a:50a):Sr.KAH(5a:500a)

<400> SEQUENCE: 3

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
            35                  40                  45

Asn Arg Tyr Leu Tyr Ile Ser Ile Leu Leu Leu Ala Ser Tyr Leu
            50                  55                  60

Phe Thr Thr Gln Leu Arg Arg Lys Ser Ala Asn Leu Pro Pro Thr Val
65                  70                  75                  80

Phe Pro Ser Ile Pro Ile Ile Gly His Leu Tyr Leu Leu Lys Lys Pro
                85                  90                  95

Leu Tyr Arg Thr Leu Ala Lys Ile Ala Ala Lys Tyr Gly Pro Ile Leu
            100                 105                 110

Gln Leu Gln Leu Gly Tyr Arg Arg Val Leu Val Ile Ser Ser Pro Ser
            115                 120                 125

Ala Ala Glu Glu Cys Phe Thr Asn Asn Asp Val Ile Phe Ala Asn Arg
130                 135                 140

Pro Lys Thr Leu Phe Gly Lys Ile Val Gly Gly Thr Ser Leu Gly Ser
145                 150                 155                 160

Leu Ser Tyr Gly Asp Gln Trp Arg Asn Leu Arg Arg Val Ala Ser Ile
                165                 170                 175

Glu Ile Leu Ser Val His Arg Leu Asn Glu Phe His Asp Ile Arg Val
            180                 185                 190

Asp Glu Asn Arg Leu Leu Ile Arg Lys Leu Arg Ser Ser Ser Ser Pro
            195                 200                 205

Val Thr Leu Ile Thr Val Phe Tyr Ala Leu Thr Leu Asn Val Ile Met
            210                 215                 220

Arg Met Ile Ser Gly Lys Arg Tyr Phe Asp Ser Gly Asp Arg Glu Leu
225                 230                 235                 240

Glu Glu Glu Gly Lys Arg Phe Arg Glu Ile Leu Asp Glu Thr Leu Leu
                245                 250                 255

Leu Ala Gly Ala Ser Asn Val Gly Asp Tyr Leu Pro Ile Leu Asn Trp
            260                 265                 270

Leu Gly Val Lys Ser Leu Glu Lys Lys Leu Ile Ala Leu Gln Lys Lys
            275                 280                 285

Arg Asp Asp Phe Phe Gln Gly Leu Ile Glu Gln Val Arg Lys Ser Arg
290                 295                 300

Gly Ala Lys Val Gly Lys Gly Arg Lys Thr Met Ile Glu Leu Leu Leu
305                 310                 315                 320

Ser Leu Gln Glu Ser Glu Pro Glu Tyr Tyr Thr Asp Ala Met Ile Arg
                325                 330                 335
```

```
Ser Phe Val Leu Gly Leu Leu Ala Ala Gly Ser Asp Thr Ser Ala Gly
                340                 345                 350

Thr Met Glu Trp Ala Met Ser Leu Leu Val Asn His Pro His Val Leu
            355                 360                 365

Lys Lys Ala Gln Ala Glu Ile Asp Arg Val Ile Gly Asn Asn Arg Leu
        370                 375                 380

Ile Asp Glu Ser Asp Ile Gly Asn Ile Pro Tyr Ile Gly Cys Ile Ile
385                 390                 395                 400

Asn Glu Thr Leu Arg Leu Tyr Pro Ala Gly Pro Leu Leu Phe Pro His
                405                 410                 415

Glu Ser Ser Ala Asp Cys Val Ile Ser Gly Tyr Asn Ile Pro Arg Gly
            420                 425                 430

Thr Met Leu Ile Val Asn Gln Trp Ala Ile His His Asp Pro Lys Val
        435                 440                 445

Trp Asp Asp Pro Glu Thr Phe Lys Pro Glu Arg Phe Gln Gly Leu Glu
    450                 455                 460

Gly Thr Arg Asp Gly Phe Lys Leu Met Pro Phe Gly Ser Gly Arg Arg
465                 470                 475                 480

Gly Cys Pro Gly Glu Gly Leu Ala Ile Arg Leu Leu Gly Met Thr Leu
                485                 490                 495

Gly Ser Val Ile Gln Cys Phe Asp Trp Glu Arg Val Gly Asp Glu Met
            500                 505                 510

Val Asp Met Thr Glu Gly Leu Gly Val Thr Leu Pro Lys Ala Val Pro
        515                 520                 525

Leu Val Ala Lys Cys Lys Pro Arg Ser Glu Met Thr Asn Leu Leu Ser
530                 535                 540

Glu Leu
545

<210> SEQ ID NO 4

<400> SEQUENCE: 4

000

<210> SEQ ID NO 5
<211> LENGTH: 519
<212> TYPE: PRT
<213> ORGANISM: Artificial Sequence
<220> FEATURE:
<223> OTHER INFORMATION: Synthetic: Sr.KO(1a:23a):Sr.KAH(5a:500a)

<400> SEQUENCE: 5

Met Asp Ala Val Thr Gly Leu Leu Thr Val Pro Ala Thr Ala Ile Thr
1               5                   10                  15

Ile Gly Gly Thr Ala Val Ala Tyr Leu Tyr Ile Ser Ile Leu Leu Leu
            20                  25                  30

Leu Ala Ser Tyr Leu Phe Thr Thr Gln Leu Arg Arg Lys Ser Ala Asn
        35                  40                  45

Leu Pro Pro Thr Val Phe Pro Ser Ile Pro Ile Ile Gly His Leu Tyr
    50                  55                  60

Leu Leu Lys Lys Pro Leu Tyr Arg Thr Leu Ala Lys Ile Ala Ala Lys
65                  70                  75                  80

Tyr Gly Pro Ile Leu Gln Leu Gln Leu Gly Tyr Arg Arg Val Leu Val
                85                  90                  95

Ile Ser Ser Pro Ser Ala Ala Glu Glu Cys Phe Thr Asn Asn Asp Val
            100                 105                 110
```

```
Ile Phe Ala Asn Arg Pro Lys Thr Leu Phe Gly Lys Ile Val Gly Gly
            115                 120                 125

Thr Ser Leu Gly Ser Leu Ser Tyr Gly Asp Gln Trp Arg Asn Leu Arg
        130                 135                 140

Arg Val Ala Ser Ile Glu Ile Leu Ser Val His Arg Leu Asn Glu Phe
145                 150                 155                 160

His Asp Ile Arg Val Asp Glu Asn Arg Leu Leu Ile Arg Lys Leu Arg
                165                 170                 175

Ser Ser Ser Ser Pro Val Thr Leu Ile Thr Val Phe Tyr Ala Leu Thr
            180                 185                 190

Leu Asn Val Ile Met Arg Met Ile Ser Gly Lys Arg Tyr Phe Asp Ser
        195                 200                 205

Gly Asp Arg Glu Leu Glu Glu Glu Gly Lys Arg Phe Arg Glu Ile Leu
        210                 215                 220

Asp Glu Thr Leu Leu Leu Ala Gly Ala Ser Asn Val Gly Asp Tyr Leu
225                 230                 235                 240

Pro Ile Leu Asn Trp Leu Gly Val Lys Ser Leu Glu Lys Lys Leu Ile
                245                 250                 255

Ala Leu Gln Lys Lys Arg Asp Asp Phe Phe Gln Gly Leu Ile Glu Gln
            260                 265                 270

Val Arg Lys Ser Arg Gly Ala Lys Val Gly Lys Gly Arg Lys Thr Met
        275                 280                 285

Ile Glu Leu Leu Leu Ser Leu Gln Glu Ser Glu Pro Glu Tyr Tyr Thr
        290                 295                 300

Asp Ala Met Ile Arg Ser Phe Val Leu Gly Leu Leu Ala Ala Gly Ser
305                 310                 315                 320

Asp Thr Ser Ala Gly Thr Met Glu Trp Ala Met Ser Leu Leu Val Asn
                325                 330                 335

His Pro His Val Leu Lys Lys Ala Gln Ala Glu Ile Asp Arg Val Ile
            340                 345                 350

Gly Asn Asn Arg Leu Ile Asp Glu Ser Asp Ile Gly Asn Ile Pro Tyr
        355                 360                 365

Ile Gly Cys Ile Ile Asn Glu Thr Leu Arg Leu Tyr Pro Ala Gly Pro
        370                 375                 380

Leu Leu Phe Pro His Glu Ser Ser Ala Asp Cys Val Ile Ser Gly Tyr
385                 390                 395                 400

Asn Ile Pro Arg Gly Thr Met Leu Ile Val Asn Gln Trp Ala Ile His
                405                 410                 415

His Asp Pro Lys Val Trp Asp Asp Pro Glu Thr Phe Lys Pro Glu Arg
            420                 425                 430

Phe Gln Gly Leu Glu Gly Thr Arg Asp Gly Phe Lys Leu Met Pro Phe
        435                 440                 445

Gly Ser Gly Arg Arg Gly Cys Pro Gly Glu Gly Leu Ala Ile Arg Leu
450                 455                 460

Leu Gly Met Thr Leu Gly Ser Val Ile Gln Cys Phe Asp Trp Glu Arg
465                 470                 475                 480

Val Gly Asp Glu Met Val Asp Met Thr Glu Gly Leu Gly Val Thr Leu
                485                 490                 495

Pro Lys Ala Val Pro Leu Val Ala Lys Cys Lys Pro Arg Ser Glu Met
            500                 505                 510

Thr Asn Leu Leu Ser Glu Leu
        515
```

```
<210> SEQ ID NO 6
<211> LENGTH: 513
<212> TYPE: PRT
<213> ORGANISM: Artificial Sequence
<220> FEATURE:
<223> OTHER INFORMATION: Synthetic: Sr.KO

<400> SEQUENCE: 6

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365
```

```
Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
                435                 440                 445

Thr Met Ala Phe Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
                500                 505                 510

Ile

<210> SEQ ID NO 7
<211> LENGTH: 320
<212> TYPE: PRT
<213> ORGANISM: Artificial Sequence
<220> FEATURE:
<223> OTHER INFORMATION: Synthetic: Bt.GGPPS

<400> SEQUENCE: 7

Met Leu Thr Ser Ser Lys Ser Ile Glu Ser Phe Pro Lys Asn Val Gln
1               5                   10                  15

Pro Tyr Gly Lys His Tyr Gln Asn Gly Leu Glu Pro Val Gly Lys Ser
            20                  25                  30

Gln Glu Asp Ile Leu Leu Glu Pro Phe His Tyr Leu Cys Ser Asn Pro
        35                  40                  45

Gly Lys Asp Val Arg Thr Lys Met Ile Glu Ala Phe Asn Ala Trp Leu
    50                  55                  60

Lys Val Pro Lys Asp Asp Leu Ile Val Ile Thr Arg Val Ile Glu Met
65                  70                  75                  80

Leu His Ser Ala Ser Leu Leu Ile Asp Asp Val Glu Asp Ser Val
                85                  90                  95

Leu Arg Arg Gly Val Pro Ala Ala His His Ile Tyr Gly Thr Pro Gln
                100                 105                 110

Thr Ile Asn Cys Ala Asn Tyr Val Tyr Phe Leu Ala Leu Lys Glu Ile
            115                 120                 125

Ala Lys Leu Asn Lys Pro Asn Met Ile Thr Ile Tyr Thr Asp Glu Leu
    130                 135                 140

Ile Asn Leu His Arg Gly Gln Gly Met Glu Leu Phe Trp Arg Asp Thr
145                 150                 155                 160

Leu Thr Cys Pro Thr Glu Lys Glu Phe Leu Asp Met Val Asn Asp Lys
                165                 170                 175

Thr Gly Gly Leu Leu Arg Leu Ala Val Lys Leu Met Gln Glu Ala Ser
            180                 185                 190

Gln Ser Gly Thr Asp Tyr Thr Gly Leu Val Ser Lys Ile Gly Ile His
        195                 200                 205
```

```
Phe Gln Val Arg Asp Asp Tyr Met Asn Leu Gln Ser Lys Asn Tyr Ala
    210                 215                 220

Asp Asn Lys Gly Phe Cys Glu Asp Leu Thr Glu Gly Lys Phe Ser Phe
225                 230                 235                 240

Pro Ile Ile His Ser Ile Arg Ser Asp Pro Ser Asn Arg Gln Leu Leu
                245                 250                 255

Asn Ile Leu Lys Gln Arg Ser Ser Ile Glu Leu Lys Gln Phe Ala
                260                 265                 270

Leu Gln Leu Leu Glu Asn Thr Asn Thr Phe Gln Tyr Cys Arg Asp Phe
        275                 280                 285

Leu Arg Val Leu Glu Lys Glu Ala Arg Glu Glu Ile Lys Leu Leu Gly
    290                 295                 300

Gly Asn Ile Met Leu Glu Lys Ile Met Asp Val Leu Ser Val Asn Glu
305                 310                 315                 320

<210> SEQ ID NO 8
<211> LENGTH: 736
<212> TYPE: PRT
<213> ORGANISM: Artificial Sequence
<220> FEATURE:
<223> OTHER INFORMATION: Synthetic: Ent-Os.CDPS

<400> SEQUENCE: 8

Met Glu His Ala Arg Pro Pro Gln Gly Gly Asp Asp Val Ala Ala
1               5                   10                  15

Ser Thr Ser Glu Leu Pro Tyr Met Ile Glu Ser Ile Lys Ser Lys Leu
                20                  25                  30

Arg Ala Ala Arg Asn Ser Leu Gly Glu Thr Thr Val Ser Ala Tyr Asp
            35                  40                  45

Thr Ala Trp Ile Ala Leu Val Asn Arg Leu Asp Gly Gly Gly Glu Arg
    50                  55                  60

Ser Pro Gln Phe Pro Glu Ala Ile Asp Trp Ile Ala Arg Asn Gln Leu
65                  70                  75                  80

Pro Asp Gly Ser Trp Gly Asp Ala Gly Met Phe Ile Val Gln Asp Arg
                85                  90                  95

Leu Ile Asn Thr Leu Gly Cys Val Val Ala Leu Ala Thr Trp Gly Val
                100                 105                 110

His Glu Glu Gln Arg Ala Arg Gly Leu Ala Tyr Ile Gln Asp Asn Leu
            115                 120                 125

Trp Arg Leu Gly Glu Asp Asp Glu Glu Trp Met Met Val Gly Phe Glu
    130                 135                 140

Ile Thr Phe Pro Val Leu Leu Glu Lys Ala Lys Asn Leu Gly Leu Asp
145                 150                 155                 160

Ile Asn Tyr Asp Asp Pro Ala Leu Gln Asp Ile Tyr Ala Lys Arg Gln
                165                 170                 175

Leu Lys Leu Ala Lys Ile Pro Arg Glu Ala Leu His Ala Arg Pro Thr
            180                 185                 190

Thr Leu Leu His Ser Leu Glu Gly Met Glu Asn Leu Asp Trp Glu Arg
    195                 200                 205

Leu Leu Gln Phe Lys Cys Pro Ala Gly Ser Leu His Ser Ser Pro Ala
    210                 215                 220

Ala Ser Ala Tyr Ala Leu Ser Glu Thr Gly Asp Lys Glu Leu Leu Glu
225                 230                 235                 240

Tyr Leu Glu Thr Ala Ile Asn Asn Phe Asp Gly Gly Ala Pro Cys Thr
                245                 250                 255
```

```
Tyr Pro Val Asp Asn Phe Asp Arg Leu Trp Ser Val Asp Arg Leu Arg
        260                 265                 270

Arg Leu Gly Ile Ser Arg Tyr Phe Thr Ser Glu Ile Glu Glu Tyr Leu
        275                 280                 285

Glu Tyr Ala Tyr Arg His Leu Ser Pro Asp Gly Met Ser Tyr Gly Gly
        290                 295                 300

Leu Cys Pro Val Lys Asp Ile Asp Asp Thr Ala Met Ala Phe Arg Leu
305                 310                 315                 320

Leu Arg Leu His Gly Tyr Asn Val Ser Ser Val Phe Asn His Phe
                325                 330                 335

Glu Lys Asp Gly Glu Tyr Phe Cys Phe Ala Gly Gln Ser Ser Gln Ser
        340                 345                 350

Leu Thr Ala Met Tyr Asn Ser Tyr Arg Ala Ser Gln Ile Val Phe Pro
        355                 360                 365

Gly Asp Asp Asp Gly Leu Glu Gln Leu Arg Ala Tyr Cys Arg Ala Phe
        370                 375                 380

Leu Glu Glu Arg Arg Ala Thr Gly Asn Leu Arg Asp Lys Trp Val Ile
385                 390                 395                 400

Ala Asn Gly Leu Pro Ser Glu Val Glu Tyr Ala Leu Asp Phe Pro Trp
                405                 410                 415

Lys Ala Ser Leu Pro Arg Val Glu Thr Arg Val Tyr Leu Glu Gln Tyr
                420                 425                 430

Gly Ala Ser Glu Asp Ala Trp Ile Gly Lys Gly Leu Tyr Arg Met Thr
            435                 440                 445

Leu Val Asn Asn Asp Leu Tyr Leu Glu Ala Ala Lys Ala Asp Phe Thr
450                 455                 460

Asn Phe Gln Arg Leu Ser Arg Leu Glu Trp Leu Ser Leu Lys Arg Trp
465                 470                 475                 480

Tyr Ile Arg Asn Asn Leu Gln Ala His Gly Val Thr Glu Gln Ser Val
                485                 490                 495

Leu Arg Ala Tyr Phe Leu Ala Ala Asn Ile Phe Glu Pro Asn Arg
                500                 505                 510

Ala Ala Glu Arg Leu Gly Trp Ala Arg Thr Ala Ile Leu Ala Glu Ala
        515                 520                 525

Ile Ala Ser His Leu Arg Gln Tyr Ser Ala Asn Gly Ala Ala Asp Gly
        530                 535                 540

Met Thr Glu Arg Leu Ile Ser Gly Leu Ala Ser His Asp Trp Asp Trp
545                 550                 555                 560

Arg Glu Ser Asn Asp Ser Ala Ala Arg Ser Leu Leu Tyr Ala Leu Asp
                565                 570                 575

Glu Leu Ile Asp Leu His Ala Phe Gly Asn Ala Ser Asp Ser Leu Arg
                580                 585                 590

Glu Ala Trp Lys Gln Trp Leu Met Ser Trp Thr Asn Glu Ser Gln Gly
        595                 600                 605

Ser Thr Gly Gly Asp Thr Ala Leu Leu Leu Val Arg Thr Ile Glu Ile
        610                 615                 620

Cys Ser Gly Arg His Gly Ser Ala Glu Gln Ser Leu Lys Asn Ser Glu
625                 630                 635                 640

Asp Tyr Ala Arg Leu Glu Gln Ile Ala Ser Met Cys Ser Lys Leu
                645                 650                 655

Ala Thr Lys Ile Leu Ala Gln Asn Gly Gly Ser Met Asp Asn Val Glu
        660                 665                 670
```

```
Gly Ile Asp Gln Glu Val Asp Val Glu Met Lys Glu Leu Ile Gln Arg
            675                 680                 685

Val Tyr Gly Ser Ser Ser Asn Asp Val Ser Ser Val Thr Arg Gln Thr
        690                 695                 700

Phe Leu Asp Val Val Lys Ser Phe Cys Tyr Val Ala His Cys Ser Pro
705                 710                 715                 720

Glu Thr Ile Asp Gly His Ile Ser Lys Val Leu Phe Glu Asp Val Asn
                725                 730                 735

<210> SEQ ID NO 9
<211> LENGTH: 757
<212> TYPE: PRT
<213> ORGANISM: Artificial Sequence
<220> FEATURE:
<223> OTHER INFORMATION: Synthetic: Ent-Pg.KS

<400> SEQUENCE: 9

Met Lys Arg Glu Gln Tyr Thr Ile Leu Asn Glu Lys Glu Ser Met Ala
1               5                   10                  15

Glu Glu Leu Ile Leu Arg Ile Lys Arg Met Phe Ser Glu Ile Glu Asn
            20                  25                  30

Thr Gln Thr Ser Ala Ser Ala Tyr Asp Thr Ala Trp Val Ala Met Val
        35                  40                  45

Pro Ser Leu Asp Ser Ser Gln Gln Pro Gln Phe Pro Gln Cys Leu Ser
50                  55                  60

Trp Ile Ile Asp Asn Gln Leu Leu Asp Gly Ser Trp Gly Ile Pro Tyr
65                  70                  75                  80

Leu Ile Ile Lys Asp Arg Leu Cys His Thr Leu Ala Cys Val Ile Ala
                85                  90                  95

Leu Arg Lys Trp Asn Ala Gly Asn Gln Asn Val Glu Thr Gly Leu Arg
            100                 105                 110

Phe Leu Arg Glu Asn Ile Glu Gly Ile Val His Glu Asp Glu Tyr Thr
        115                 120                 125

Pro Ile Gly Phe Gln Ile Ile Phe Pro Ala Met Leu Glu Glu Ala Arg
130                 135                 140

Gly Leu Gly Leu Glu Leu Pro Tyr Asp Leu Thr Pro Ile Lys Leu Met
145                 150                 155                 160

Leu Thr His Arg Glu Lys Ile Met Lys Gly Lys Ala Ile Asp His Met
                165                 170                 175

His Glu Tyr Asp Ser Ser Leu Ile Tyr Thr Val Glu Gly Ile His Lys
            180                 185                 190

Ile Val Asp Trp Asn Lys Val Leu Lys His Gln Asn Lys Asp Gly Ser
        195                 200                 205

Leu Phe Asn Ser Pro Ser Ala Thr Ala Cys Ala Leu Met His Thr Arg
210                 215                 220

Lys Ser Asn Cys Leu Glu Tyr Leu Ser Ser Met Leu Gln Lys Leu Gly
225                 230                 235                 240

Asn Gly Val Pro Ser Val Tyr Pro Ile Asn Leu Tyr Ala Arg Ile Ser
                245                 250                 255

Met Ile Asp Arg Leu Gln Arg Leu Gly Leu Ala Arg His Phe Arg Asn
            260                 265                 270

Glu Ile Ile His Ala Leu Asp Asp Ile Tyr Arg Tyr Trp Met Gln Arg
        275                 280                 285

Glu Thr Ser Arg Glu Gly Lys Ser Leu Thr Pro Asp Ile Val Ser Thr
290                 295                 300
```

-continued

```
Ser Ile Ala Phe Met Leu Leu Arg Leu His Gly Tyr Asp Val Pro Ala
305                 310                 315                 320

Asp Val Phe Cys Cys Tyr Asp Leu His Ser Ile Glu Gln Ser Gly Glu
            325                 330                 335

Ala Val Thr Ala Met Leu Ser Leu Tyr Arg Ala Ser Gln Ile Met Phe
                340                 345                 350

Pro Gly Glu Thr Ile Leu Glu Glu Ile Lys Thr Val Ser Arg Lys Tyr
            355                 360                 365

Leu Asp Lys Arg Lys Glu Asn Gly Gly Ile Tyr Asp His Asn Ile Val
370                 375                 380

Met Lys Asp Leu Arg Gly Glu Val Glu Tyr Ala Leu Ser Val Pro Trp
385                 390                 395                 400

Tyr Ala Ser Leu Glu Arg Ile Glu Asn Arg Arg Tyr Ile Asp Gln Tyr
                405                 410                 415

Gly Val Asn Asp Thr Trp Ile Ala Lys Thr Ser Tyr Lys Ile Pro Cys
            420                 425                 430

Ile Ser Asn Asp Leu Phe Leu Ala Leu Ala Lys Gln Asp Tyr Asn Ile
            435                 440                 445

Cys Gln Ala Ile Gln Gln Lys Glu Leu Arg Glu Leu Glu Arg Trp Phe
450                 455                 460

Ala Asp Asn Lys Phe Ser His Leu Asn Phe Ala Arg Gln Lys Leu Ile
465                 470                 475                 480

Tyr Cys Tyr Phe Ser Ala Ala Thr Leu Phe Ser Pro Glu Leu Ser
                485                 490                 495

Ala Ala Arg Val Val Trp Ala Lys Asn Gly Val Ile Thr Thr Val Val
            500                 505                 510

Asp Asp Phe Phe Asp Val Gly Gly Ser Ser Glu Glu Ile His Ser Phe
            515                 520                 525

Val Glu Ala Val Arg Val Trp Asp Glu Ala Ala Thr Asp Gly Leu Ser
            530                 535                 540

Glu Asn Val Gln Ile Leu Phe Ser Ala Leu Tyr Asn Thr Val Asp Glu
545                 550                 555                 560

Ile Val Gln Gln Ala Phe Val Phe Gln Gly Arg Asp Ile Ser Ile His
                565                 570                 575

Leu Arg Glu Ile Trp Tyr Arg Leu Val Asn Ser Met Met Thr Glu Ala
            580                 585                 590

Gln Trp Ala Arg Thr His Cys Leu Pro Ser Met His Glu Tyr Met Glu
            595                 600                 605

Asn Ala Glu Pro Ser Ile Ala Leu Glu Pro Ile Val Leu Ser Ser Leu
610                 615                 620

Tyr Phe Val Gly Pro Lys Leu Ser Glu Glu Ile Ile Cys His Pro Glu
625                 630                 635                 640

Tyr Tyr Asn Leu Met His Leu Leu Asn Ile Cys Gly Arg Leu Leu Asn
                645                 650                 655

Asp Ile Gln Gly Cys Lys Arg Glu Ala His Gln Gly Lys Leu Asn Ser
            660                 665                 670

Val Thr Leu Tyr Met Glu Glu Asn Ser Gly Thr Thr Met Glu Asp Ala
            675                 680                 685

Ile Val Tyr Leu Arg Lys Thr Ile Asp Glu Ser Arg Gln Leu Leu Leu
            690                 695                 700

Lys Glu Val Leu Arg Pro Ser Ile Val Pro Arg Glu Cys Lys Gln Leu
705                 710                 715                 720
```

```
His Trp Asn Met Met Arg Ile Leu Gln Leu Phe Tyr Leu Lys Asn Asp
                725                 730                 735

Gly Phe Thr Ser Pro Thr Glu Met Leu Gly Tyr Val Asn Ala Val Ile
            740                 745                 750

Val Asp Pro Ile Leu
        755

<210> SEQ ID NO 10
<211> LENGTH: 499
<212> TYPE: PRT
<213> ORGANISM: Artificial Sequence
<220> FEATURE:
<223> OTHER INFORMATION: Synthetic: Ps.KO

<400> SEQUENCE: 10

Met Asp Thr Leu Thr Leu Ser Leu Gly Phe Leu Ser Leu Phe Leu Phe
1               5                   10                  15

Leu Phe Leu Leu Lys Arg Ser Thr His Lys His Ser Lys Leu Ser His
            20                  25                  30

Val Pro Val Val Pro Gly Leu Pro Val Ile Gly Asn Leu Leu Gln Leu
        35                  40                  45

Lys Glu Lys Lys Pro His Lys Thr Phe Thr Lys Met Ala Gln Lys Tyr
50                  55                  60

Gly Pro Ile Phe Ser Ile Lys Ala Gly Ser Ser Lys Ile Ile Val Leu
65                  70                  75                  80

Asn Thr Ala His Leu Ala Lys Glu Ala Met Val Thr Arg Tyr Ser Ser
            85                  90                  95

Ile Ser Lys Arg Lys Leu Ser Thr Ala Leu Thr Ile Leu Thr Ser Asp
            100                 105                 110

Lys Cys Met Val Ala Met Ser Asp Tyr Asn Asp Phe His Lys Met Val
            115                 120                 125

Lys Lys His Ile Leu Ala Ser Val Leu Gly Ala Asn Ala Gln Lys Arg
130                 135                 140

Leu Arg Phe His Arg Glu Val Met Met Glu Asn Met Ser Ser Lys Phe
145                 150                 155                 160

Asn Glu His Val Lys Thr Leu Ser Asp Ser Ala Val Asp Phe Arg Lys
            165                 170                 175

Ile Phe Val Ser Glu Leu Phe Gly Leu Ala Leu Lys Gln Ala Leu Gly
            180                 185                 190

Ser Asp Ile Glu Ser Ile Tyr Val Glu Gly Leu Thr Ala Thr Leu Ser
            195                 200                 205

Arg Glu Asp Leu Tyr Asn Thr Leu Val Val Asp Phe Met Glu Gly Ala
210                 215                 220

Ile Glu Val Asp Trp Arg Asp Phe Phe Pro Tyr Leu Lys Trp Ile Pro
225                 230                 235                 240

Asn Lys Ser Phe Glu Lys Lys Ile Arg Arg Val Asp Arg Gln Arg Lys
            245                 250                 255

Ile Ile Met Lys Ala Leu Ile Asn Glu Gln Lys Lys Arg Leu Thr Ser
            260                 265                 270

Gly Lys Glu Leu Asp Cys Tyr Tyr Asp Tyr Leu Val Ser Glu Ala Lys
            275                 280                 285

Glu Val Thr Glu Glu Gln Met Ile Met Leu Leu Trp Glu Pro Ile Ile
        290                 295                 300

Glu Thr Ser Asp Thr Thr Leu Val Thr Thr Glu Trp Ala Met Tyr Glu
305                 310                 315                 320
```

```
Leu Ala Lys Asp Lys Asn Arg Gln Asp Arg Leu Tyr Glu Glu Leu Leu
                325                 330                 335

Asn Val Cys Gly His Glu Lys Val Thr Asp Glu Glu Leu Ser Lys Leu
            340                 345                 350

Pro Tyr Leu Gly Ala Val Phe His Glu Thr Leu Arg Lys His Ser Pro
        355                 360                 365

Val Pro Ile Val Pro Leu Arg Tyr Val Asp Glu Asp Thr Glu Leu Gly
    370                 375                 380

Gly Tyr His Ile Pro Ala Gly Ser Glu Ile Ala Ile Asn Ile Tyr Gly
385                 390                 395                 400

Cys Asn Met Asp Ser Asn Leu Trp Glu Asn Pro Asp Gln Trp Ile Pro
                405                 410                 415

Glu Arg Phe Leu Asp Glu Lys Tyr Ala Gln Ala Asp Leu Tyr Lys Thr
            420                 425                 430

Met Ala Phe Gly Gly Gly Lys Arg Val Cys Ala Gly Ser Leu Gln Ala
        435                 440                 445

Met Leu Ile Ala Cys Thr Ala Ile Gly Arg Leu Val Gln Glu Phe Glu
    450                 455                 460

Trp Glu Leu Gly His Gly Glu Glu Glu Asn Val Asp Thr Met Gly Leu
465                 470                 475                 480

Thr Thr His Arg Leu His Pro Leu Gln Val Lys Leu Lys Pro Arg Asn
                485                 490                 495

Arg Ile Tyr

<210> SEQ ID NO 11
<211> LENGTH: 711
<212> TYPE: PRT
<213> ORGANISM: Artificial Sequence
<220> FEATURE:
<223> OTHER INFORMATION: Synthetic: At.CPR

<400> SEQUENCE: 11

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
                20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
        50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
                100                 105                 110

Thr Gly Thr Ala Glu Gly Phe Ala Lys Ala Leu Gly Glu Glu Ala Lys
            115                 120                 125

Ala Arg Tyr Glu Lys Thr Arg Phe Lys Ile Val Asp Leu Asp Asp Tyr
        130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175
```

```
Ala Ala Arg Phe Tyr Lys Trp Phe Thr Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Asn Cys Ser Ser Ala
    530                 535                 540

Pro Ile Phe Val Arg Gln Ser Asn Phe Lys Leu Pro Ser Asp Ser Lys
545                 550                 555                 560

Val Pro Ile Ile Met Ile Gly Pro Gly Thr Gly Leu Ala Pro Phe Arg
                565                 570                 575

Gly Phe Leu Gln Glu Arg Leu Ala Leu Val Glu Ser Gly Val Glu Leu
            580                 585                 590
```

```
Gly Pro Ser Val Leu Phe Phe Gly Cys Arg Asn Arg Met Asp Phe
            595                 600                 605

Ile Tyr Glu Glu Leu Gln Arg Phe Val Glu Ser Gly Ala Leu Ala
610                 615                 620

Glu Leu Ser Val Ala Phe Ser Arg Glu Gly Pro Thr Lys Glu Tyr Val
625                 630                 635                 640

Gln His Lys Met Met Asp Lys Ala Ser Asp Ile Trp Asn Met Ile Ser
                645                 650                 655

Gln Gly Ala Tyr Leu Tyr Val Cys Gly Asp Ala Lys Gly Met Ala Arg
                660                 665                 670

Asp Val His Arg Ser Leu His Thr Ile Ala Gln Glu Gln Gly Ser Met
                675                 680                 685

Asp Ser Thr Lys Ala Glu Gly Phe Val Lys Asn Leu Gln Thr Ser Gly
                690                 695                 700

Arg Tyr Leu Arg Asp Val Trp
705                 710

<210> SEQ ID NO 12
<211> LENGTH: 481
<212> TYPE: PRT
<213> ORGANISM: Artificial Sequence
<220> FEATURE:
<223> OTHER INFORMATION: Synthetic: UGT85C2

<400> SEQUENCE: 12

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Ser Gly Pro His Cys Leu Asp Gly
        50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
                100                 105                 110

Pro Pro Thr Cys Ile Ile Ser Asp Gly Phe Leu Ser Val Phe Thr Ile
            115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
210                 215                 220

Ile Phe His Thr Phe Asp Glu Leu Glu Pro Ser Ile Ile Lys Thr Leu
225                 230                 235                 240
```

```
Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Cys Phe Gln Trp Leu
        275                 280                 285

Gln Ser Lys Glu Pro Asn Ser Val Val Tyr Val Asn Phe Gly Ser Thr
290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
450                 455                 460

Ser Leu Asn Ile Asp Lys Met Val Lys Glu Ile Thr Val Leu Ala Arg
465                 470                 475                 480

Asn

<210> SEQ ID NO 13
<211> LENGTH: 460
<212> TYPE: PRT
<213> ORGANISM: Artificial Sequence
<220> FEATURE:
<223> OTHER INFORMATION: Synthetic: UGT74G1

<400> SEQUENCE: 13

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110
```

```
Ala Ile Ile Tyr Asp Ser Met Thr Glu Trp Val Leu Asp Val Ala Ile
            115                 120                 125

Glu Phe Gly Ile Asp Gly Gly Ser Phe Phe Thr Gln Ala Cys Val Val
        130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
                290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
            450                 455                 460

<210> SEQ ID NO 14
<211> LENGTH: 485
<212> TYPE: PRT
<213> ORGANISM: Artificial Sequence
<220> FEATURE:
<223> OTHER INFORMATION: Synthetic: UGT91D_like3

<400> SEQUENCE: 14

Met Tyr Asn Val Thr Tyr His Gln Asn Ser Lys Ala Met Ala Thr Ser
1               5                   10                  15
```

-continued

```
Asp Ser Ile Val Asp Asp Arg Lys Gln Leu His Val Ala Thr Phe Pro
            20              25              30
Trp Leu Ala Phe Gly His Ile Leu Pro Tyr Leu Gln Leu Ser Lys Leu
        35              40              45
Ile Ala Glu Lys Gly His Lys Val Ser Phe Leu Ser Thr Thr Arg Asn
 50              55              60
Ile Gln Arg Leu Ser Ser His Ile Ser Pro Leu Ile Asn Val Val Gln
65              70              75              80
Leu Thr Leu Pro Arg Val Gln Glu Leu Pro Glu Asp Ala Glu Ala Thr
                85              90              95
Thr Asp Val His Pro Glu Asp Ile Pro Tyr Leu Lys Lys Ala Ser Asp
            100             105             110
Gly Leu Gln Pro Glu Val Thr Arg Phe Leu Glu Gln His Ser Pro Asp
        115             120             125
Trp Ile Ile Tyr Asp Tyr Thr His Tyr Trp Leu Pro Ser Ile Ala Ala
130             135             140
Ser Leu Gly Ile Ser Arg Ala His Phe Ser Val Thr Thr Pro Trp Ala
145             150             155             160
Ile Ala Tyr Met Gly Pro Ser Ala Asp Ala Met Ile Asn Gly Ser Asp
                165             170             175
Gly Arg Thr Thr Val Glu Asp Leu Thr Thr Pro Pro Lys Trp Phe Pro
            180             185             190
Phe Pro Thr Lys Val Cys Trp Arg Lys His Asp Leu Ala Arg Leu Val
        195             200             205
Pro Tyr Lys Ala Pro Gly Ile Ser Asp Gly Tyr Arg Met Gly Leu Val
210             215             220
Leu Lys Gly Ser Asp Cys Leu Leu Ser Lys Cys Tyr His Glu Phe Gly
225             230             235             240
Thr Gln Trp Leu Pro Leu Leu Glu Thr Leu His Gln Val Pro Val Val
                245             250             255
Pro Val Gly Leu Leu Pro Pro Glu Ile Pro Gly Asp Glu Lys Asp Glu
            260             265             270
Thr Trp Val Ser Ile Lys Lys Trp Leu Asp Gly Lys Gln Lys Gly Ser
        275             280             285
Val Val Tyr Val Ala Leu Gly Ser Glu Val Leu Val Ser Gln Thr Glu
290             295             300
Val Val Glu Leu Ala Leu Gly Leu Glu Leu Ser Gly Leu Pro Phe Val
305             310             315             320
Trp Ala Tyr Arg Lys Pro Lys Gly Pro Ala Lys Ser Asp Ser Val Glu
                325             330             335
Leu Pro Asp Gly Phe Val Glu Arg Thr Arg Asp Arg Gly Leu Val Trp
            340             345             350
Thr Ser Trp Ala Pro Gln Leu Arg Ile Leu Ser His Glu Ser Val Cys
        355             360             365
Gly Phe Leu Thr His Cys Gly Ser Gly Ser Ile Val Glu Gly Leu Met
370             375             380
Phe Gly His Pro Leu Ile Met Leu Pro Ile Phe Gly Asp Gln Pro Leu
385             390             395             400
Asn Ala Arg Leu Leu Glu Asp Lys Gln Val Gly Ile Glu Ile Pro Arg
                405             410             415
Asn Glu Glu Asp Gly Cys Leu Thr Lys Glu Ser Val Ala Arg Ser Leu
            420             425             430
```

Arg Ser Val Val Glu Lys Glu Gly Glu Ile Tyr Lys Ala Asn Ala
        435                 440                 445

Arg Glu Leu Ser Lys Ile Tyr Asn Asp Thr Lys Val Glu Lys Glu Tyr
450                 455                 460

Val Ser Gln Phe Val Asp Tyr Leu Glu Lys Asn Ala Arg Ala Val Ala
465                 470                 475                 480

Ile Asp His Glu Ser
                485

<210> SEQ ID NO 15
<211> LENGTH: 458
<212> TYPE: PRT
<213> ORGANISM: Artificial Sequence
<220> FEATURE:
<223> OTHER INFORMATION: Synthetic: UGT76G1

<400> SEQUENCE: 15

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

```
Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
    450                 455

<210> SEQ ID NO 16
<211> LENGTH: 436
<212> TYPE: PRT
<213> ORGANISM: Artificial Sequence
<220> FEATURE:
<223> OTHER INFORMATION: Synthetic: UGT40087

<400> SEQUENCE: 16

Met Asp Ala Ser Asp Ser Ser Pro Leu His Ile Val Ile Phe Pro Trp
1               5                   10                  15

Leu Ala Phe Gly His Met Leu Ala Ser Leu Glu Leu Ala Glu Arg Leu
            20                  25                  30

Ala Ala Arg Gly His Arg Val Ser Phe Val Ser Thr Pro Arg Asn Ile
        35                  40                  45

Ser Arg Leu Arg Pro Val Pro Pro Ala Leu Ala Pro Leu Ile Asp Phe
    50                  55                  60

Val Ala Leu Pro Leu Pro Arg Val Asp Gly Leu Pro Asp Gly Ala Glu
65                  70                  75                  80

Ala Thr Ser Asp Ile Pro Pro Gly Lys Thr Glu Leu His Leu Lys Ala
            85                  90                  95

Leu Asp Gly Leu Ala Ala Pro Phe Ala Ala Phe Leu Asp Ala Ala Cys
            100                 105                 110

Ala Asp Gly Ser Thr Asn Lys Val Asp Trp Leu Phe Leu Asp Asn Phe
        115                 120                 125

Gln Tyr Trp Ala Ala Ala Ala Ala Asp His Lys Ile Pro Cys Ala
    130                 135                 140

Leu Asn Leu Thr Phe Ala Ala Ser Thr Ser Ala Glu Tyr Gly Val Pro
145                 150                 155                 160

Arg Val Glu Pro Pro Val Asp Gly Ser Thr Ala Ser Ile Leu Gln Arg
            165                 170                 175

Phe Val Leu Thr Leu Glu Lys Cys Gln Phe Val Ile Gln Arg Ala Cys
            180                 185                 190

Phe Glu Leu Glu Pro Glu Pro Leu Pro Leu Leu Ser Asp Ile Phe Gly
        195                 200                 205
```

```
Lys Pro Val Ile Pro Tyr Gly Leu Val Pro Pro Cys Pro Ala Glu
    210                 215                 220
Gly His Lys Arg Glu His Gly Asn Ala Ala Leu Ser Trp Leu Asp Lys
225                 230                 235                 240
Gln Gln Pro Glu Ser Val Leu Phe Ile Ala Leu Gly Ser Glu Pro Pro
                245                 250                 255
Val Thr Val Glu Gln Leu His Glu Ile Ala Leu Gly Leu Glu Leu Ala
            260                 265                 270
Gly Thr Thr Phe Leu Trp Ala Leu Lys Lys Pro Asn Gly Leu Leu Leu
        275                 280                 285
Glu Ala Asp Gly Asp Ile Leu Pro Pro Gly Phe Glu Glu Arg Thr Arg
    290                 295                 300
Asp Arg Gly Leu Val Ala Met Gly Trp Val Pro Gln Pro Ile Ile Leu
305                 310                 315                 320
Ala His Ser Ser Val Gly Ala Phe Leu Thr His Gly Gly Trp Ala Ser
                325                 330                 335
Thr Ile Glu Gly Val Met Ser Gly His Pro Met Leu Phe Leu Thr Phe
            340                 345                 350
Leu Asp Glu Gln Arg Ile Asn Ala Gln Leu Ile Glu Arg Lys Lys Ala
        355                 360                 365
Gly Leu Arg Val Pro Arg Arg Glu Lys Asp Gly Ser Tyr Asp Arg Gln
    370                 375                 380
Gly Ile Ala Gly Ala Ile Arg Ala Val Met Cys Glu Glu Ser Lys
385                 390                 395                 400
Ser Val Phe Ala Ala Asn Ala Lys Lys Met Gln Glu Ile Val Ser Asp
                405                 410                 415
Arg Asn Cys Gln Glu Lys Tyr Ile Asp Glu Leu Ile Gln Arg Leu Gly
            420                 425                 430
Ser Phe Glu Lys
        435

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21
<211> LENGTH: 544
<212> TYPE: PRT
<213> ORGANISM: Artificial Sequence
```

<220> FEATURE:
<223> OTHER INFORMATION: Synthetic:
    Aa.CPR(1a:66a):Sr.KAH_mutant#10(23a:500a)

<400> SEQUENCE: 21

Met Gln Ser Thr Thr Ser Val Lys Leu Ser Pro Phe Asp Leu Met Thr
1               5                   10                  15

Ala Leu Leu Asn Gly Lys Val Ser Phe Asp Thr Ser Asn Thr Ser Asp
            20                  25                  30

Thr Asn Ile Pro Leu Ala Val Phe Met Glu Asn Arg Glu Leu Leu Met
        35                  40                  45

Ile Leu Thr Thr Ser Val Ala Val Leu Ile Gly Cys Val Val Val Leu
    50                  55                  60

Val Trp Leu Arg Arg Lys Ser Ala Asn Leu Pro Pro Thr Val Phe Pro
65                  70                  75                  80

Ser Ile Pro Ile Ile Gly His Leu Tyr Leu Leu Lys Lys Pro Leu Tyr
                85                  90                  95

Arg Thr Leu Ala Lys Ile Ala Ala Lys Tyr Gly Pro Ile Leu Gln Leu
            100                 105                 110

Gln Leu Gly Tyr Arg Arg Val Leu Val Ile Ser Ser Pro Ser Ala Ala
        115                 120                 125

Glu Glu Cys Phe Thr Asn Asn Asp Val Ile Phe Ala Asn Arg Pro Lys
    130                 135                 140

Thr Leu Phe Gly Lys Ile Val Gly Gly Thr Ser Leu Gly Ser Leu Ser
145                 150                 155                 160

Tyr Gly Asp Gln Trp Arg Asn Leu Arg Arg Val Ala Ser Ile Glu Ile
                165                 170                 175

Leu Ser Val His Arg Leu Asn Glu Phe His Asp Ile Arg Val Asp Glu
            180                 185                 190

Asn Arg Leu Leu Ile Arg Lys Leu Arg Asp Ser Ser Ser Pro Val Thr
        195                 200                 205

Leu Arg Thr Val Phe Tyr Ala Leu Thr Leu Asn Val Ile Met Arg Met
    210                 215                 220

Ile Ser Gly Lys Arg Tyr Phe Asp Ser Gly Asp Arg Glu Leu Glu Glu
225                 230                 235                 240

Glu Gly Lys Arg Phe Arg Glu Ile Leu Asp Glu Thr Leu Leu Leu Ala
                245                 250                 255

Gly Ala Ser Asn Val Gly Asp Tyr Leu Pro Ile Leu Asn Trp Leu Gly
            260                 265                 270

Val Lys Ser Leu Glu Lys Lys Leu Ile Ala Leu Gln Lys Lys Arg Asp
        275                 280                 285

Asp Phe Phe Gln Gly Leu Ile Glu Gln Val Arg Lys Ser Arg Gly Ala
    290                 295                 300

Lys Val Gly Lys Gly Arg Lys Thr Met Ile Glu Leu Leu Ser Leu
305                 310                 315                 320

Gln Glu Ser Glu Pro Glu Tyr Tyr Thr Asp Ala Met Ile Arg Ser Phe
                325                 330                 335

Val Leu Gly Leu Leu Ala Ala Gly Ser Asp Thr Ser Ala Leu Thr Leu
            340                 345                 350

Glu Trp Ala Met Ser Leu Leu Leu Asn His Pro His Val Leu Lys Lys
        355                 360                 365

Ala Gln Ala Glu Ile Asp Arg Val Ile Gly Asn Asn Arg Leu Ile Asp
    370                 375                 380

Glu Ser Asp Ile Gly Asn Ile Pro Tyr Leu Gly Cys Ile Ile Asn Glu
385                 390                 395                 400

Thr Leu Arg Leu Tyr Pro Ala Gly Pro Leu Leu Phe Pro His Glu Ser
            405                 410                 415

Ser Ala Asp Cys Val Ile Ser Gly Tyr Asn Ile Pro Arg Gly Thr Met
            420                 425                 430

Leu Ile Val Asn Gln Trp Ala Ile His His Asp Pro Lys Val Trp Asp
            435                 440                 445

Asp Pro Glu Thr Phe Lys Pro Glu Arg Phe Gln Gly Leu Glu Gly Thr
            450                 455                 460

Arg Asp Gly Phe Lys Leu Met Pro Phe Gly Ser Gly Arg Arg Gly Cys
465                 470                 475                 480

Pro Gly Glu Gly Leu Ala Ile Arg Leu Leu Gly Met Thr Leu Gly Ser
            485                 490                 495

Val Ile Gln Cys Phe Asp Trp Glu Arg Val Gly Asp Glu Met Val Asp
            500                 505                 510

Met Thr Glu Gly Leu Gly Val Thr Leu Pro Lys Ala Val Pro Leu Val
            515                 520                 525

Ala Lys Cys Lys Pro Arg Ser Glu Met Thr Asn Leu Leu Ser Glu Leu
            530                 535                 540

<210> SEQ ID NO 22
<211> LENGTH: 550
<212> TYPE: PRT
<213> ORGANISM: Artificial Sequence
<220> FEATURE:
<223> OTHER INFORMATION: Synthetic:
    ATR2(1a:72a):Sr.KAH_mutant#10(23a:500a)

<400> SEQUENCE: 22

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
                20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
50                  55                  60

Gly Cys Ile Val Met Leu Val Trp Leu Arg Arg Lys Ser Ala Asn Leu
65                  70                  75                  80

Pro Pro Thr Val Phe Pro Ser Ile Pro Ile Ile Gly His Leu Tyr Leu
                85                  90                  95

Leu Lys Lys Pro Leu Tyr Arg Thr Leu Ala Lys Ile Ala Ala Lys Tyr
                100                 105                 110

Gly Pro Ile Leu Gln Leu Gln Leu Gly Tyr Arg Arg Val Leu Val Ile
            115                 120                 125

Ser Ser Pro Ser Ala Ala Glu Glu Cys Phe Thr Asn Asn Asp Val Ile
130                 135                 140

Phe Ala Asn Arg Pro Lys Thr Leu Phe Gly Lys Ile Val Gly Gly Thr
145                 150                 155                 160

Ser Leu Gly Ser Leu Ser Tyr Gly Asp Gln Trp Arg Asn Leu Arg Arg
            165                 170                 175

Val Ala Ser Ile Glu Ile Leu Ser Val His Arg Leu Asn Glu Phe His
            180                 185                 190

```
Asp Ile Arg Val Asp Glu Asn Arg Leu Leu Ile Arg Lys Leu Arg Asp
            195                 200                 205

Ser Ser Ser Pro Val Thr Leu Arg Thr Val Phe Tyr Ala Leu Thr Leu
        210                 215                 220

Asn Val Ile Met Arg Met Ile Ser Gly Lys Arg Tyr Phe Asp Ser Gly
225                 230                 235                 240

Asp Arg Glu Leu Glu Glu Gly Lys Arg Phe Arg Glu Ile Leu Asp
            245                 250                 255

Glu Thr Leu Leu Leu Ala Gly Ala Ser Asn Val Gly Asp Tyr Leu Pro
            260                 265                 270

Ile Leu Asn Trp Leu Gly Val Lys Ser Leu Glu Lys Lys Leu Ile Ala
            275                 280                 285

Leu Gln Lys Lys Arg Asp Asp Phe Phe Gln Gly Leu Ile Glu Gln Val
            290                 295                 300

Arg Lys Ser Arg Gly Ala Lys Val Gly Lys Gly Arg Lys Thr Met Ile
305                 310                 315                 320

Glu Leu Leu Leu Ser Leu Gln Glu Ser Glu Pro Glu Tyr Tyr Thr Asp
                325                 330                 335

Ala Met Ile Arg Ser Phe Val Leu Gly Leu Ala Ala Gly Ser Asp
            340                 345                 350

Thr Ser Ala Leu Thr Leu Glu Trp Ala Met Ser Leu Leu Asn His
            355                 360                 365

Pro His Val Leu Lys Lys Ala Gln Ala Glu Ile Asp Arg Val Ile Gly
            370                 375                 380

Asn Asn Arg Leu Ile Asp Glu Ser Asp Ile Gly Asn Ile Pro Tyr Leu
385                 390                 395                 400

Gly Cys Ile Ile Asn Glu Thr Leu Arg Leu Tyr Pro Ala Gly Pro Leu
                405                 410                 415

Leu Phe Pro His Glu Ser Ser Ala Asp Cys Val Ile Ser Gly Tyr Asn
            420                 425                 430

Ile Pro Arg Gly Thr Met Leu Ile Val Asn Gln Trp Ala Ile His His
            435                 440                 445

Asp Pro Lys Val Trp Asp Pro Glu Thr Phe Lys Pro Glu Arg Phe
            450                 455                 460

Gln Gly Leu Glu Gly Thr Arg Asp Gly Phe Lys Leu Met Pro Phe Gly
465                 470                 475                 480

Ser Gly Arg Arg Gly Cys Pro Gly Glu Gly Leu Ala Ile Arg Leu Leu
            485                 490                 495

Gly Met Thr Leu Gly Ser Val Ile Gln Cys Phe Asp Trp Glu Arg Val
            500                 505                 510

Gly Asp Glu Met Val Asp Met Thr Glu Gly Leu Gly Val Thr Leu Pro
            515                 520                 525

Lys Ala Val Pro Leu Val Ala Lys Cys Lys Pro Arg Ser Glu Met Thr
            530                 535                 540

Asn Leu Leu Ser Glu Leu
545                 550

<210> SEQ ID NO 23

<400> SEQUENCE: 23

000

<210> SEQ ID NO 24
```

<211> LENGTH: 544
<212> TYPE: PRT
<213> ORGANISM: Artificial Sequence
<220> FEATURE:
<223> OTHER INFORMATION: Synthetic:
Aa.CPR(1a:66a):Sr.KAH_mutant#3(23a:500a)

<400> SEQUENCE: 24

```
Met Gln Ser Thr Thr Ser Val Lys Leu Ser Pro Phe Asp Leu Met Thr
1               5                   10                  15

Ala Leu Leu Asn Gly Lys Val Ser Phe Asp Thr Ser Asn Thr Ser Asp
            20                  25                  30

Thr Asn Ile Pro Leu Ala Val Phe Met Glu Asn Arg Glu Leu Leu Met
        35                  40                  45

Ile Leu Thr Thr Ser Val Ala Val Leu Ile Gly Cys Val Val Val Leu
    50                  55                  60

Val Trp Leu Arg Arg Lys Ser Ala Asn Leu Pro Pro Thr Val Phe Pro
65                  70                  75                  80

Ser Ile Pro Ile Ile Gly His Leu Tyr Leu Leu Lys Lys Pro Leu Tyr
                85                  90                  95

Arg Thr Leu Ala Lys Ile Ala Ala Lys Tyr Gly Pro Ile Leu Gln Leu
            100                 105                 110

Gln Leu Gly Tyr Arg Arg Val Leu Val Ile Ser Ser Pro Ser Ala Ala
        115                 120                 125

Glu Glu Cys Phe Thr Asn Asn Asp Val Ile Phe Ala Asn Arg Pro Lys
    130                 135                 140

Thr Leu Phe Gly Lys Ile Val Gly Gly Thr Ser Leu Gly Ser Leu Ser
145                 150                 155                 160

Tyr Gly Asp Gln Trp Arg Asn Leu Arg Arg Val Ala Ser Ile Glu Ile
                165                 170                 175

Leu Ser Val His Arg Leu Asn Glu Phe His Asp Ile Arg Val Asp Glu
            180                 185                 190

Asn Arg Leu Leu Leu Arg Lys Leu Arg Asp Ser Ser Ser Pro Val Thr
        195                 200                 205

Leu Arg Thr Val Phe Tyr Ala Leu Thr Leu Asn Val Ile Met Arg Met
    210                 215                 220

Ile Ser Gly Lys Arg Tyr Phe Asp Ser Gly Asp Arg Glu Leu Glu Glu
225                 230                 235                 240

Glu Gly Lys Arg Phe Arg Glu Ile Leu Asp Glu Thr Leu Leu Leu Ala
                245                 250                 255

Gly Ala Ser Asn Val Gly Asp Tyr Leu Pro Ile Leu Asn Trp Leu Gly
            260                 265                 270

Val Lys Ser Asp Glu Lys Lys Leu Ile Ala Leu Gln Lys Lys Arg Asp
        275                 280                 285

Asp Phe Phe Gln Gly Leu Ile Glu Gln Val Arg Lys Ser Arg Gly Ala
    290                 295                 300

Lys Val Gly Lys Gly Arg Lys Thr Met Ile Glu Leu Leu Leu Ser Leu
305                 310                 315                 320

Gln Glu Ser Glu Pro Glu Tyr Tyr Thr Asp Ala Met Ile Arg Ser Phe
                325                 330                 335

Val Leu Gly Leu Leu Ala Ala Gly Ser Asp Thr Ser Ala Gly Thr Met
            340                 345                 350

Glu Trp Ala Met Ser Leu Leu Val Asn His Pro His Val Leu Lys Lys
        355                 360                 365
```

```
Ala Gln Ala Glu Ile Asp Arg Val Gly Asn Asn Arg Leu Ile Asp
        370                 375                 380

Glu Ser Asp Ile Gly Asn Ile Pro Tyr Leu Gly Cys Ile Ile Asn Glu
385                 390                 395                 400

Thr Leu Arg Leu Tyr Pro Ala Gly Pro Leu Leu Phe Pro His Glu Ser
                405                 410                 415

Ser Ala Asp Cys Val Ile Ser Gly Tyr Asn Ile Pro Arg Gly Thr Met
            420                 425                 430

Leu Ile Val Asn Gln Trp Ala Ile His His Asp Pro Lys Val Trp Asp
        435                 440                 445

Asp Pro Glu Thr Phe Lys Pro Glu Arg Phe Gln Gly Leu Glu Gly Thr
    450                 455                 460

Arg Asp Gly Phe Lys Leu Met Pro Phe Gly Ser Gly Arg Arg Gly Cys
465                 470                 475                 480

Pro Gly Glu Gly Leu Ala Ile Arg Leu Leu Gly Met Thr Leu Gly Ser
                485                 490                 495

Val Ile Gln Cys Phe Asp Trp Glu Arg Val Gly Asp Glu Met Val Asp
            500                 505                 510

Met Thr Glu Gly Leu Gly Val Thr Leu Pro Lys Ala Val Pro Leu Val
        515                 520                 525

Ala Lys Cys Lys Pro Arg Ser Glu Met Thr Asn Leu Leu Ser Glu Leu
    530                 535                 540

<210> SEQ ID NO 25
<211> LENGTH: 550
<212> TYPE: PRT
<213> ORGANISM: Artificial Sequence
<220> FEATURE:
<223> OTHER INFORMATION: Synthetic:
      ATR2(1a:72a):Sr.KAH_mutant#3(23a:500a)

<400> SEQUENCE: 25

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Leu Arg Arg Lys Ser Ala Asn Leu
65                  70                  75                  80

Pro Pro Thr Val Phe Pro Ser Ile Pro Ile Ile Gly His Leu Tyr Leu
                85                  90                  95

Leu Lys Lys Pro Leu Tyr Arg Thr Leu Ala Lys Ile Ala Ala Lys Tyr
                100                 105                 110

Gly Pro Ile Leu Gln Leu Gln Leu Gly Tyr Arg Arg Val Leu Val Ile
            115                 120                 125

Ser Ser Pro Ser Ala Ala Glu Glu Cys Phe Thr Asn Asn Asp Val Ile
        130                 135                 140

Phe Ala Asn Arg Pro Lys Thr Leu Phe Gly Lys Ile Val Gly Gly Thr
145                 150                 155                 160

Ser Leu Gly Ser Leu Ser Tyr Gly Asp Gln Trp Arg Asn Leu Arg Arg
                165                 170                 175
```

Val Ala Ser Ile Glu Ile Leu Ser Val His Arg Leu Asn Glu Phe His
            180                 185                 190

Asp Ile Arg Val Asp Glu Asn Arg Leu Leu Arg Lys Leu Arg Asp
        195                 200                 205

Ser Ser Ser Pro Val Thr Leu Arg Thr Val Phe Tyr Ala Leu Thr Leu
210                 215                 220

Asn Val Ile Met Arg Met Ile Ser Gly Lys Arg Tyr Phe Asp Ser Gly
225                 230                 235                 240

Asp Arg Glu Leu Glu Glu Gly Lys Arg Phe Arg Glu Ile Leu Asp
            245                 250                 255

Glu Thr Leu Leu Leu Ala Gly Ala Ser Asn Val Gly Asp Tyr Leu Pro
            260                 265                 270

Ile Leu Asn Trp Leu Gly Val Lys Ser Asp Glu Lys Lys Leu Ile Ala
            275                 280                 285

Leu Gln Lys Lys Arg Asp Asp Phe Phe Gln Gly Leu Ile Glu Gln Val
            290                 295                 300

Arg Lys Ser Arg Gly Ala Lys Val Gly Lys Gly Arg Lys Thr Met Ile
305                 310                 315                 320

Glu Leu Leu Leu Ser Leu Gln Glu Ser Glu Pro Glu Tyr Tyr Thr Asp
                325                 330                 335

Ala Met Ile Arg Ser Phe Val Leu Gly Leu Leu Ala Ala Gly Ser Asp
            340                 345                 350

Thr Ser Ala Gly Thr Met Glu Trp Ala Met Ser Leu Leu Val Asn His
            355                 360                 365

Pro His Val Leu Lys Lys Ala Gln Ala Glu Ile Asp Arg Val Val Gly
            370                 375                 380

Asn Asn Arg Leu Ile Asp Glu Ser Asp Ile Gly Asn Ile Pro Tyr Leu
385                 390                 395                 400

Gly Cys Ile Ile Asn Glu Thr Leu Arg Leu Tyr Pro Ala Gly Pro Leu
                405                 410                 415

Leu Phe Pro His Glu Ser Ser Ala Asp Cys Val Ile Ser Gly Tyr Asn
            420                 425                 430

Ile Pro Arg Gly Thr Met Leu Ile Val Asn Gln Trp Ala Ile His His
            435                 440                 445

Asp Pro Lys Val Trp Asp Asp Pro Glu Thr Phe Lys Pro Glu Arg Phe
        450                 455                 460

Gln Gly Leu Glu Gly Thr Arg Asp Gly Phe Lys Leu Met Pro Phe Gly
465                 470                 475                 480

Ser Gly Arg Arg Gly Cys Pro Gly Glu Gly Leu Ala Ile Arg Leu Leu
                485                 490                 495

Gly Met Thr Leu Gly Ser Val Ile Gln Cys Phe Asp Trp Glu Arg Val
            500                 505                 510

Gly Asp Glu Met Val Asp Met Thr Glu Gly Leu Gly Val Thr Leu Pro
            515                 520                 525

Lys Ala Val Pro Leu Val Ala Lys Cys Lys Pro Arg Ser Glu Met Thr
            530                 535                 540

Asn Leu Leu Ser Glu Leu
545                 550

<210> SEQ ID NO 26
<211> LENGTH: 523
<212> TYPE: PRT
<213> ORGANISM: Artificial Sequence
<220> FEATURE:

<223> OTHER INFORMATION: Synthetic:
ALG11(1a:45a):Sr.KAH_mutant#10(23a:500a)

<400> SEQUENCE: 26

```
Met Gly Ser Ala Trp Thr Asn Tyr Asn Phe Glu Val Lys Ser His
1               5                   10                  15

Phe Gly Phe Lys Lys Tyr Val Val Ser Ser Leu Val Leu Val Tyr Gly
                20                  25                  30

Leu Ile Lys Val Leu Thr Trp Ile Phe Arg Gln Trp Val Leu Arg Arg
            35                  40                  45

Lys Ser Ala Asn Leu Pro Pro Thr Val Phe Pro Ser Ile Pro Ile Ile
        50                  55                  60

Gly His Leu Tyr Leu Leu Lys Lys Pro Leu Tyr Arg Thr Leu Ala Lys
65                  70                  75                  80

Ile Ala Ala Lys Tyr Gly Pro Ile Leu Gln Leu Gln Leu Gly Tyr Arg
                85                  90                  95

Arg Val Leu Val Ile Ser Ser Pro Ser Ala Ala Glu Glu Cys Phe Thr
            100                 105                 110

Asn Asn Asp Val Ile Phe Ala Asn Arg Pro Lys Thr Leu Phe Gly Lys
        115                 120                 125

Ile Val Gly Gly Thr Ser Leu Gly Ser Leu Ser Tyr Gly Asp Gln Trp
130                 135                 140

Arg Asn Leu Arg Arg Val Ala Ser Ile Glu Ile Leu Ser Val His Arg
145                 150                 155                 160

Leu Asn Glu Phe His Asp Ile Arg Val Asp Glu Asn Arg Leu Leu Ile
                165                 170                 175

Arg Lys Leu Arg Asp Ser Ser Ser Pro Val Thr Leu Arg Thr Val Phe
            180                 185                 190

Tyr Ala Leu Thr Leu Asn Val Ile Met Arg Met Ile Ser Gly Lys Arg
        195                 200                 205

Tyr Phe Asp Ser Gly Asp Arg Glu Leu Glu Glu Gly Lys Arg Phe
210                 215                 220

Arg Glu Ile Leu Asp Glu Thr Leu Leu Leu Ala Gly Ala Ser Asn Val
225                 230                 235                 240

Gly Asp Tyr Leu Pro Ile Leu Asn Trp Leu Gly Val Lys Ser Leu Glu
                245                 250                 255

Lys Lys Leu Ile Ala Leu Gln Lys Lys Arg Asp Asp Phe Phe Gln Gly
            260                 265                 270

Leu Ile Glu Gln Val Arg Lys Ser Arg Gly Ala Lys Val Gly Lys Gly
        275                 280                 285

Arg Lys Thr Met Ile Glu Leu Leu Leu Ser Leu Gln Glu Ser Glu Pro
290                 295                 300

Glu Tyr Tyr Thr Asp Ala Met Ile Arg Ser Phe Val Leu Gly Leu Leu
305                 310                 315                 320

Ala Ala Gly Ser Asp Thr Ser Ala Leu Thr Leu Glu Trp Ala Met Ser
                325                 330                 335

Leu Leu Leu Asn His Pro His Val Leu Lys Lys Ala Gln Ala Glu Ile
            340                 345                 350

Asp Arg Val Ile Gly Asn Asn Arg Leu Ile Asp Glu Ser Asp Ile Gly
        355                 360                 365

Asn Ile Pro Tyr Leu Gly Cys Ile Ile Asn Glu Thr Leu Arg Leu Tyr
370                 375                 380

Pro Ala Gly Pro Leu Leu Phe Pro His Glu Ser Ser Ala Asp Cys Val
385                 390                 395                 400
```

```
Ile Ser Gly Tyr Asn Ile Pro Arg Gly Thr Met Leu Ile Val Asn Gln
                405                 410                 415

Trp Ala Ile His His Asp Pro Lys Val Trp Asp Pro Glu Thr Phe
            420                 425                 430

Lys Pro Glu Arg Phe Gln Gly Leu Gly Thr Arg Asp Gly Phe Lys
            435                 440                 445

Leu Met Pro Phe Gly Ser Gly Arg Arg Gly Cys Pro Gly Glu Gly Leu
450                 455                 460

Ala Ile Arg Leu Leu Gly Met Thr Leu Gly Ser Val Ile Gln Cys Phe
465                 470                 475                 480

Asp Trp Glu Arg Val Gly Asp Glu Met Val Asp Met Thr Glu Gly Leu
                485                 490                 495

Gly Val Thr Leu Pro Lys Ala Val Pro Leu Val Ala Lys Cys Lys Pro
                500                 505                 510

Arg Ser Glu Met Thr Asn Leu Leu Ser Glu Leu
            515                 520

<210> SEQ ID NO 27
<211> LENGTH: 529
<212> TYPE: PRT
<213> ORGANISM: Artificial Sequence
<220> FEATURE:
<223> OTHER INFORMATION: Synthetic:
      ERG11(1a:51a):Sr.KAH_mutant#10(23a:500a)

<400> SEQUENCE: 27

Met Ser Ala Thr Lys Ser Ile Val Gly Glu Ala Leu Glu Tyr Val Asn
1               5                   10                  15

Ile Gly Leu Ser His Phe Leu Ala Leu Pro Leu Ala Gln Arg Ile Ser
                20                  25                  30

Leu Ile Ile Ile Ile Pro Phe Ile Tyr Asn Ile Val Trp Gln Leu Leu
            35                  40                  45

Tyr Ser Leu Leu Arg Arg Lys Ser Ala Asn Leu Pro Pro Thr Val Phe
    50                  55                  60

Pro Ser Ile Pro Ile Ile Gly His Leu Tyr Leu Leu Lys Lys Pro Leu
65                  70                  75                  80

Tyr Arg Thr Leu Ala Lys Ile Ala Ala Lys Tyr Gly Pro Ile Leu Gln
                85                  90                  95

Leu Gln Leu Gly Tyr Arg Arg Val Leu Val Ile Ser Ser Pro Ser Ala
            100                 105                 110

Ala Glu Glu Cys Phe Thr Asn Asn Asp Val Ile Phe Ala Asn Arg Pro
        115                 120                 125

Lys Thr Leu Phe Gly Lys Ile Val Gly Gly Thr Ser Leu Gly Ser Leu
    130                 135                 140

Ser Tyr Gly Asp Gln Trp Arg Asn Leu Arg Arg Val Ala Ser Ile Glu
145                 150                 155                 160

Ile Leu Ser Val His Arg Leu Asn Glu Phe His Asp Ile Arg Val Asp
                165                 170                 175

Glu Asn Arg Leu Leu Ile Arg Lys Leu Arg Asp Ser Ser Pro Val
            180                 185                 190

Thr Leu Arg Thr Val Phe Tyr Ala Leu Thr Leu Asn Val Ile Met Arg
        195                 200                 205

Met Ile Ser Gly Lys Arg Tyr Phe Asp Ser Gly Asp Arg Glu Leu Glu
    210                 215                 220
```

Glu Gly Lys Arg Phe Arg Glu Ile Leu Asp Thr Leu Leu Leu
225                 230                 235                 240

Ala Gly Ala Ser Asn Val Gly Asp Tyr Leu Pro Ile Leu Asn Trp Leu
            245                 250                 255

Gly Val Lys Ser Leu Glu Lys Lys Leu Ile Ala Leu Gln Lys Lys Arg
        260                 265                 270

Asp Asp Phe Phe Gln Gly Leu Ile Glu Gln Val Arg Lys Ser Arg Gly
    275                 280                 285

Ala Lys Val Gly Lys Gly Arg Lys Thr Met Ile Glu Leu Leu Leu Ser
290                 295                 300

Leu Gln Glu Ser Glu Pro Glu Tyr Tyr Thr Asp Ala Met Ile Arg Ser
305                 310                 315                 320

Phe Val Leu Gly Leu Leu Ala Ala Gly Ser Asp Thr Ser Ala Leu Thr
                325                 330                 335

Leu Glu Trp Ala Met Ser Leu Leu Asn His Pro His Val Leu Lys
                340                 345                 350

Lys Ala Gln Ala Glu Ile Asp Arg Val Ile Gly Asn Asn Arg Leu Ile
            355                 360                 365

Asp Glu Ser Asp Ile Gly Asn Ile Pro Tyr Leu Gly Cys Ile Ile Asn
370                 375                 380

Glu Thr Leu Arg Leu Tyr Pro Ala Gly Pro Leu Leu Phe Pro His Glu
385                 390                 395                 400

Ser Ser Ala Asp Cys Val Ile Ser Gly Tyr Asn Ile Pro Arg Gly Thr
                405                 410                 415

Met Leu Ile Val Asn Gln Trp Ala Ile His His Asp Pro Lys Val Trp
            420                 425                 430

Asp Asp Pro Glu Thr Phe Lys Pro Glu Arg Phe Gln Gly Leu Glu Gly
        435                 440                 445

Thr Arg Asp Gly Phe Lys Leu Met Pro Phe Gly Ser Gly Arg Arg Gly
    450                 455                 460

Cys Pro Gly Glu Gly Leu Ala Ile Arg Leu Leu Gly Met Thr Leu Gly
465                 470                 475                 480

Ser Val Ile Gln Cys Phe Asp Trp Glu Arg Val Gly Asp Glu Met Val
                485                 490                 495

Asp Met Thr Glu Gly Leu Gly Val Thr Leu Pro Lys Ala Val Pro Leu
            500                 505                 510

Val Ala Lys Cys Lys Pro Arg Ser Glu Met Thr Asn Leu Leu Ser Glu
        515                 520                 525

Leu

<210> SEQ ID NO 28
<211> LENGTH: 534
<212> TYPE: PRT
<213> ORGANISM: Artificial Sequence
<220> FEATURE:
<223> OTHER INFORMATION: Synthetic:
    ERG11(1a:80a):Sr.KAH_mutant#10(47a:500a)

<400> SEQUENCE: 28

Met Ser Ala Thr Lys Ser Ile Val Gly Glu Ala Leu Glu Tyr Val Asn
1               5                   10                  15

Ile Gly Leu Ser His Phe Leu Ala Leu Pro Leu Ala Gln Arg Ile Ser
            20                  25                  30

Leu Ile Ile Ile Ile Pro Phe Ile Tyr Asn Ile Val Trp Gln Leu Leu
        35                  40                  45

```
Tyr Ser Leu Arg Lys Asp Arg Pro Pro Leu Val Phe Tyr Trp Ile Pro
         50                  55                  60

Trp Val Gly Ser Ala Val Val Tyr Gly Met Lys Pro Tyr Glu Phe Phe
 65                  70                  75                  80

Leu Lys Lys Pro Leu Tyr Arg Thr Leu Ala Lys Ile Ala Ala Lys Tyr
                 85                  90                  95

Gly Pro Ile Leu Gln Leu Gln Leu Gly Tyr Arg Arg Val Leu Val Ile
            100                 105                 110

Ser Ser Pro Ser Ala Ala Glu Glu Cys Phe Thr Asn Asn Asp Val Ile
        115                 120                 125

Phe Ala Asn Arg Pro Lys Thr Leu Phe Gly Lys Ile Val Gly Gly Thr
130                 135                 140

Ser Leu Gly Ser Leu Ser Tyr Gly Asp Gln Trp Arg Asn Leu Arg Arg
145                 150                 155                 160

Val Ala Ser Ile Glu Ile Leu Ser Val His Arg Leu Asn Glu Phe His
                165                 170                 175

Asp Ile Arg Val Asp Glu Asn Arg Leu Leu Ile Arg Lys Leu Arg Asp
                180                 185                 190

Ser Ser Ser Pro Val Thr Leu Arg Thr Val Phe Tyr Ala Leu Thr Leu
        195                 200                 205

Asn Val Ile Met Arg Met Ile Ser Gly Lys Arg Tyr Phe Asp Ser Gly
210                 215                 220

Asp Arg Glu Leu Glu Glu Gly Lys Arg Phe Arg Glu Ile Leu Asp
225                 230                 235                 240

Glu Thr Leu Leu Leu Ala Gly Ala Ser Asn Val Gly Asp Tyr Leu Pro
                245                 250                 255

Ile Leu Asn Trp Leu Gly Val Lys Ser Leu Glu Lys Lys Leu Ile Ala
            260                 265                 270

Leu Gln Lys Lys Arg Asp Asp Phe Phe Gln Gly Leu Ile Glu Gln Val
        275                 280                 285

Arg Lys Ser Arg Gly Ala Lys Val Gly Lys Gly Arg Lys Thr Met Ile
        290                 295                 300

Glu Leu Leu Leu Ser Leu Gln Glu Ser Glu Pro Glu Tyr Tyr Thr Asp
305                 310                 315                 320

Ala Met Ile Arg Ser Phe Val Leu Gly Leu Leu Ala Ala Gly Ser Asp
                325                 330                 335

Thr Ser Ala Leu Thr Leu Glu Trp Ala Met Ser Leu Leu Leu Asn His
            340                 345                 350

Pro His Val Leu Lys Lys Ala Gln Ala Glu Ile Asp Arg Val Ile Gly
        355                 360                 365

Asn Asn Arg Leu Ile Asp Glu Ser Asp Ile Gly Asn Ile Pro Tyr Leu
370                 375                 380

Gly Cys Ile Ile Asn Glu Thr Leu Arg Leu Tyr Pro Ala Gly Pro Leu
385                 390                 395                 400

Leu Phe Pro His Glu Ser Ser Ala Asp Cys Val Ile Ser Gly Tyr Asn
                405                 410                 415

Ile Pro Arg Gly Thr Met Leu Ile Val Asn Gln Trp Ala Ile His His
            420                 425                 430

Asp Pro Lys Val Trp Asp Asp Pro Glu Thr Phe Lys Pro Glu Arg Phe
        435                 440                 445

Gln Gly Leu Glu Gly Thr Arg Asp Gly Phe Lys Leu Met Pro Phe Gly
        450                 455                 460
```

Ser Gly Arg Arg Gly Cys Pro Gly Glu Gly Leu Ala Ile Arg Leu Leu
465                 470                 475                 480

Gly Met Thr Leu Gly Ser Val Ile Gln Cys Phe Asp Trp Glu Arg Val
            485                 490                 495

Gly Asp Glu Met Val Asp Met Thr Glu Gly Leu Gly Val Thr Leu Pro
        500                 505                 510

Lys Ala Val Pro Leu Val Ala Lys Cys Lys Pro Arg Ser Glu Met Thr
    515                 520                 525

Asn Leu Leu Ser Glu Leu
    530

<210> SEQ ID NO 29
<211> LENGTH: 597
<212> TYPE: PRT
<213> ORGANISM: Artificial Sequence
<220> FEATURE:
<223> OTHER INFORMATION: Synthetic:
    NUS1(1a:119a):Sr.KAH_mutant#10(23a:500a)

<400> SEQUENCE: 29

Met Pro Thr Met Ile Lys Lys Asp Asp Lys Ala Met Glu Pro Pro Asn
1               5                   10                  15

Glu Lys Pro His Arg Lys Ile Glu Arg Asp Asp Val Pro Glu Ser Ser
            20                  25                  30

Asn His Ile Pro Pro Pro Glu Ser Gly Val Leu Lys Gly Gly Lys Val
        35                  40                  45

Asn Ser Lys Thr Arg Ala Leu Lys Ala Val Thr Ser Ile Ile Ala Asp
    50                  55                  60

Ala Asp Glu Asn Pro Gln Lys Lys Val Asn Asn Glu Thr Asn Gly Val
65                  70                  75                  80

Gln Lys Gln Lys Thr Glu Asp Leu Ser Lys Arg Ile Gly Lys Phe Glu
            85                  90                  95

Tyr Leu Phe Tyr Lys Phe Leu Leu Val Leu Leu Tyr Ile Cys Phe Gly
        100                 105                 110

Leu Phe Arg Tyr Gly Gln Tyr Leu Arg Arg Lys Ser Ala Asn Leu Pro
    115                 120                 125

Pro Thr Val Phe Pro Ser Ile Pro Ile Ile Gly His Leu Tyr Leu Leu
130                 135                 140

Lys Lys Pro Leu Tyr Arg Thr Leu Ala Lys Ile Ala Ala Lys Tyr Gly
145                 150                 155                 160

Pro Ile Leu Gln Leu Gln Leu Gly Tyr Arg Arg Val Leu Val Ile Ser
            165                 170                 175

Ser Pro Ser Ala Ala Glu Glu Cys Phe Thr Asn Asn Asp Val Ile Phe
        180                 185                 190

Ala Asn Arg Pro Lys Thr Leu Phe Gly Lys Ile Val Gly Gly Thr Ser
    195                 200                 205

Leu Gly Ser Leu Ser Tyr Gly Asp Gln Trp Arg Asn Leu Arg Arg Val
210                 215                 220

Ala Ser Ile Glu Ile Leu Ser Val His Arg Leu Asn Glu Phe His Asp
225                 230                 235                 240

Ile Arg Val Asp Glu Asn Arg Leu Leu Ile Arg Lys Leu Arg Asp Ser
            245                 250                 255

Ser Ser Pro Val Thr Leu Arg Thr Val Phe Tyr Ala Leu Thr Leu Asn
        260                 265                 270

Val Ile Met Arg Met Ile Ser Gly Lys Arg Tyr Phe Asp Ser Gly Asp
    275                 280                 285

```
Arg Glu Leu Glu Glu Glu Gly Lys Arg Phe Arg Glu Ile Leu Asp Glu
            290                 295                 300

Thr Leu Leu Leu Ala Gly Ala Ser Asn Val Gly Asp Tyr Leu Pro Ile
305                 310                 315                 320

Leu Asn Trp Leu Gly Val Lys Ser Leu Glu Lys Lys Leu Ile Ala Leu
                325                 330                 335

Gln Lys Lys Arg Asp Asp Phe Phe Gln Gly Leu Ile Glu Gln Val Arg
            340                 345                 350

Lys Ser Arg Gly Ala Lys Val Gly Lys Gly Arg Lys Thr Met Ile Glu
        355                 360                 365

Leu Leu Leu Ser Leu Gln Glu Ser Glu Pro Glu Tyr Tyr Thr Asp Ala
370                 375                 380

Met Ile Arg Ser Phe Val Leu Gly Leu Leu Ala Ala Gly Ser Asp Thr
385                 390                 395                 400

Ser Ala Leu Thr Leu Glu Trp Ala Met Ser Leu Leu Leu Asn His Pro
                405                 410                 415

His Val Leu Lys Lys Ala Gln Ala Glu Ile Asp Arg Val Ile Gly Asn
                420                 425                 430

Asn Arg Leu Ile Asp Glu Ser Asp Ile Gly Asn Ile Pro Tyr Leu Gly
            435                 440                 445

Cys Ile Ile Asn Glu Thr Leu Arg Leu Tyr Pro Ala Gly Pro Leu Leu
450                 455                 460

Phe Pro His Glu Ser Ser Ala Asp Cys Val Ile Ser Gly Tyr Asn Ile
465                 470                 475                 480

Pro Arg Gly Thr Met Leu Ile Val Asn Gln Trp Ala Ile His His Asp
                485                 490                 495

Pro Lys Val Trp Asp Asp Pro Glu Thr Phe Lys Pro Glu Arg Phe Gln
            500                 505                 510

Gly Leu Glu Gly Thr Arg Asp Gly Phe Lys Leu Met Pro Phe Gly Ser
        515                 520                 525

Gly Arg Arg Gly Cys Pro Gly Glu Gly Leu Ala Ile Arg Leu Leu Gly
    530                 535                 540

Met Thr Leu Gly Ser Val Ile Gln Cys Phe Asp Trp Glu Arg Val Gly
545                 550                 555                 560

Asp Glu Met Val Asp Met Thr Glu Gly Leu Gly Val Thr Leu Pro Lys
                565                 570                 575

Ala Val Pro Leu Val Ala Lys Cys Lys Pro Arg Ser Glu Met Thr Asn
                580                 585                 590

Leu Leu Ser Glu Leu
            595

<210> SEQ ID NO 30
<211> LENGTH: 540
<212> TYPE: PRT
<213> ORGANISM: Artificial Sequence
<220> FEATURE:
<223> OTHER INFORMATION: Synthetic:
      RCR1(1a:62a):Sr.KAH_mutant#10(23a:500a)

<400> SEQUENCE: 30

Met Gly Leu Ile Ser Tyr Glu Asn Glu Ala Ile Asn Glu Val Lys Lys
1               5                   10                  15

Ala Asp Asn His His Val Ser Lys Phe Val Thr Ser Tyr Tyr Gly Pro
            20                  25                  30
```

```
Ser Ser Ser Ser Trp Gln Ser Gly Arg Trp Ile Leu Phe Val Leu Phe
            35              40              45

Val Ala Ala Val Ile Leu Ile Leu Phe Thr Phe Val Ala Leu Arg
 50              55              60

Arg Lys Ser Ala Asn Leu Pro Pro Thr Val Phe Pro Ser Ile Pro Ile
 65              70              75                           80

Ile Gly His Leu Tyr Leu Leu Lys Lys Pro Leu Tyr Arg Thr Leu Ala
                 85              90              95

Lys Ile Ala Ala Lys Tyr Gly Pro Ile Leu Gln Leu Gln Leu Gly Tyr
                100             105             110

Arg Arg Val Leu Val Ile Ser Ser Pro Ser Ala Ala Glu Glu Cys Phe
            115             120             125

Thr Asn Asn Asp Val Ile Phe Ala Asn Arg Pro Lys Thr Leu Phe Gly
            130             135             140

Lys Ile Val Gly Gly Thr Ser Leu Gly Ser Leu Ser Tyr Gly Asp Gln
145             150             155             160

Trp Arg Asn Leu Arg Arg Val Ala Ser Ile Glu Ile Leu Ser Val His
                165             170             175

Arg Leu Asn Glu Phe His Asp Ile Arg Val Asp Glu Asn Arg Leu Leu
            180             185             190

Ile Arg Lys Leu Arg Asp Ser Ser Pro Val Thr Leu Arg Thr Val
            195             200             205

Phe Tyr Ala Leu Thr Leu Asn Val Ile Met Arg Met Ile Ser Gly Lys
210             215             220

Arg Tyr Phe Asp Ser Gly Asp Arg Glu Leu Glu Glu Gly Lys Arg
225             230             235             240

Phe Arg Glu Ile Leu Asp Glu Thr Leu Leu Ala Gly Ala Ser Asn
                245             250             255

Val Gly Asp Tyr Leu Pro Ile Leu Asn Trp Leu Gly Val Lys Ser Leu
                260             265             270

Glu Lys Lys Leu Ile Ala Leu Gln Lys Lys Arg Asp Asp Phe Phe Gln
            275             280             285

Gly Leu Ile Glu Gln Val Arg Lys Ser Arg Gly Ala Lys Val Gly Lys
            290             295             300

Gly Arg Lys Thr Met Ile Glu Leu Leu Leu Ser Leu Gln Glu Ser Glu
305             310             315             320

Pro Glu Tyr Tyr Thr Asp Ala Met Ile Arg Ser Phe Val Leu Gly Leu
                325             330             335

Leu Ala Ala Gly Ser Asp Thr Ser Ala Leu Thr Leu Glu Trp Ala Met
            340             345             350

Ser Leu Leu Leu Asn His Pro His Val Leu Lys Lys Ala Gln Ala Glu
            355             360             365

Ile Asp Arg Val Ile Gly Asn Asn Arg Leu Ile Asp Glu Ser Asp Ile
            370             375             380

Gly Asn Ile Pro Tyr Leu Gly Cys Ile Ile Asn Glu Thr Leu Arg Leu
385             390             395             400

Tyr Pro Ala Gly Pro Leu Leu Phe Pro His Glu Ser Ser Ala Asp Cys
                405             410             415

Val Ile Ser Gly Tyr Asn Ile Pro Arg Gly Thr Met Leu Ile Val Asn
            420             425             430

Gln Trp Ala Ile His His Asp Pro Lys Val Trp Asp Asp Pro Glu Thr
            435             440             445
```

```
Phe Lys Pro Glu Arg Phe Gln Gly Leu Glu Gly Thr Arg Asp Gly Phe
    450                 455                 460

Lys Leu Met Pro Phe Gly Ser Gly Arg Arg Gly Cys Pro Gly Glu Gly
465                 470                 475                 480

Leu Ala Ile Arg Leu Leu Gly Met Thr Leu Gly Ser Val Ile Gln Cys
            485                 490                 495

Phe Asp Trp Glu Arg Val Gly Asp Glu Met Val Asp Met Thr Glu Gly
                500                 505                 510

Leu Gly Val Thr Leu Pro Lys Ala Val Pro Leu Val Ala Lys Cys Lys
            515                 520                 525

Pro Arg Ser Glu Met Thr Asn Leu Leu Ser Glu Leu
530                 535                 540
```

<210> SEQ ID NO 31
<211> LENGTH: 528
<212> TYPE: PRT
<213> ORGANISM: Artificial Sequence
<220> FEATURE:
<223> OTHER INFORMATION: Synthetic:
    SEC66(1a:50a):Sr.KAH_mutant#10(23a:500a)

<400> SEQUENCE: 31

```
Met Ser Glu Phe Asn Glu Thr Lys Phe Ser Asn Asn Gly Thr Phe Phe
1               5                   10                  15

Glu Thr Glu Glu Pro Ile Val Glu Thr Lys Ser Ile Ser Val Tyr Thr
            20                  25                  30

Pro Leu Ile Tyr Val Phe Ile Leu Val Val Ser Leu Val Met Phe Ala
        35                  40                  45

Ser Ser Leu Arg Arg Lys Ser Ala Asn Leu Pro Pro Thr Val Phe Pro
50                  55                  60

Ser Ile Pro Ile Ile Gly His Leu Tyr Leu Leu Lys Lys Pro Leu Tyr
65                  70                  75                  80

Arg Thr Leu Ala Lys Ile Ala Ala Lys Tyr Gly Pro Ile Leu Gln Leu
                85                  90                  95

Gln Leu Gly Tyr Arg Arg Val Leu Val Ile Ser Ser Pro Ser Ala Ala
            100                 105                 110

Glu Glu Cys Phe Thr Asn Asn Asp Val Ile Phe Ala Asn Arg Pro Lys
        115                 120                 125

Thr Leu Phe Gly Lys Ile Val Gly Gly Thr Ser Leu Gly Ser Leu Ser
    130                 135                 140

Tyr Gly Asp Gln Trp Arg Asn Leu Arg Arg Val Ala Ser Ile Glu Ile
145                 150                 155                 160

Leu Ser Val His Arg Leu Asn Glu Phe His Asp Ile Arg Val Asp Glu
                165                 170                 175

Asn Arg Leu Leu Ile Arg Lys Leu Arg Asp Ser Ser Pro Val Thr
            180                 185                 190

Leu Arg Thr Val Phe Tyr Ala Leu Thr Leu Asn Val Ile Met Arg Met
        195                 200                 205

Ile Ser Gly Lys Arg Tyr Phe Asp Ser Gly Asp Arg Glu Leu Glu Glu
    210                 215                 220

Glu Gly Lys Arg Phe Arg Glu Ile Leu Asp Glu Thr Leu Leu Leu Ala
225                 230                 235                 240

Gly Ala Ser Asn Val Gly Asp Tyr Leu Pro Ile Leu Asn Trp Leu Gly
                245                 250                 255

Val Lys Ser Leu Glu Lys Lys Leu Ile Ala Leu Gln Lys Lys Arg Asp
            260                 265                 270
```

```
Asp Phe Phe Gln Gly Leu Ile Glu Gln Val Arg Lys Ser Arg Gly Ala
            275                 280                 285

Lys Val Gly Lys Gly Arg Lys Thr Met Ile Glu Leu Leu Leu Ser Leu
        290                 295                 300

Gln Glu Ser Glu Pro Glu Tyr Tyr Thr Asp Ala Met Ile Arg Ser Phe
305                 310                 315                 320

Val Leu Gly Leu Leu Ala Ala Gly Ser Asp Thr Ser Ala Leu Thr Leu
                325                 330                 335

Glu Trp Ala Met Ser Leu Leu Asn His Pro His Val Leu Lys Lys
            340                 345                 350

Ala Gln Ala Glu Ile Asp Arg Val Ile Gly Asn Asn Arg Leu Ile Asp
                355                 360                 365

Glu Ser Asp Ile Gly Asn Ile Pro Tyr Leu Gly Cys Ile Ile Asn Glu
            370                 375                 380

Thr Leu Arg Leu Tyr Pro Ala Gly Pro Leu Leu Phe Pro His Glu Ser
385                 390                 395                 400

Ser Ala Asp Cys Val Ile Ser Gly Tyr Asn Ile Pro Arg Gly Thr Met
                405                 410                 415

Leu Ile Val Asn Gln Trp Ala Ile His His Asp Pro Lys Val Trp Asp
            420                 425                 430

Asp Pro Glu Thr Phe Lys Pro Glu Arg Phe Gln Gly Leu Glu Gly Thr
            435                 440                 445

Arg Asp Gly Phe Lys Leu Met Pro Phe Gly Ser Gly Arg Arg Gly Cys
        450                 455                 460

Pro Gly Glu Gly Leu Ala Ile Arg Leu Leu Gly Met Thr Leu Gly Ser
465                 470                 475                 480

Val Ile Gln Cys Phe Asp Trp Glu Arg Val Gly Asp Glu Met Val Asp
                485                 490                 495

Met Thr Glu Gly Leu Gly Val Thr Leu Pro Lys Ala Val Pro Leu Val
                500                 505                 510

Ala Lys Cys Lys Pro Arg Ser Glu Met Thr Asn Leu Leu Ser Glu Leu
            515                 520                 525

<210> SEQ ID NO 32
<211> LENGTH: 529
<212> TYPE: PRT
<213> ORGANISM: Artificial Sequence
<220> FEATURE:
<223> OTHER INFORMATION: Synthetic:
      UBP1(1a:52a):Sr.KAH_mutant#10(23a:500a)

<400> SEQUENCE: 32

Met Asp Leu Phe Ile Glu Ser Lys Ile Asn Ser Leu Leu Gln Phe Leu
1               5                   10                  15

Phe Gly Ser Arg Gln Asp Phe Leu Arg Asn Phe Lys Thr Trp Ser Asn
            20                  25                  30

Asn Asn Asn Asn Leu Ser Ile Tyr Leu Leu Ile Phe Gly Ile Val Val
        35                  40                  45

Phe Phe Tyr Leu Arg Arg Lys Ser Ala Asn Leu Pro Pro Thr Val Phe
    50                  55                  60

Pro Ser Ile Pro Ile Ile Gly His Leu Tyr Leu Leu Lys Lys Pro Leu
65                  70                  75                  80

Tyr Arg Thr Leu Ala Lys Ile Ala Ala Lys Tyr Gly Pro Ile Leu Gln
            85                  90                  95
```

```
Leu Gln Leu Gly Tyr Arg Arg Val Leu Val Ile Ser Ser Pro Ser Ala
            100                 105                 110

Ala Glu Glu Cys Phe Thr Asn Asn Asp Val Ile Phe Ala Asn Arg Pro
            115                 120                 125

Lys Thr Leu Phe Gly Lys Ile Val Gly Gly Thr Ser Leu Gly Ser Leu
    130                 135                 140

Ser Tyr Gly Asp Gln Trp Arg Asn Leu Arg Arg Val Ala Ser Ile Glu
145                 150                 155                 160

Ile Leu Ser Val His Arg Leu Asn Glu Phe His Asp Ile Arg Val Asp
                165                 170                 175

Glu Asn Arg Leu Leu Ile Arg Lys Leu Arg Asp Ser Ser Ser Pro Val
            180                 185                 190

Thr Leu Arg Thr Val Phe Tyr Ala Leu Thr Leu Asn Val Ile Met Arg
            195                 200                 205

Met Ile Ser Gly Lys Arg Tyr Phe Asp Ser Gly Asp Arg Glu Leu Glu
            210                 215                 220

Glu Glu Gly Lys Arg Phe Arg Glu Ile Leu Asp Glu Thr Leu Leu Leu
225                 230                 235                 240

Ala Gly Ala Ser Asn Val Gly Asp Tyr Leu Pro Ile Leu Asn Trp Leu
            245                 250                 255

Gly Val Lys Ser Leu Glu Lys Lys Leu Ile Ala Leu Gln Lys Lys Arg
            260                 265                 270

Asp Asp Phe Phe Gln Gly Leu Ile Glu Gln Val Arg Lys Ser Arg Gly
            275                 280                 285

Ala Lys Val Gly Lys Gly Arg Lys Thr Met Ile Glu Leu Leu Leu Ser
            290                 295                 300

Leu Gln Glu Ser Glu Pro Glu Tyr Tyr Thr Asp Ala Met Ile Arg Ser
305                 310                 315                 320

Phe Val Leu Gly Leu Leu Ala Ala Gly Ser Asp Thr Ser Ala Leu Thr
            325                 330                 335

Leu Glu Trp Ala Met Ser Leu Leu Asn His Pro His Val Leu Lys
            340                 345                 350

Lys Ala Gln Ala Glu Ile Asp Arg Val Ile Gly Asn Asn Arg Leu Ile
            355                 360                 365

Asp Glu Ser Asp Ile Gly Asn Ile Pro Tyr Leu Gly Cys Ile Ile Asn
            370                 375                 380

Glu Thr Leu Arg Leu Tyr Pro Ala Gly Pro Leu Leu Phe Pro His Glu
385                 390                 395                 400

Ser Ser Ala Asp Cys Val Ile Ser Gly Tyr Asn Ile Pro Arg Gly Thr
            405                 410                 415

Met Leu Ile Val Asn Gln Trp Ala Ile His His Asp Pro Lys Val Trp
            420                 425                 430

Asp Asp Pro Glu Thr Phe Lys Pro Glu Arg Phe Gln Gly Leu Glu Gly
            435                 440                 445

Thr Arg Asp Gly Phe Lys Leu Met Pro Phe Gly Ser Gly Arg Arg Gly
            450                 455                 460

Cys Pro Gly Glu Gly Leu Ala Ile Arg Leu Leu Gly Met Thr Leu Gly
465                 470                 475                 480

Ser Val Ile Gln Cys Phe Asp Trp Glu Arg Val Gly Asp Glu Met Val
                485                 490                 495

Asp Met Thr Glu Gly Leu Gly Val Thr Leu Pro Lys Ala Val Pro Leu
            500                 505                 510
```

```
Val Ala Lys Cys Lys Pro Arg Ser Glu Met Thr Asn Leu Leu Ser Glu
            515                 520                 525

Leu

<210> SEQ ID NO 33
<211> LENGTH: 704
<212> TYPE: PRT
<213> ORGANISM: Artemisia annua
<220> FEATURE:
<221> NAME/KEY: misc_feature
<222> LOCATION: (1)..(704)
<223> OTHER INFORMATION: wild type Artemisia annua cytochrome P450
      reductase Aa.CPR

<400> SEQUENCE: 33

Met Gln Ser Thr Thr Ser Val Lys Leu Ser Pro Phe Asp Leu Met Thr
1               5                   10                  15

Ala Leu Leu Asn Gly Lys Val Ser Phe Asp Thr Ser Asn Thr Ser Asp
            20                  25                  30

Thr Asn Ile Pro Leu Ala Val Phe Met Glu Asn Arg Glu Leu Leu Met
        35                  40                  45

Ile Leu Thr Thr Ser Val Ala Val Leu Ile Gly Cys Val Val Val Leu
    50                  55                  60

Val Trp Arg Arg Ser Ser Ser Ala Ala Lys Lys Ala Ala Glu Ser Pro
65                  70                  75                  80

Val Ile Val Val Pro Lys Lys Val Thr Glu Asp Glu Val Asp Asp Gly
                85                  90                  95

Arg Lys Lys Val Thr Val Phe Phe Gly Thr Gln Thr Gly Thr Ala Glu
            100                 105                 110

Gly Phe Ala Lys Ala Leu Val Glu Glu Ala Lys Ala Arg Tyr Glu Lys
        115                 120                 125

Ala Val Phe Lys Val Ile Asp Leu Asp Asp Tyr Ala Ala Glu Asp Asp
    130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
                165                 170                 175

Lys Trp Phe Thr Glu Gly Glu Glu Lys Gly Glu Trp Leu Asp Lys Leu
            180                 185                 190

Gln Tyr Ala Val Phe Gly Leu Gly Asn Arg Gln Tyr Glu His Phe Asn
        195                 200                 205

Lys Ile Ala Lys Val Val Asp Glu Lys Leu Val Glu Gln Gly Ala Lys
    210                 215                 220

Arg Leu Val Pro Val Gly Met Gly Asp Asp Gln Cys Ile Glu Asp
225                 230                 235                 240

Asp Phe Thr Ala Trp Lys Glu Leu Val Trp Pro Glu Leu Asp Gln Leu
                245                 250                 255

Leu Arg Asp Glu Asp Asp Thr Ser Val Ala Thr Pro Tyr Thr Ala Ala
            260                 265                 270

Val Ala Glu Tyr Arg Val Val Phe His Asp Lys Pro Gly Thr Tyr Asp
        275                 280                 285

Gln Asp Gln Leu Thr Asn Gly His Ala Val His Ala Gln His Pro
    290                 295                 300

Cys Arg Ser Asn Val Ala Val Lys Lys Glu Leu His Ser Pro Leu Ser
305                 310                 315                 320
```

Asp Arg Ser Cys Thr His Leu Glu Phe Asp Ile Ser Asn Thr Gly Leu
            325                 330                 335

Ser Tyr Glu Thr Gly Asp His Val Gly Val Tyr Val Glu Asn Leu Ser
            340                 345                 350

Glu Val Val Asp Glu Ala Glu Lys Leu Ile Gly Leu Pro Pro His Thr
            355                 360                 365

Tyr Phe Ser Val His Ala Asp Asn Glu Asp Gly Thr Pro Leu Gly Gly
            370                 375                 380

Ala Ser Leu Pro Pro Pro Phe Pro Pro Cys Thr Leu Arg Lys Ala Leu
385                 390                 395                 400

Ala Ser Tyr Ala Asp Val Leu Ser Pro Lys Lys Ser Ala Leu Leu
            405                 410                 415

Ala Leu Ala Ala His Ala Thr Asp Ser Thr Glu Ala Asp Arg Leu Lys
            420                 425                 430

Phe Leu Ala Ser Pro Ala Gly Lys Asp Glu Tyr Ala Gln Trp Ile Val
            435                 440                 445

Ala Ser His Arg Ser Leu Leu Glu Val Met Glu Ala Phe Pro Ser Ala
            450                 455                 460

Lys Pro Pro Leu Gly Val Phe Ala Ser Val Ala Pro Arg Leu Gln
465                 470                 475                 480

Pro Arg Tyr Tyr Ser Ile Ser Ser Ser Pro Arg Phe Ala Pro Asn Arg
            485                 490                 495

Ile His Val Thr Cys Ala Leu Val Tyr Glu Gln Thr Pro Ser Gly Arg
            500                 505                 510

Val His Lys Gly Val Cys Ser Thr Trp Met Lys Asn Ala Val Pro Met
            515                 520                 525

Thr Glu Ser Gln Asp Cys Ser Trp Ala Pro Ile Tyr Val Arg Thr Ser
            530                 535                 540

Asn Phe Arg Leu Pro Ser Asp Pro Lys Val Pro Val Ile Met Ile Gly
545                 550                 555                 560

Pro Gly Thr Gly Leu Ala Pro Phe Arg Gly Phe Leu Gln Glu Arg Leu
            565                 570                 575

Ala Gln Lys Glu Ala Gly Thr Glu Leu Gly Thr Ala Ile Leu Phe Phe
            580                 585                 590

Gly Cys Arg Asn Arg Lys Val Asp Phe Ile Tyr Glu Asp Glu Leu Asn
            595                 600                 605

Asn Phe Val Glu Thr Gly Ala Leu Ser Glu Leu Val Thr Ala Phe Ser
            610                 615                 620

Arg Glu Gly Ala Thr Lys Glu Tyr Val Gln His Lys Met Thr Gln Lys
625                 630                 635                 640

Ala Ser Asp Ile Trp Asn Leu Leu Ser Glu Gly Ala Tyr Leu Tyr Val
            645                 650                 655

Cys Gly Asp Ala Lys Gly Met Ala Lys Asp Val His Arg Thr Leu His
            660                 665                 670

Thr Ile Val Gln Glu Gln Gly Ser Leu Asp Ser Ser Lys Ala Glu Leu
            675                 680                 685

Tyr Val Lys Asn Leu Gln Met Ala Gly Arg Tyr Leu Arg Asp Val Trp
690                 695                 700

<210> SEQ ID NO 34
<211> LENGTH: 712
<212> TYPE: PRT
<213> ORGANISM: Arabidopsis thaliana
<220> FEATURE:

<221> NAME/KEY: misc_feature
<222> LOCATION: (1)..(712)
<223> OTHER INFORMATION: wild type Arabidopsis thaliana cytochrome P450
      reductase ATR2

<400> SEQUENCE: 34

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Phe Pro Pro
385                 390                 395                 400

Cys Asn Leu Arg Thr Ala Leu Thr Arg Tyr Ala Cys Leu Leu Ser Ser
            405                 410                 415

Pro Lys Lys Ser Ala Leu Val Ala Leu Ala Ala His Ala Ser Asp Pro
        420                 425                 430

Thr Glu Ala Glu Arg Leu Lys His Leu Ala Ser Pro Ala Gly Lys Val
            435                 440                 445

Asp Glu Tyr Ser Lys Trp Val Val Glu Ser Gln Arg Ser Leu Leu Glu
        450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
            485                 490                 495

Ser Pro Lys Ile Ala Glu Thr Arg Ile His Val Thr Cys Ala Leu Val
        500                 505                 510

Tyr Glu Lys Met Pro Thr Gly Arg Ile His Lys Gly Val Cys Ser Thr
            515                 520                 525

Trp Met Lys Asn Ala Val Pro Tyr Glu Lys Ser Glu Asn Cys Ser Ser
530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
            565                 570                 575

Arg Gly Phe Leu Gln Glu Arg Leu Ala Leu Val Glu Ser Gly Val Glu
        580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
            645                 650                 655

Ser Gln Gly Ala Tyr Leu Tyr Val Cys Gly Asp Ala Lys Gly Met Ala
        660                 665                 670

Arg Asp Val His Arg Ser Leu His Thr Ile Ala Gln Glu Gln Gly Ser
            675                 680                 685

Met Asp Ser Thr Lys Ala Glu Gly Phe Val Lys Asn Leu Gln Thr Ser
        690                 695                 700

Gly Arg Tyr Leu Arg Asp Val Trp
705                 710

<210> SEQ ID NO 35
<211> LENGTH: 548
<212> TYPE: PRT
<213> ORGANISM: Saccharomyces cerevisiae
<220> FEATURE:
<221> NAME/KEY: misc_feature
<222> LOCATION: (1)..(548)
<223> OTHER INFORMATION: wild type Saccharomyces cerevisiae Alg11
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (75)..(75)

<223> OTHER INFORMATION: Xaa can be any naturally occurring amino acid

<400> SEQUENCE: 35

```
Met Gly Ser Ala Trp Thr Asn Tyr Asn Phe Glu Glu Val Lys Ser His
1               5                   10                  15

Phe Gly Phe Lys Lys Tyr Val Val Ser Ser Leu Val Leu Val Tyr Gly
            20                  25                  30

Leu Ile Lys Val Leu Thr Trp Ile Phe Arg Gln Trp Val Tyr Ser Xaa
        35                  40                  45

Leu Asn Pro Phe Ser Lys Ser Ser Leu Leu Asn Arg Ala Val Ala
    50                  55                  60

Ser Cys Gly Glu Lys Asn Val Lys Val Phe Xaa Phe Phe His Pro Tyr
65                  70                  75                  80

Cys Asn Ala Gly Gly Gly Glu Lys Val Leu Trp Lys Ala Val Asp
                85                  90                  95

Ile Thr Leu Arg Lys Asp Ala Lys Asn Val Ile Val Ile Tyr Ser Gly
                100                 105                 110

Asp Phe Val Asn Gly Glu Asn Ile Thr Pro Glu Asn Ile Leu Asn Asn
            115                 120                 125

Val Lys Ala Lys Phe Asp Tyr Asp Leu Asp Ser Asp Arg Ile Phe Phe
    130                 135                 140

Ile Ser Leu Lys Leu Arg Tyr Leu Val Asp Ser Ser Thr Trp Lys His
145                 150                 155                 160

Phe Thr Leu Ile Gly Gln Ala Ile Gly Ser Met Ile Leu Ala Phe Glu
                165                 170                 175

Ser Ile Ile Gln Cys Pro Pro Asp Ile Trp Ile Asp Thr Met Gly Tyr
                180                 185                 190

Pro Phe Ser Tyr Pro Ile Ile Ala Arg Phe Leu Arg Arg Ile Pro Ile
            195                 200                 205

Val Thr Tyr Thr His Tyr Pro Ile Met Ser Lys Asp Met Leu Asn Lys
    210                 215                 220

Leu Phe Lys Met Pro Lys Lys Gly Ile Lys Gly Tyr Gly Lys Ile Leu
225                 230                 235                 240

Tyr Trp Lys Val Phe Met Leu Ile Tyr Gln Ser Ile Gly Ser Lys Ile
                245                 250                 255

Asp Ile Val Ile Thr Asn Ser Thr Trp Thr Asn Asn His Ile Lys Gln
                260                 265                 270

Ile Trp Gln Ser Asn Thr Cys Lys Ile Ile Tyr Pro Pro Cys Ser Thr
            275                 280                 285

Glu Lys Leu Val Asp Trp Lys Gln Lys Phe Gly Thr Ala Lys Gly Glu
    290                 295                 300

Arg Leu Asn Gln Ala Ile Val Leu Ala Gln Phe Arg Pro Glu Lys Arg
305                 310                 315                 320

His Lys Leu Ile Ile Glu Ser Phe Ala Thr Phe Leu Lys Asn Leu Pro
                325                 330                 335

Asp Ser Val Ser Pro Ile Lys Leu Ile Met Ala Gly Ser Thr Arg Ser
            340                 345                 350

Lys Gln Asp Glu Asn Tyr Val Lys Ser Leu Gln Asp Trp Ser Glu Asn
    355                 360                 365

Val Leu Lys Ile Pro Lys His Leu Ile Ser Phe Glu Lys Asn Leu Pro
    370                 375                 380

Phe Asp Lys Ile Glu Ile Leu Leu Asn Lys Ser Thr Phe Gly Val Asn
385                 390                 395                 400
```

```
Ala Met Trp Asn Glu His Phe Gly Ile Ala Val Val Glu Tyr Met Ala
                405                 410                 415

Ser Gly Leu Ile Pro Ile Val His Ala Ser Ala Gly Pro Leu Leu Asp
            420                 425                 430

Ile Val Thr Pro Trp Asp Ala Asn Gly Asn Ile Gly Lys Ala Pro Pro
        435                 440                 445

Gln Trp Glu Leu Gln Lys Lys Tyr Phe Ala Lys Leu Glu Asp Asp Gly
450                 455                 460

Glu Thr Thr Gly Phe Phe Lys Glu Pro Ser Asp Pro Asp Tyr Asn
465                 470                 475                 480

Thr Thr Lys Asp Pro Leu Arg Tyr Pro Asn Leu Ser Asp Leu Phe Leu
                485                 490                 495

Gln Ile Thr Lys Leu Asp Tyr Asp Cys Leu Arg Val Met Gly Ala Arg
            500                 505                 510

Asn Gln Gln Tyr Ser Leu Tyr Lys Phe Ser Asp Leu Lys Phe Asp Lys
        515                 520                 525

Asp Trp Glu Asn Phe Val Leu Asn Pro Ile Cys Lys Leu Leu Glu Glu
530                 535                 540

Glu Glu Arg Gly
545

<210> SEQ ID NO 36
<211> LENGTH: 530
<212> TYPE: PRT
<213> ORGANISM: Saccharomyces cerevisiae
<220> FEATURE:
<221> NAME/KEY: misc_feature
<222> LOCATION: (1)..(530)
<223> OTHER INFORMATION: wild type Saccharomyces cerevisiae Erg11

<400> SEQUENCE: 36

Met Ser Ala Thr Lys Ser Ile Val Gly Glu Ala Leu Glu Tyr Val Asn
1               5                   10                  15

Ile Gly Leu Ser His Phe Leu Ala Leu Pro Leu Ala Gln Arg Ile Ser
            20                  25                  30

Leu Ile Ile Ile Ile Pro Phe Ile Tyr Asn Ile Val Trp Gln Leu Leu
        35                  40                  45

Tyr Ser Leu Arg Lys Asp Arg Pro Pro Leu Val Phe Tyr Trp Ile Pro
50                  55                  60

Trp Val Gly Ser Ala Val Val Tyr Gly Met Lys Pro Tyr Glu Phe Phe
65                  70                  75                  80

Glu Glu Cys Gln Lys Lys Tyr Gly Asp Ile Phe Ser Phe Val Leu Leu
                85                  90                  95

Gly Arg Val Met Thr Val Tyr Leu Gly Pro Lys Gly His Glu Phe Val
            100                 105                 110

Phe Asn Ala Lys Leu Ala Asp Val Ser Ala Glu Ala Ala Tyr Ala His
        115                 120                 125

Leu Thr Thr Pro Val Phe Gly Lys Gly Val Ile Tyr Asp Cys Pro Asn
130                 135                 140

Ser Arg Leu Met Glu Gln Lys Lys Phe Val Lys Gly Ala Leu Thr Lys
145                 150                 155                 160

Glu Ala Phe Lys Ser Tyr Val Pro Leu Ile Ala Glu Glu Val Tyr Lys
                165                 170                 175

Tyr Phe Arg Asp Ser Lys Asn Phe Arg Leu Asn Glu Arg Thr Thr Gly
            180                 185                 190
```

```
Thr Ile Asp Val Met Val Thr Gln Pro Glu Met Thr Ile Phe Thr Ala
        195                 200                 205
Ser Arg Ser Leu Leu Gly Lys Glu Met Arg Ala Lys Leu Asp Thr Asp
210                 215                 220
Phe Ala Tyr Leu Tyr Ser Asp Leu Asp Lys Gly Phe Thr Pro Ile Asn
225                 230                 235                 240
Phe Val Phe Pro Asn Leu Pro Leu Glu His Tyr Arg Lys Arg Asp His
                245                 250                 255
Ala Gln Lys Ala Ile Ser Gly Thr Tyr Met Ser Leu Ile Lys Glu Arg
            260                 265                 270
Arg Lys Asn Asn Asp Ile Gln Asp Arg Asp Leu Ile Asp Ser Leu Met
        275                 280                 285
Lys Asn Ser Thr Tyr Lys Asp Gly Val Lys Met Thr Asp Gln Glu Ile
    290                 295                 300
Ala Asn Leu Leu Ile Gly Val Leu Met Gly Gly Gln His Thr Ser Ala
305                 310                 315                 320
Ala Thr Ser Ala Trp Ile Leu Leu His Leu Ala Glu Arg Pro Asp Val
                325                 330                 335
Gln Gln Glu Leu Tyr Glu Glu Gln Met Arg Val Leu Asp Gly Gly Lys
            340                 345                 350
Lys Glu Leu Thr Tyr Asp Leu Leu Gln Glu Met Pro Leu Leu Asn Gln
        355                 360                 365
Thr Ile Lys Glu Thr Leu Arg Met His His Pro Leu His Ser Leu Phe
    370                 375                 380
Arg Lys Val Met Lys Asp Met His Val Pro Asn Thr Ser Tyr Val Ile
385                 390                 395                 400
Pro Ala Gly Tyr His Val Leu Val Ser Pro Gly Tyr Thr His Leu Arg
                405                 410                 415
Asp Glu Tyr Phe Pro Asn Ala His Gln Phe Asn Ile His Arg Trp Asn
            420                 425                 430
Asn Asp Ser Ala Ser Ser Tyr Ser Val Asp Glu Glu Val Asp Tyr Gly
        435                 440                 445
Phe Gly Ala Ile Ser Lys Gly Val Ser Ser Pro Tyr Leu Pro Phe Gly
    450                 455                 460
Gly Gly Arg His Arg Cys Ile Gly Glu His Phe Ala Tyr Cys Gln Leu
465                 470                 475                 480
Gly Val Leu Met Ser Ile Phe Ile Arg Thr Leu Lys Trp His Tyr Pro
                485                 490                 495
Glu Gly Lys Thr Val Pro Pro Asp Phe Thr Ser Met Val Thr Leu
            500                 505                 510
Pro Thr Gly Pro Ala Lys Ile Ile Trp Glu Lys Arg Asn Pro Glu Gln
        515                 520                 525
Lys Ile
    530

<210> SEQ ID NO 37
<211> LENGTH: 375
<212> TYPE: PRT
<213> ORGANISM: Saccharomyces cerevisiae
<220> FEATURE:
<221> NAME/KEY: misc_feature
<222> LOCATION: (1)..(375)
<223> OTHER INFORMATION: wild type Saccharomyces cerevisiae Nus1p
```

<400> SEQUENCE: 37

```
Met Pro Thr Met Ile Lys Lys Asp Asp Lys Ala Met Glu Pro Pro Asn
1               5                   10                  15

Glu Lys Pro His Arg Lys Ile Glu Arg Asp Asp Val Pro Glu Ser Ser
            20                  25                  30

Asn His Ile Pro Pro Glu Ser Gly Val Leu Lys Gly Gly Lys Val
        35                  40                  45

Asn Ser Lys Thr Arg Ala Leu Lys Ala Val Thr Ser Ile Ile Ala Asp
    50                  55                  60

Ala Asp Glu Asn Pro Gln Lys Lys Val Asn Asn Glu Thr Asn Gly Val
65                  70                  75                  80

Gln Lys Gln Lys Thr Glu Asp Leu Ser Lys Arg Ile Gly Lys Phe Glu
                85                  90                  95

Tyr Leu Phe Tyr Lys Phe Leu Leu Val Leu Leu Tyr Ile Cys Phe Gly
                100                 105                 110

Leu Phe Arg Tyr Gly Gln Tyr Gln Tyr His Lys Met Lys Leu Arg Ile
            115                 120                 125

Phe Ser Ile Ile Tyr Asn His Ala Tyr Thr Pro Gln Leu Ile Arg Gln
130                 135                 140

Asp Val Ile Pro Leu Lys Lys Ile Pro Lys Arg Leu Ala Ala Ile Leu
145                 150                 155                 160

Glu Val Lys Pro Val Gly Asp Val Gly Gly Val Thr Gly Leu Leu
                165                 170                 175

Asn Asp Ala Ser Glu Ile Val Cys Trp Thr Val Ser Ala Gly Ile Lys
            180                 185                 190

His Leu Met Leu Tyr Asp Tyr Asp Gly Ile Leu Gln Arg Asn Val Pro
                195                 200                 205

Glu Leu Arg Met Glu Ile His Ser Asn Leu Ala Lys Tyr Phe Gly Pro
210                 215                 220

Ala His Val Pro Asn Tyr Ala Val Lys Ile Pro His Ser Asn Lys Ile
225                 230                 235                 240

Phe Tyr Asn Leu Asp Gly Ile Glu Thr Glu Thr Asp Val Gly Asn Glu
                245                 250                 255

Ile Glu Ala Asn Gln Glu Lys Asp Lys Ile Ala Ile Glu Ile Ser Leu
            260                 265                 270

Leu Ser Asn Arg Asp Gly Arg Glu Thr Ile Val Asp Leu Thr Lys Thr
        275                 280                 285

Met Ala Glu Leu Cys Ala Val Asn Glu Leu Ser Val Ser Asp Ile Thr
290                 295                 300

Met Asp Leu Val Asp Ser Glu Leu Lys Gln Leu Val Gly Pro Glu Pro
305                 310                 315                 320

Asp Leu Leu Tyr Phe Gly Pro Ser Leu Asp Leu Gln Gly Phe Pro
                325                 330                 335

Pro Trp His Ile Arg Leu Thr Glu Phe Tyr Trp Glu Lys Asp Asn Asn
            340                 345                 350

Glu Val Ile Tyr Ser Val Phe Ile Arg Gly Leu Arg Gln Tyr Ala Gly
                355                 360                 365

Cys Lys Val Asn Val Gly Lys
        370                 375
```

<210> SEQ ID NO 38
<211> LENGTH: 213
<212> TYPE: PRT

```
<213> ORGANISM: Saccharomyces cerevisiae
<220> FEATURE:
<221> NAME/KEY: misc_feature
<222> LOCATION: (1)..(213)
<223> OTHER INFORMATION: wild type Saccharomyces cerevisiae Rcr1

<400> SEQUENCE: 38

Met Gly Leu Ile Ser Tyr Glu Asn Glu Ala Ile Asn Glu Val Lys Lys
1               5                   10                  15

Ala Asp Asn His His Val Ser Lys Phe Val Thr Ser Tyr Tyr Gly Pro
            20                  25                  30

Ser Ser Ser Ser Trp Gln Ser Gly Arg Trp Ile Leu Phe Val Leu Phe
        35                  40                  45

Val Ala Ala Val Ile Leu Ile Ile Leu Phe Thr Phe Val Ala Asn Arg
    50                  55                  60

Arg Arg Arg Arg Met Gly Arg Ala Pro Ile Arg Gly Thr Ala Trp Leu
65                  70                  75                  80

Thr Pro Pro Ser Tyr Arg Gln Ser Gln Gln Gln Tyr Thr Gly Thr Val
                85                  90                  95

Gln Gln Arg Thr Asp Asp Tyr Val Pro Glu Tyr Thr Glu Thr Ala Asn
            100                 105                 110

Glu His Asp Leu Gly Tyr Tyr Asp Gln Arg Gly Glu Phe His Pro Asn
        115                 120                 125

Asp Lys Ala Ala Tyr Val Ala Pro Pro Leu Val Gln Glu Cys Ser
    130                 135                 140

Ser Glu Ser Val Asn Ser Leu Glu Arg Pro Ala Ala Val Ile His
145                 150                 155                 160

Gln Ala Asn Ser Leu Asp Thr Asp Tyr Gly Leu Thr Arg Pro Ser Asn
                165                 170                 175

Gly Arg Val Pro Ala Val Ser Asp Thr Val Glu Gln Leu Glu Arg Leu
            180                 185                 190

Pro Gly Gly Thr Thr Thr Gln Glu Ile Asn Pro Pro Glu Arg Ala Lys
        195                 200                 205

Val Asn Ala Arg Ser
    210

<210> SEQ ID NO 39
<211> LENGTH: 206
<212> TYPE: PRT
<213> ORGANISM: Saccharomyces cerevisiae
<220> FEATURE:
<221> NAME/KEY: misc_feature
<222> LOCATION: (1)..(206)
<223> OTHER INFORMATION: wild type Saccharomyces cerevisiae Sec66p

<400> SEQUENCE: 39

Met Ser Glu Phe Asn Glu Thr Lys Phe Ser Asn Asn Gly Thr Phe Phe
1               5                   10                  15

Glu Thr Glu Glu Pro Ile Val Glu Thr Lys Ser Ile Ser Val Tyr Thr
            20                  25                  30

Pro Leu Ile Tyr Val Phe Ile Leu Val Val Ser Leu Val Met Phe Ala
        35                  40                  45

Ser Ser Tyr Arg Lys Lys Gln Ala Lys Lys Ile Ser Glu Gln Pro Ser
    50                  55                  60

Ile Phe Asp Glu Asn Asp Ala His Asp Leu Tyr Phe Gln Ile Lys Glu
65                  70                  75                  80

Met Ser Glu Asn Glu Lys Ile His Glu Lys Val Leu Lys Ala Ala Leu
                85                  90                  95
```

```
Leu Asn Arg Gly Ala Glu Ser Val Arg Arg Ser Leu Lys Leu Lys Glu
                100                 105                 110

Leu Ala Pro Gln Ile Asn Leu Leu Tyr Lys Asn Gly Ser Ile Gly Glu
            115                 120                 125

Asp Tyr Trp Lys Arg Phe Glu Thr Glu Val Lys Leu Ile Glu Leu Glu
130                 135                 140

Phe Lys Asp Thr Leu Gln Glu Ala Glu Arg Leu Gln Pro Gly Trp Val
145                 150                 155                 160

Gln Leu Phe Val Met Val Cys Lys Glu Ile Cys Phe Asn Gln Ala Leu
                165                 170                 175

Ser Arg Arg Tyr Gln Ser Thr Leu Lys Arg Lys Glu Val Cys Ile Lys
                180                 185                 190

Glu Trp Glu Leu Lys Ile Asn Asn Asp Gly Arg Leu Val Asn
            195                 200                 205

<210> SEQ ID NO 40
<211> LENGTH: 811
<212> TYPE: PRT
<213> ORGANISM: Saccharomyces cerevisiae
<220> FEATURE:
<221> NAME/KEY: misc_feature
<222> LOCATION: (1)..(811)
<223> OTHER INFORMATION: wild type Saccharomyces cerevisiae Ubp1p

<400> SEQUENCE: 40

Met Asp Leu Phe Ile Glu Ser Lys Ile Asn Ser Leu Leu Gln Phe Leu
1               5                   10                  15

Phe Gly Ser Arg Gln Asp Phe Leu Arg Asn Phe Lys Thr Trp Ser Asn
                20                  25                  30

Asn Asn Asn Asn Leu Ser Ile Tyr Leu Leu Ile Phe Gly Ile Val Val
            35                  40                  45

Phe Phe Tyr Lys Lys Pro Asp His Leu Asn Tyr Ile Val Glu Ser Val
50                  55                  60

Ser Glu Met Thr Thr Asn Phe Arg Asn Ser Asn Ser Leu Ser Arg Trp
65                  70                  75                  80

Leu Pro Arg Ser Lys Phe Thr His Leu Asp Glu Glu Ile Leu Lys Arg
                85                  90                  95

Gly Gly Phe Ile Ala Gly Leu Val Asn Asp Gly Asn Thr Cys Phe Met
            100                 105                 110

Asn Ser Val Leu Gln Ser Leu Ala Ser Ser Arg Glu Leu Met Glu Phe
            115                 120                 125

Leu Asp Asn Asn Val Ile Arg Thr Tyr Glu Glu Ile Glu Gln Asn Glu
130                 135                 140

His Asn Glu Glu Glu Asn Gly Gln Glu Ser Ala Gln Asp Glu Ala Thr
145                 150                 155                 160

His Lys Lys Asn Thr Arg Lys Gly Gly Lys Val Tyr Gly Lys His Lys
                165                 170                 175

Lys Lys Leu Asn Arg Lys Ser Ser Lys Glu Asp Glu Lys Ser
            180                 185                 190

Gln Glu Pro Asp Ile Thr Phe Ser Val Ala Leu Arg Asp Leu Leu Ser
            195                 200                 205

Ala Leu Asn Ala Lys Tyr Tyr Arg Asp Lys Pro Tyr Phe Lys Thr Asn
            210                 215                 220

Ser Leu Leu Arg Ala Met Ser Lys Ser Pro Arg Lys Asn Ile Leu Leu
225                 230                 235                 240
```

```
Gly Tyr Asp Gln Glu Asp Ala Gln Glu Phe Gln Asn Ile Leu Ala
                245                 250                 255

Glu Leu Glu Ser Asn Val Lys Ser Leu Asn Thr Glu Lys Leu Asp Thr
            260                 265                 270

Thr Pro Val Ala Lys Ser Glu Leu Pro Asp Asp Ala Leu Val Gly Gln
        275                 280                 285

Leu Asn Leu Gly Glu Val Gly Thr Val Tyr Ile Pro Thr Glu Gln Ile
    290                 295                 300

Asp Pro Asn Ser Ile Leu His Asp Lys Ser Ile Gln Asn Phe Thr Pro
305                 310                 315                 320

Phe Lys Leu Met Thr Pro Leu Asp Gly Ile Thr Ala Glu Arg Ile Gly
                325                 330                 335

Cys Leu Gln Cys Gly Glu Asn Gly Gly Ile Arg Tyr Ser Val Phe Ser
            340                 345                 350

Gly Leu Ser Leu Asn Leu Pro Asn Glu Asn Ile Gly Ser Thr Leu Lys
        355                 360                 365

Leu Ser Gln Leu Leu Ser Asp Trp Ser Lys Pro Glu Ile Ile Glu Gly
    370                 375                 380

Val Glu Cys Asn Arg Cys Ala Leu Thr Ala Ala His Ser His Leu Phe
385                 390                 395                 400

Gly Gln Leu Lys Glu Phe Glu Lys Lys Pro Glu Gly Ser Ile Pro Glu
                405                 410                 415

Lys Leu Ile Asn Ala Val Lys Asp Arg Val His Gln Ile Glu Glu Val
            420                 425                 430

Leu Ala Lys Pro Val Ile Asp Asp Glu Asp Tyr Lys Lys Leu His Thr
        435                 440                 445

Ala Asn Met Val Arg Lys Cys Ser Lys Ser Lys Gln Ile Leu Ile Ser
    450                 455                 460

Arg Pro Pro Pro Leu Leu Ser Ile His Ile Asn Arg Ser Val Phe Asp
465                 470                 475                 480

Pro Arg Thr Tyr Met Ile Arg Lys Asn Asn Ser Lys Val Leu Phe Lys
                485                 490                 495

Ser Arg Leu Asn Leu Ala Pro Trp Cys Cys Asp Ile Asn Glu Ile Asn
            500                 505                 510

Leu Asp Ala Arg Leu Pro Met Ser Lys Lys Glu Lys Ala Ala Gln Gln
        515                 520                 525

Glu Ser Ser Glu Asp Glu Asn Ile Gly Gly Glu Tyr Tyr Thr Lys Leu
    530                 535                 540

His Glu Arg Phe Glu Gln Glu Phe Glu Asp Ser Glu Glu Lys Glu
545                 550                 555                 560

Tyr Asp Asp Ala Glu Gly Asn Tyr Ala Ser His Tyr Asn His Thr Lys
                565                 570                 575

Asp Ile Ser Asn Tyr Asp Pro Leu Asn Gly Glu Val Asp Gly Val Thr
            580                 585                 590

Ser Asp Asp Glu Asp Glu Tyr Ile Glu Glu Thr Asp Ala Leu Gly Asn
        595                 600                 605

Thr Ile Lys Lys Arg Ile Ile Glu His Ser Asp Val Glu Asn Glu Asn
    610                 615                 620

Val Lys Asp Asn Glu Glu Leu Gln Glu Ile Asp Asn Val Ser Leu Asp
625                 630                 635                 640

Glu Pro Lys Ile Asn Val Glu Asp Gln Leu Glu Thr Ser Ser Asp Glu
                645                 650                 655
```

```
Glu Asp Val Ile Pro Ala Pro Pro Ile Asn Tyr Ala Arg Ser Phe Ser
            660             665             670

Thr Val Pro Ala Thr Pro Leu Thr Tyr Ser Leu Arg Ser Val Ile Val
        675             680             685

His Tyr Gly Thr His Asn Tyr Gly His Tyr Ile Ala Phe Arg Lys Tyr
    690             695             700

Arg Gly Cys Trp Trp Arg Ile Ser Asp Glu Thr Val Tyr Val Val Asp
705             710             715             720

Glu Ala Glu Val Leu Ser Thr Pro Gly Val Phe Met Leu Phe Tyr Glu
            725             730             735

Tyr Asp Phe Asp Glu Glu Thr Gly Lys Met Lys Asp Asp Leu Glu Ala
            740             745             750

Ile Gln Ser Asn Asn Glu Glu Asp Asp Glu Lys Glu Gln Glu Gln Glu
            755             760             765

Gln Lys Gly Val Gln Glu Pro Lys Glu Ser Gln Glu Gln Gly Glu Gly
        770             775             780

Glu Glu Gln Glu Glu Gly Gln Glu Gln Met Lys Phe Glu Arg Thr Glu
785             790             795             800

Asp His Arg Asp Ile Ser Gly Lys Asp Val Asn
            805             810
```